(12) United States Patent
Ahrens et al.

(10) Patent No.: US 8,193,121 B2
(45) Date of Patent: Jun. 5, 2012

(54) 2-(3-ALKYLTHIOBENZOYL) CYCLOHEXANEDIONES AND THEIR USE AS HERBICIDES

(75) Inventors: Hartmut Ahrens, Egelsbach (DE); Andreas Almsick, Karben (DE); Jan Dittgen, Ghent (BE); Christopher Hugh Rosinger, Hofheim (DE); Isolde Häuser-Hahn, Leverkusen (DE); Stefan Lehr, Liederbach (DE); Dieter Feucht, Eschborn (DE)

(73) Assignee: Bayer Cropscience AG, Monheim (DE)

( * ) Notice: Subject to any disclaimer, the term of this patent is extended or adjusted under 35 U.S.C. 154(b) by 72 days.

(21) Appl. No.: 12/844,148

(22) Filed: Jul. 27, 2010

(65) Prior Publication Data

US 2011/0053779 A1 Mar. 3, 2011

Related U.S. Application Data

(60) Provisional application No. 61/229,365, filed on Jul. 29, 2009.

(30) Foreign Application Priority Data

Jul. 29, 2009 (EP) .................... 09009777

(51) Int. Cl.
*A01N 37/10* (2006.01)
*A01N 35/06* (2006.01)
*C07C 321/26* (2006.01)
*C07C 63/70* (2006.01)
*C07C 317/46* (2006.01)
*A01P 13/00* (2006.01)

(52) U.S. Cl. ........ 504/324; 504/348; 562/125; 562/429; 568/36; 568/43

(58) Field of Classification Search .................. None
See application file for complete search history.

(56) References Cited

U.S. PATENT DOCUMENTS

| 4,780,127 A | 10/1988 | Michaely et al. |
| 2004/0235793 A1 | 11/2004 | Deyn et al. |

FOREIGN PATENT DOCUMENTS

| EP | 0137963 | 4/1985 |
| EP | 0249150 | 12/1987 |
| EP | 0338992 | 10/1989 |
| WO | 03/014071 | 2/2003 |

OTHER PUBLICATIONS

International Search Report Based on PCT/EP2010/004445 Dated Oct. 22, 2010.

*Primary Examiner* — Kamal Saeed
(74) *Attorney, Agent, or Firm* — Baker Donelson Bearman, Caldwell & Berkowitz, PC

(57) ABSTRACT

2-(3-Alkylthiobenzoyl)cyclohexanediones of the formula (I) are described as herbicides.

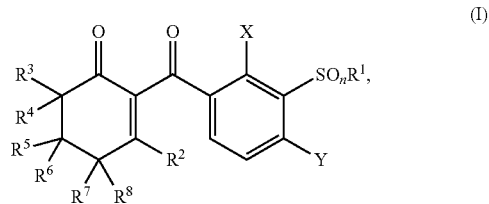

In this formula (I), X, Y, $R^1$ to $R^8$ represent radicals such as hydrogen, organic radicals such as alkyl and alkoxy.

9 Claims, No Drawings

2-(3-ALKYLTHIOBENZOYL) CYCLOHEXANEDIONES AND THEIR USE AS HERBICIDES

CROSS REFERENCE TO RELATED APPLICATION

This application claims priority to EP 09009777.5 filed Jul. 29, 2009, and U.S. Provisional Application Ser. No. 61/229,365 filed Jul. 29, 2009, the entire contents of which are incorporated by reference in their entireties.

BACKGROUND OF THE INVENTION

1. Field of the Invention

The invention relates to the technical field of herbicides, in particular that of herbicides for the selective control of broad-leaved weeds and weed grasses in crops of useful plants.

2. Description of Related Art

It is already known from various publications that certain benzoylcyclohexanediones have herbicidal properties. Thus, U.S. Pat. No. 4,780,127, EP-A-338 992, EP-A-249 150 and EP-A-137963 describe benzoylcyclohexanediones substituted at the phenyl ring by various radicals.

The herbicidal activity of the compounds known from these publications, however, is frequently inadequate. It is therefore an object of the present invention to provide further herbicidally active compounds having properties which—relative to those of the compounds disclosed in the state of the art—are improved.

SUMMARY

It has now been found that benzoylcyclohexanediones whose phenyl ring is substituted in the 2-, 3- and 4-position by selected radicals are particularly suitable as herbicides.

The present invention provides 2-(3-alkylthiobenzoyl)cyclohexanediones of the formula (I) or salts thereof

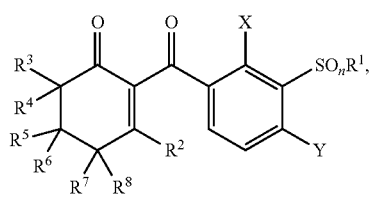

in which
$R^1$ is $(C_1-C_6)$-alkyl,
$R^2$ is hydroxyl, $SR^{13}$, $NR^{14}R^{15}$,
$R^3$ and $R^8$ independently of one another are hydrogen or $(C_1-C_4)$-alkyl, or the radicals $R^3$ and $R^8$ together form the unit Z which represents an oxygen or sulfur atom or one to four methylene groups,
$R^4$ and $R^7$ independently of one another are hydrogen or $(C_1-C_4)$-alkyl,
$R^5$ and $R^6$ independently of one another are hydrogen or $(C_1-C_4)$-alkyl or together with the carbon atom to which they are attached form a carbonyl group,
X is $OR^9$, $OCOR^9$, $OSO_2R^{10}$,
$R^9$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl-$(C_1-C_6)$-alkyl, where the six last-mentioned radicals are substituted by s radicals from the group consisting of halogen, $OR^{11}$ and $S(O)_mR^{12}$,
$R^{10}$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl-$(C_1-C_6)$-alkyl, where the six last-mentioned radicals are substituted by s radicals from the group consisting of halogen, $OR^{11}$ and $S(O)_mR^{12}$,
$R^{11}$ is hydrogen, $(C_1-C_6)$-alkyl, $(C_2-C_6)$-alkenyl or $(C_2-C_6)$-alkynyl,
$R^{12}$ is $(C_1-C_6)$-alkyl, $(C_2-C_6)$-alkenyl or $(C_2-C_6)$-alkynyl,
$R^{13}$ is $(C_1-C_4)$-alkyl, phenyl which is substituted by s radicals from the group consisting of nitro, cyano, $(C_1-C_4)$-alkyl, $(C_1-C_4)$-haloalkyl, $(C_1-C_4)$-alkoxy or $(C_1-C_4)$-haloalkoxy or is partially or fully halogenated phenyl,
$R^{14}$ is hydrogen, $(C_1-C_4)$-alkyl or $(C_1-C_4)$-alkoxy,
$R^{15}$ is hydrogen or $(C_1-C_4)$-alkyl,
or
$R^{14}$ and $R^{15}$ together with the nitrogen atom to which they are attached form a 5- or 6-membered saturated, partially saturated or unsaturated ring,
which contains zero, one or two heteroatoms selected from the group consisting of oxygen, sulfur and nitrogen,
which is substituted by s radicals from the group consisting of cyano, halogen, $(C_1-C_4)$-alkyl, $(C_1-C_4)$-haloalkyl, $(C_1-C_4)$-alkoxy and $(C_1-C_4)$-haloalkoxy,
Y is $(C_1-C_6)$-haloalkyl,
m is 0, 1 or 2,
n is 0, 1 or 2,
s is 0, 1, 2 or 3.

DETAILED DESCRIPTION OF A PREFERRED EMBODIMENT

In formula (I) and all the formulae below, alkyl radicals having more than two carbon atoms can be straight-chain or branched. Alkyl radicals are, for example, methyl, ethyl, n-oder isopropyl, n-, iso-, t-oder 2-butyl, pentyls, hexyls, such as n-hexyl, isohexyl and 1,3-dimethylbutyl. Halogen represents fluorine, chlorine, bromine or iodine.

Where a group is substituted by a plurality of radicals, this means that this group is substituted by one or more identical or different representatives of the radicals mentioned.

Depending on the nature and the attachment of the substituents, the compounds of the formula (I) may be present as stereoisomers. If, for example, one or more asymmetrically substituted carbon atoms are present, there may be enantiomers and diastereomers. There may also be stereoisomers if n is 1 (sulfoxides). Stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. The invention also relates to all stereoisomers and mixtures thereof embraced by the formula (I) but not specifically defined.

Preferred are compounds of the formula (I) in which
$R^1$ is methyl, ethyl, n-propyl or isopropyl,
$R^2$ is hydroxyl,
$R^3$ and $R^8$ independently of one another are hydrogen or $(C_1-C_4)$-alkyl, or the radicals $R^3$ and $R^8$ together form a methylene or ethylene group,
$R^4$ and $R^7$ independently of one another are hydrogen, methyl or ethyl,
$R^5$ and $R^6$ independently of one another are hydrogen, methyl or ethyl,
X is $OR^9$, $OCOR^9$, $OSO_2R^{10}$,
$R^9$ is cyclopropylmethyl or $(C_1-C_6)$-alkyl substituted by s methoxy or ethoxy groups, $R^{10}$ is $(C_1-C_6)$-alkyl substituted by s methoxy or ethoxy groups,
Y is $(C_1-C_3)$-haloalkyl,
n is 0, 1 or 2,
s is 0, 1, 2 or 3.

Particular preference is given to compounds of the formula (I) in which
$R^1$ is methyl, ethyl, n-propyl or isopropyl,
$R^2$ is hydroxyl,
$R^3$ and $R^8$ independently of one another are hydrogen, methyl or ethyl, or the radicals $R^3$ and $R^8$ together form a methylene or ethylene group,
$R^4$ and $R^7$ independently of one another are hydrogen, methyl or ethyl,
$R^5$ and $R^6$ independently of one another are hydrogen, methyl or ethyl,
X is $OR^9$,
$R^9$ is cyclopropylmethyl or ethyl or methyl substituted by s methoxy or ethoxy groups,
Y is trichloromethyl, difluoromethyl, trifluoromethyl, pentafluoroethyl or heptafluoroisopropyl,
n is 0, 1 or 2,
s is 0, 1, 2 or 3.

In all of the formulae below, the substituents and symbols have the same definition as described under formula (I), unless otherwise defined.

Compounds according to the invention in which $R^2$ is hydroxyl may be prepared, for example, by the method indicated in scheme 1, by converting a benzoic acid (II) into an acid chloride or an ester (III), subsequent base-catalyzed reaction with a cyclohexanedione (IV) and subsequent rearrangement in the presence of a cyanide source. Such methods are known to the person skilled in the art and are described, for example, in WO 03/084912. In formula (III), $L^1$ is chlorine, bromine or alkoxy.

Scheme 1

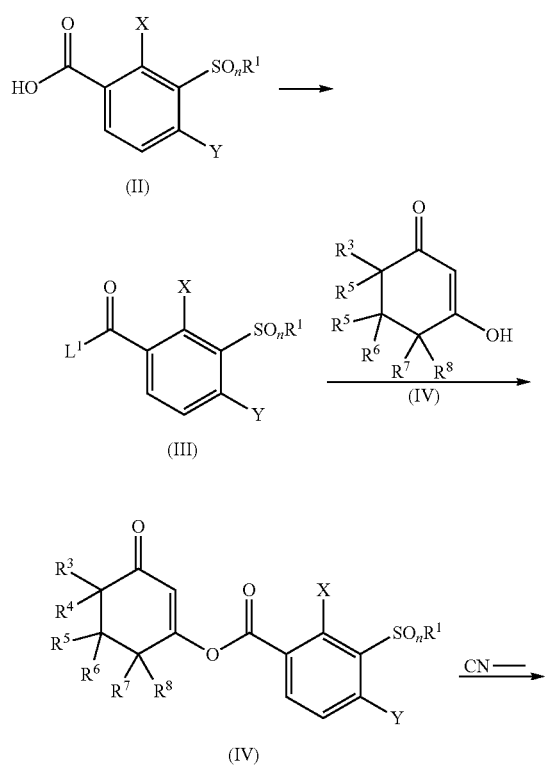

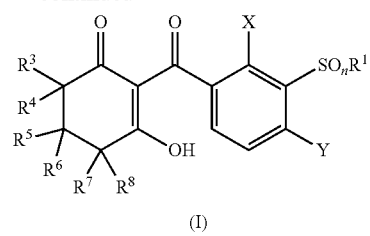

The cyclohexanediones of the formula (IV) are known and can be prepared, for example, according to the methods described in EP 0 338 992.

Compounds according to the invention in which $R^2$ has a meaning other than that of hydroxyl can be prepared in accordance with scheme 2 from the compounds according to the invention in which $R^2$ is hydroxyl, by halogenation and subsequent exchange reactions. Such reactions, which are known to the person skilled in the art, are described, for example, in WO 03/084912.

Scheme 2

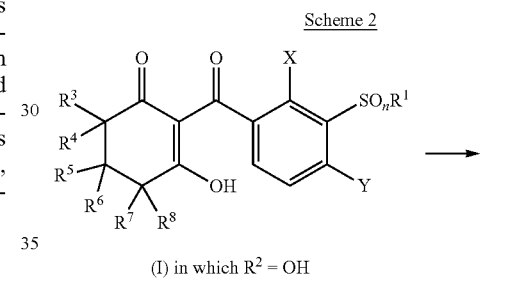

(I) in which $R^2$ = OH

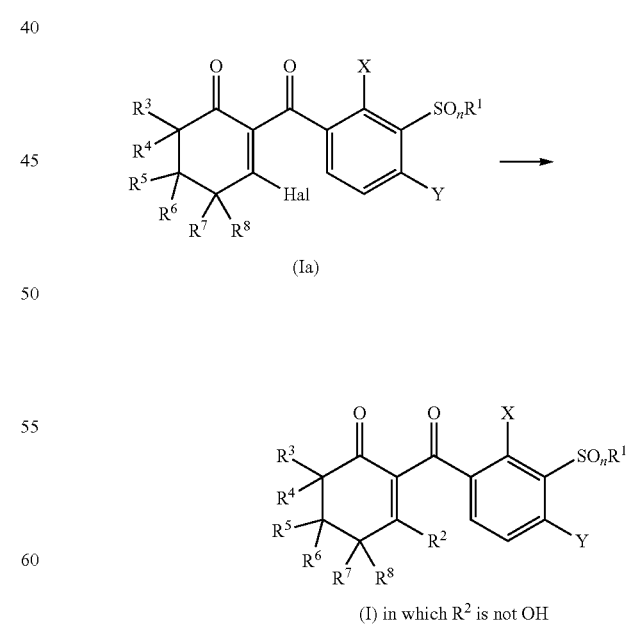

The benzoic acids (II) can be prepared from the compounds (VI) by reactions known to the person skilled in the art, for example according to scheme 3.

Scheme 3

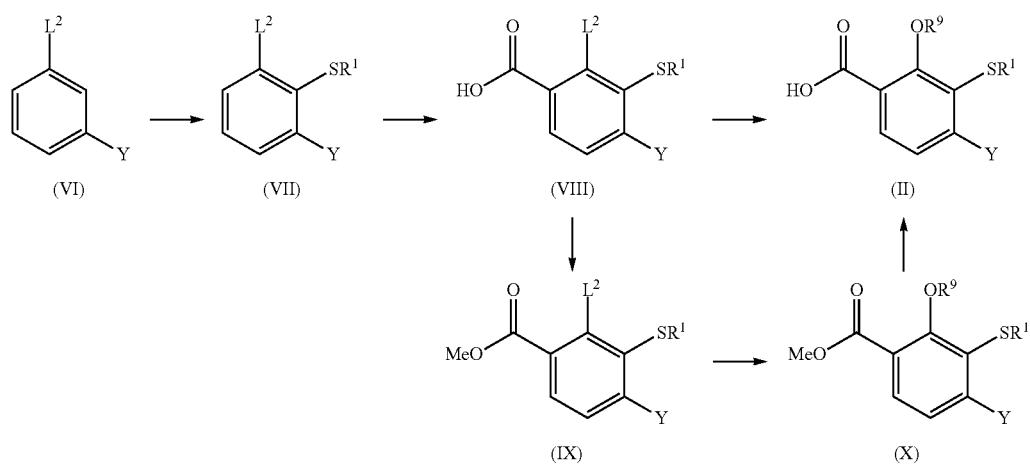

For instance, compounds of the formula (VI) in which $L^2$ is an ortho-directing substituent such as fluorine can be metallated with lithium diisopropylamide and then reacted with a thiolating reagent to give a compound of the formula (VII). A further metallation reaction, for example with n-butyllithium, and subsequent carboxylation yields benzoic acid (VII). Such reactions are known, for example, from Tetrahedron Letters 1992 (33), 49, pp. 7499-7502; J. Heterocyclic Chem. 1999, 36, p. 1453 ff. and Angew. Chem. 2005, 117, 380-398. The radical $L^2$ is then, if appropriate after esterification, exchanged for the radical $OR^9$. By reaction of the compounds (X) or (II) with oxidizing agents such as meta-chloroperbenzoic acid, the thio group is oxidized to a sulfinyl or sulfonyl group.

According to scheme 4, an exchange of group $L^2$ for $OR^9$ can also be carried out at the stage of the benzoylcyclohexanediones.

Scheme 4

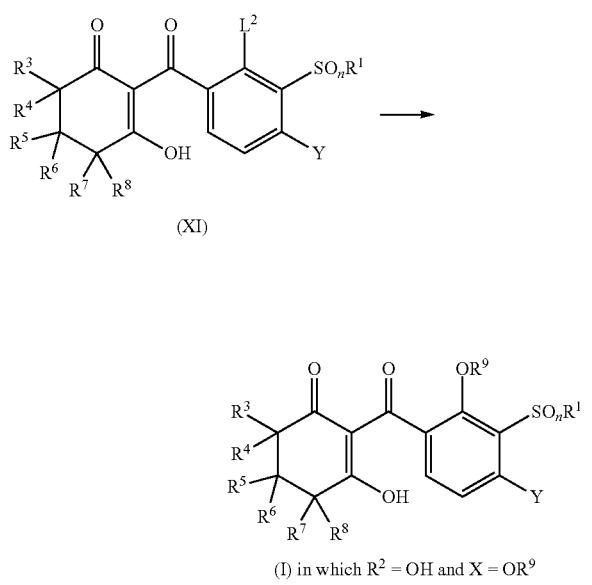

According to scheme 5, the thio radical in position 3 can also be introduced via metallation reactions from compounds (VI). Such reactions are known, for example, from Synthesis 2006, 10, 1578-1589; Org. Lett. 8 (2006) 4, 765-768 and Angew. Chem. 2005, 117, 380-398.

Scheme 5

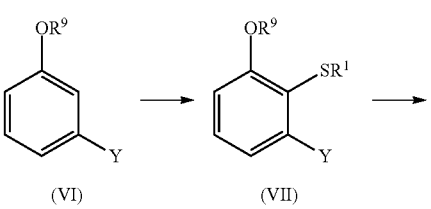

According to scheme 6, compounds (II) in which X is hydroxyl can be transferred by acylation reactions into compounds (II) in which X is $OCOR^9$ or $OSO_2R^{10}$. Such reactions are known, for example, from Houben-Weyl, Methoden der Organischen Chemie [Methods of Organic Chemistry], Georg Thieme Verlag Stuttgart, Vol. VIII, 4$^{th}$ edition 1952, p. 543 ff. and Vol. IX, fourth edition 1955, p. 388 f.

Scheme 6

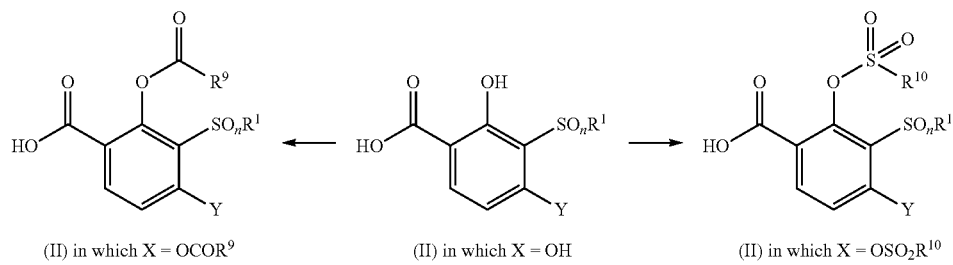

The alkylthio radical in position 3 can be oxidized to the sulfoxide or sulfone. Suitable for this purpose are a number of oxidation systems, for example peracids, such as meta-chloroperbenzoic acid, which are optionally generated in situ (for example peracetic acid in the system acetic acid/hydrogen peroxide/sodium tungstate(VI)). Such reactions are known, for example, from Houben-Weyl, Methoden der Organischen Chemie, Georg Thieme Verlag Stuttgart, Vol. E 11, additional and supplementary volumes to the fourth edition 1985, p. 702 ff., p. 718 ff. and p. 1194 ff. These oxidation reactions can also be carried out at the stage of the benzoylcyclohexanediones or the corresponding enol esters, see scheme 7.

It may be advantageous to change the order of the reaction steps described in the schemes above, or else to combine them with one another. Work-up of the respective reaction mixtures is generally carried out by known processes, for example by crystallization, aqueous-extractive work-up, by chromatographic methods or by a combination of these methods.

The compounds of the formula (II) are novel and also form part of the subject matter of the present invention.

Collections of compounds of the formula (I) and/or salts thereof which can be synthesized by the aforementioned reactions can also be prepared in a parallel manner, it being possible for this to take place in a manual, partly automated or Scheme 7

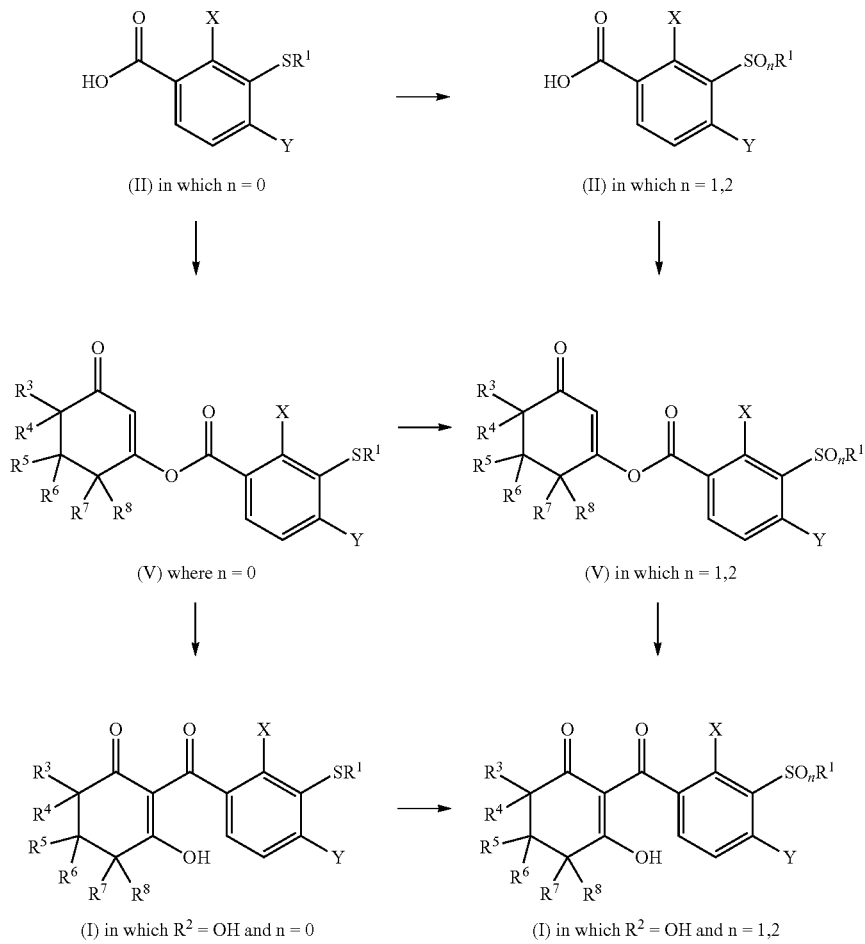

completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calpyso reaction blocks from Barnstead International, Dubuque, Iowa 52004-0797, USA or reaction stations from Radleys, Shirehill, Saffron Walden, Essex, CB 11 3AZ, England or MultiPROBE Automated Workstations from Perkin Elmer, Waltham, Mass. 02451, USA. For the parallel purification of compounds of the formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds of the formula (I) and salts thereof can take place completely or partially by solid-phase supported methods. For this purpose, individual intermediates or all intermediates in the synthesis or a synthesis adapted for the corresponding procedure are bonded to a synthesis resin. Solid-phase supported synthesis methods are sufficiently described in the specialist literature, e.g. Barry A. Bunin in "The Combinatorial Index", Verlag Academic Press, 1998 and Combinatorial—Synthesis, Analysis, Screening (editor Günther Jung), Verlag Wiley, 1999. The use of solid-phase supported synthesis methods permits a series of protocols known in the literature, which again can be carried out manually or in an automated manner. The reactions can be carried out, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editor C. O. Kappe and A. Stadler), Verlag Wiley, 2005.

The preparation according to the process described here produces compounds of the formula (I) and their salts in the form of substance collections which are called libraries. The present invention also provides libraries which comprise at least two compounds of the formula (I) and their salts.

The compounds of the formula (I) according to the invention (and/or their salts), hereinbelow also referred to together as "compounds according to the invention", have excellent herbicidal efficacy against a broad spectrum of economically important monocotyledonous and dicotyledonous annual harmful plants. The active compounds act efficiently even on perennial weeds which produce shoots from rhizomes, root stocks and other perennial organs and which are difficult to control.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storeability, composition and specific constituents. Thus, transgenic plants are known whose starch content is increased, or whose starch quality is altered, or those where the harvested material has a different fatty acid composition.

It is preferred, with regard to transgenic crops, to use the compounds according to the invention in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

It is preferred to use the compounds according to the invention or their salts in economically important transgenic crops of useful plants and ornamentals, for example of cereals such as wheat, barley, rye, oats, millet, rice, cassaya and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the above-mentioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes. These individual types of formulation are known in principle and are described, for example, in: Winnacker-Küchler, "Chemische Technologie" [Chemical technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the herbicidally active compounds are ground finely, for example in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention. In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Formulations in the form of dusts comprise from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. Here, by way of example, one and in some cases a plurality of use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]
ethanesulfonamide, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, metazosulfuron, methazole, methiozolin, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

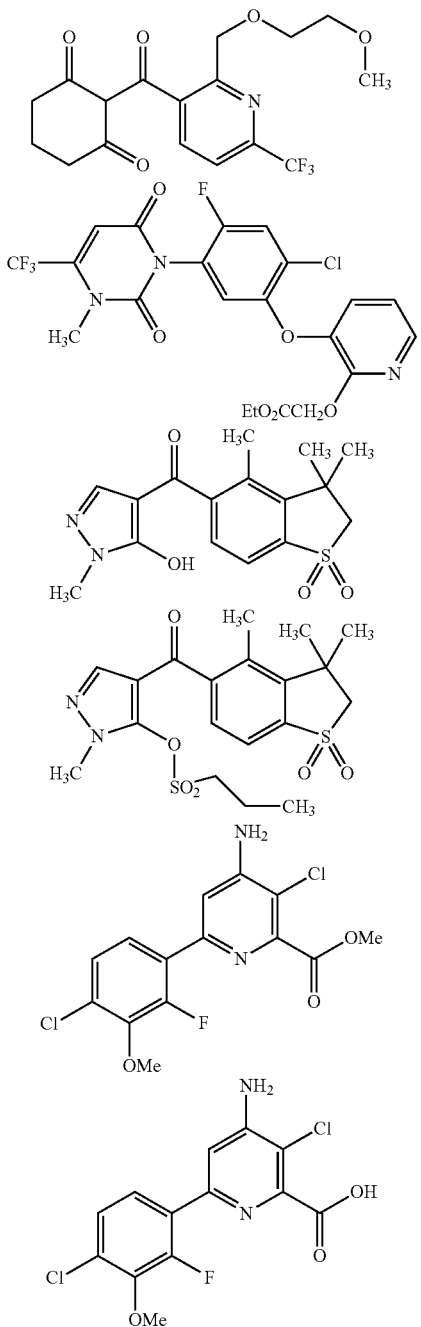

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The required application rate of the compounds of the formula (I) varies according to the external conditions such as, inter alia, temperature, humidity and the type of herbicide used. It may vary within wide limits, for example between 0.001 and 1.0 kg/ha or more of active substance; however, preferably it is between 0.005 and 750 g/ha.

The examples below illustrate the invention:

A. CHEMICAL EXAMPLES 2-(2-Methoxy-3-methylsulfinyl-4-(trifluoromethyl) benzoyl)cyclohexane-1,3-dione (Table Example No. 1-17)

Step 1: Synthesis of 1-fluoro-2-methylthio-3-(trifluoromethyl)benzene

Under an atmosphere of inert gas, 32.8 ml (1.6 M in hexane, 52.5 mmol) of n-butyllithium were added dropwise to a solution, cooled to 0° C., of 7.77 ml (55 mmol) of diisopropylamine in 100 ml of anhydrous THF, and after 10 minutes of stirring the solution was cooled to −78° C. 8.21 g (50 mmol) of 3-fluorobenzotrifluoride were added at this temperature, and the reaction mixture was stirred at this temperature for 1 h. 4.21 ml (55 mmol) of dimethyl disulfide were then added dropwise. Within about 3 h, the reaction mixture had warmed to room temperature (RT), and it was then once more cooled to 0° C. At this temperature, 10 ml of water were added dropwise, and the reaction mixture was concentrated to about ¼ of its volume. The residue was taken up in water and dichloromethane, the phases were separated and the organic phase was washed successively with water, 10 percent strength hydrochloric acid, water, saturated aqueous $NaHCO_3$ solution, water and saturated aqueous NaCl solution and dried over sodium sulfate and filtered. The solvent was removed and the residue was rectified under reduced pressure. This gave 8 g of 1-fluoro-2-methylthio-3-(trifluoromethyl)benzene of a boiling point of 68° C. at 6 mm Hg.

Step 2: Synthesis of 2-fluoro-3-methylthio-4-(trifluoromethyl)benzoic acid

Under an atmosphere of inert gas, 27.5 ml (1.6 M in hexane, 44 mmol) of n-butyllithium were added dropwise to a solution, cooled to −78° C., of 7.98 g (38 mmol) of 1-fluoro-2-methylthio-3-(trifluoromethyl)benzene in 60 ml of anhydrous THF, where the temperature of the reaction mixture should not exceed −65° C. The mixture was stirred at −78° C. for 3 h, and at this temperature a carbon dioxide stream was then introduced such that the temperature of the reaction mixture did not exceed −45° C. The mixture was then warmed to RT and then once more cooled to 0° C. For work-up, water was added dropwise at this temperature until the precipitate formed had dissolved. Diethyl ether was added, and the organic phase was extracted three times with water. The combined aqueous phases were acidified with 10 percent strength hydrochloric acid. The aqueous phase was extracted repeatedly with dichloromethane, the combined organic phases were washed with saturated aqueous NaCl solution and dried over sodium sulfate and the filtrate was then freed from the solvent. The crude product obtained in this manner was then recrystallized from gasoline (80-110° C.)/ethyl acetate. This gave 6.8 g of 2-fluoro-3-methylthio-4-(trifluoromethyl)benzoic acid.

Step 3: Synthesis of methyl 2-fluoro-3-methylthio-4-(trifluoromethyl)benzoate 5 ml of concentrated sulfuric acid were added to 20.0 g (78.7 mmol) of 2-fluoro-3-methylthio-4-(trifluoromethyl) benzoic acid in 200 ml of methanol, and the mixture was heated under reflux until HPLC analysis showed complete conversion. The mixture was cooled and the solvent was removed. The residue was taken up in water, and the mixture was extracted twice with ethyl acetate. The combined organic phases were washed once with saturated aqueous $NaHCO_3$ solution. Finally, the organic phase was dried and the filtrate was concentrated. This gave 20.5 g of methyl 2-fluoro-3-methylthio-4-(trifluoromethyl)benzoate.

Step 4: Synthesis of methyl 2-methoxy-3-methylthio-4-(trifluoromethyl)benzoate A mixture of 19.9 g (74.2 mmol) of methyl 2-fluoro-3-methylthio-4-(trifluoromethyl)benzoate and 40.1 g (30% by weight, 223 mmol) of sodium methoxide in 250 ml of methanol was heated under reflux for 6 h. For work-up, the mixture was concentrated on a rotary evaporator, the residue was taken up in water and the mixture was extracted with dichloromethane. The organic phase was dried and the filtrate was freed from the solvent. This gave 15.9 g of methyl 2-methoxy-3-methylthio-4-(trifluoromethyl)benzoate as residue. The aqueous phase from the extractive work-up was acidified with dilute hydrochloric acid and extracted with ethyl acetate. The organic phase was dried and the filtrate was freed from the solvent. This gave an additional 3.80 g of methyl 2-methoxy-3-methylthio-4-(trifluoromethyl)benzoate as residue.

Step 5: Synthesis of 2-methoxy-3-methylthio-4-(trifluoromethyl)benzoic acid (Table Example No. 12-13)

16 ml of 20 percent strength aqueous sodium hydroxide solution were added to 16.0 g (57.1 mmol) of methyl 2-methoxy-3-methylthio-4-(trifluoromethyl)benzoate in 160 ml of methanol, and the mixture was stirred at RT for 4 h. For work-up, the mixture was freed from the solvent and the residue was taken up in a little water. The mixture was cooled in an ice bath and then acidified with dilute hydrochloric acid. The mixture was stirred at RT for 5 min, and the contents was then filtered. This gave 15.3 g of 2-methoxy-3-methylthio-4-(trifluoromethyl)benzoic acid.

Step 6: Synthesis of 3-(2-methoxy-3-methylthio-4-(trifluoromethyl)benzoyloxy)-cyclohex-2-enone 133 mg (1.05 mmol) of oxalyl dichloride and three drops of N,N-dimethylformamide were added in succession to 200 mg (purity 78% by weight, 0.59 mmol) of 2-methoxy-3-methylthio-4-(trifluoromethyl)benzoic acid in 20 ml of dichloromethane. After the elimination of gas had ceased, the mixture was heated under reflux for another 10 min. The content was then cooled to RT and freed from the solvent. 93 mg (0.83 mmol) of 1,3-cyclohexanedione were added to the residue in 20 ml of dry dichloromethane, and 152 mg (1.50 mmol) of triethylamine were then added dropwise. The mixture was stirred at RT for 16 h. For work-up, 3 ml of 1M hydrochloric acid were added to the contents. After phase separation, the organic phase was freed from the solvent. The residue was purified chromatographically, which isolated 100 mg of 3-(2-methoxy-3-methylthio-4-(trifluoromethyl)benzoyloxy)-cyclohex-2-enone.

Step 7: Synthesis of 3-(2-methoxy-3-methylsulfinyl-4-(trifluoromethyl)benzoyloxy)-cyclohex-2-enone 68 mg (70% by weight, 0.28 mmol) of meta-chloroperbenzoic acid were added to 100 mg (0.28 mmol) of 3-(2-methoxy-3-methylthio-4-(trifluoromethyl)benzoyloxy)-cyclohex-2-enone in 10 ml of dichloromethane. The mixture was stirred at RT for 1 h. For work-up, 3 ml of 10 percent strength aqueous sodium hydrogensulfite solution were added. After confirmation that no peroxides were present, the organic phase was washed twice with in each case 5 ml of saturated aqueous NaHCO$_3$ solution. After phase separation, the solvent was removed. This gave 90 mg of 3-(2-methoxy-3-methylsulfinyl-4-(trifluoromethyl)benzoyloxy)cyclohex-2-enone.

Step 8: Synthesis of 2-(2-methoxy-3-methylsulfinyl-4-(trifluoromethyl)benzoyl)-cyclohexane-1,3-dione (Table Example No. 1-17)

48 mg (0.48 mmol) of triethylamine and eight drops of trimethylsilyl cyanide were successively added to 90 mg (0.24 mmol) of 3-(2-methoxy-3-methylsulfinyl-4-(trifluoromethyl)benzoyloxy)cyclohex-2-enone in 15 ml of acetonitrile. The mixture was stirred at RT for 16 h. For work-up, the solvent was removed. The residue was taken up in 15 ml of dichloromethane, and 3 ml of 1 N hydrochloric acid were added. After phase separation, the solvent was removed and the residue was purified chromatographically, which gave 49.9 mg of 2-(2-methoxy-3-methylsulfinyl-4-(trifluoromethyl)benzoyl)cyclohexane-1,3-dione.

The examples listed in the tables below were prepared analogously to the methods mentioned above or can be obtained analogously to the methods mentioned above. These compounds are very particularly preferred.

The abbreviations used denote:

| Et = ethyl | Me = methyl | Pr = propyl | Ph = phenyl |
| --- | --- | --- | --- |

TABLE 1

Compounds of the formula (I) according to the invention in which $R^2$ is hydroxyl and $R^3$ to $R^8$ are each hydrogen.

(I)

| No. | X | $R^1$ | n | Y | Physical data: $^1$H-NMR: δ [CDCl$_3$] |
| --- | --- | --- | --- | --- | --- |
| 1-1 | OH | Me | 0 | CF$_3$ | |
| 1-2 | OH | Et | 0 | CF$_3$ | |
| 1-3 | OH | n-Pr | 0 | CF$_3$ | |
| 1-4 | OH | i-Pr | 0 | CF$_3$ | |
| 1-5 | OH | Me | 1 | CF$_3$ | |
| 1-6 | OH | Et | 1 | CF$_3$ | |
| 1-7 | OH | n-Pr | 1 | CF$_3$ | |
| 1-8 | OH | i-Pr | 1 | CF$_3$ | |
| 1-9 | OH | Me | 2 | CF$_3$ | |
| 1-10 | OH | Et | 2 | CF$_3$ | |
| 1-11 | OH | n-Pr | 2 | CF$_3$ | |
| 1-12 | OH | i-Pr | 2 | CF$_3$ | |
| 1-13 | OMe | Me | 0 | CF$_3$ | 16.93 (s, 1H), 7.49 (d, 1H), 7.18 (d, 1H), 3.86 (s, 3H), 2.78 (t, 2H), 2.43 (t, 2H), 2.42 (s, 3H), 2.06 (quint, 2H) |
| 1-14 | OMe | Et | 0 | CF$_3$ | |
| 1-15 | OMe | n-Pr | 0 | CF$_3$ | |
| 1-16 | OMe | i-Pr | 0 | CF$_3$ | |
| 1-17 | OMe | Me | 1 | CF$_3$ | 16.66 (s, 1H), 7.56 (d, 1H), 7.42 (d, 1H), 3.88 (s, 3H), 3.07 (s, 3H), 2.81 (m, 2H), 2.46 (m, 2H), 2.08 (m, 2H) |
| 1-18 | OMe | Et | 1 | CF$_3$ | |
| 1-19 | OMe | n-Pr | 1 | CF$_3$ | |
| 1-20 | OMe | i-Pr | 1 | CF$_3$ | |
| 1-21 | OMe | Me | 2 | CF$_3$ | 16.67 (s, 1H), 7.71 (d, 1H), 7.51 (d, 1H), 3.84 (s, 3H), 3.30 (s, 3H), 2.82 (t, 2H), 2.44 (t, 2H), 2.08 (quint, 2H) |
| 1-22 | OMe | Et | 2 | CF$_3$ | |
| 1-23 | OMe | n-Pr | 2 | CF$_3$ | |
| 1-24 | OMe | i-Pr | 2 | CF$_3$ | |
| 1-25 | OEt | Me | 0 | CF$_3$ | 16.82 (s, 1H), 7.47 (d, 1H), 7.22 (d, 1H), 4.03 (q, 2H), 2.76 (t, 2H), 2.46-2.41 (m, 5H), 2.06 (quint, 2H), 1.30 (t, 3H) |
| 1-26 | OEt | Et | 0 | CF$_3$ | |
| 1-27 | OEt | n-Pr | 0 | CF$_3$ | |
| 1-28 | OEt | i-Pr | 0 | CF$_3$ | |
| 1-29 | OEt | Me | 1 | CF$_3$ | 16.66 (s, 1H), 7.55 (d, 1H), 7.41 (d, 1H), 4.30 (m, 1H), 3.78 (m, 1H), 3.06 (s, 3H), 2.80 (m, 2H), 2.52 (m, 1H), 2.39 (m, 1H), 2.07 (m, 2H), 1.32 (t, 3H) |

TABLE 1-continued

Compounds of the formula (I) according to the invention in which $R^2$ is hydroxyl and $R^3$ to $R^8$ are each hydrogen.

(I)

| No. | X | $R^1$ | n | Y | Physical data: $^1$H-NMR: δ [CDCl$_3$] |
|---|---|---|---|---|---|
| 1-30 | OEt | Et | 1 | CF$_3$ | |
| 1-31 | OEt | n-Pr | 1 | CF$_3$ | |
| 1-32 | OEt | i-Pr | 1 | CF$_3$ | |
| 1-33 | OEt | Me | 2 | CF$_3$ | 16.63 (s, 1H), 7.71 (d, 1H), 7.51 (d, 1H), 4.01 (m, 2H), 3.32 (s, 3H), 2.81 (t, 2H), 2.44 (t, 2H), 2.07 (quint, 2H), 1.32 (t, 3H) |
| 1-34 | OEt | Et | 2 | CF$_3$ | |
| 1-35 | OEt | n-Pr | 2 | CF$_3$ | |
| 1-36 | OEt | i-Pr | 2 | CF$_3$ | |
| 1-37 | O—CH$_2$—c-Pr | Me | 0 | CF$_3$ | |
| 1-38 | O—CH$_2$—c-Pr | Et | 0 | CF$_3$ | |
| 1-39 | O—CH$_2$—c-Pr | n-Pr | 0 | CF$_3$ | |
| 1-40 | O—CH$_2$—c-Pr | i-Pr | 0 | CF$_3$ | |
| 1-41 | O—CH$_2$—c-Pr | Me | 1 | CF$_3$ | |
| 1-42 | O—CH$_2$—c-Pr | Et | 1 | CF$_3$ | |
| 1-43 | O—CH$_2$—c-Pr | n-Pr | 1 | CF$_3$ | |
| 1-44 | O—CH$_2$—c-Pr | i-Pr | 1 | CF$_3$ | |
| 1-45 | O—CH$_2$—c-Pr | Me | 2 | CF$_3$ | |
| 1-46 | O—CH$_2$—c-Pr | Et | 2 | CF$_3$ | |
| 1-47 | O—CH$_2$—c-Pr | n-Pr | 2 | CF$_3$ | |
| 1-48 | O—CH$_2$—c-Pr | i-Pr | 2 | CF$_3$ | |
| 1-49 | OCH$_2$CH$_2$OMe | Me | 0 | CF$_3$ | |
| 1-50 | OCH$_2$CH$_2$OMe | Et | 0 | CF$_3$ | |
| 1-51 | OCH$_2$CH$_2$OMe | n-Pr | 0 | CF$_3$ | |
| 1-52 | OCH$_2$CH$_2$OMe | i-Pr | 0 | CF$_3$ | |
| 1-53 | OCH$_2$CH$_2$OMe | Me | 1 | CF$_3$ | |
| 1-54 | OCH$_2$CH$_2$OMe | Et | 1 | CF$_3$ | |
| 1-55 | OCH$_2$CH$_2$OMe | n-Pr | 1 | CF$_3$ | |
| 1-56 | OCH$_2$CH$_2$OMe | i-Pr | 1 | CF$_3$ | |
| 1-57 | OCH$_2$CH$_2$OMe | Me | 2 | CF$_3$ | |
| 1-58 | OCH$_2$CH$_2$OMe | Et | 2 | CF$_3$ | |
| 1-59 | OCH$_2$CH$_2$OMe | n-Pr | 2 | CF$_3$ | |
| 1-60 | OCH$_2$CH$_2$OMe | i-Pr | 2 | CF$_3$ | |
| 1-61 | OCH$_2$CH$_2$SMe | Me | 0 | CF$_3$ | |
| 1-62 | OCH$_2$CH$_2$SMe | Et | 0 | CF$_3$ | |
| 1-63 | OCH$_2$CH$_2$SMe | n-Pr | 0 | CF$_3$ | |
| 1-64 | OCH$_2$CH$_2$SMe | i-Pr | 0 | CF$_3$ | |
| 1-65 | OCH$_2$CH$_2$SMe | Me | 1 | CF$_3$ | |
| 1-66 | OCH$_2$CH$_2$SMe | Et | 1 | CF$_3$ | |
| 1-67 | OCH$_2$CH$_2$SMe | n-Pr | 1 | CF$_3$ | |
| 1-68 | OCH$_2$CH$_2$SMe | i-Pr | 1 | CF$_3$ | |
| 1-69 | OCH$_2$CH$_2$SMe | Me | 2 | CF$_3$ | |
| 1-70 | OCH$_2$CH$_2$SMe | Et | 2 | CF$_3$ | |
| 1-71 | OCH$_2$CH$_2$SMe | n-Pr | 2 | CF$_3$ | |
| 1-72 | OCH$_2$CH$_2$SMe | i-Pr | 2 | CF$_3$ | |
| 1-73 | OCH$_2$CH$_2$SO$_2$Me | Me | 0 | CF$_3$ | |
| 1-74 | OCH$_2$CH$_2$SO$_2$Me | Et | 0 | CF$_3$ | |
| 1-75 | OCH$_2$CH$_2$SO$_2$Me | n-Pr | 0 | CF$_3$ | |
| 1-76 | OCH$_2$CH$_2$SO$_2$Me | i-Pr | 0 | CF$_3$ | |
| 1-77 | OCH$_2$CH$_2$SO$_2$Me | Me | 1 | CF$_3$ | |
| 1-78 | OCH$_2$CH$_2$SO$_2$Me | Et | 1 | CF$_3$ | |
| 1-79 | OCH$_2$CH$_2$SO$_2$Me | n-Pr | 1 | CF$_3$ | |
| 1-80 | OCH$_2$CH$_2$SO$_2$Me | i-Pr | 1 | CF$_3$ | |
| 1-81 | OCH$_2$CH$_2$SO$_2$Me | Me | 2 | CF$_3$ | |
| 1-82 | OCH$_2$CH$_2$SO$_2$Me | Et | 2 | CF$_3$ | |
| 1-83 | OCH$_2$CH$_2$SO$_2$Me | n-Pr | 2 | CF$_3$ | |
| 1-84 | OCH$_2$CH$_2$SO$_2$Me | i-Pr | 2 | CF$_3$ | |
| 1-85 | OCOMe | Me | 0 | CF$_3$ | |
| 1-86 | OCOMe | Et | 0 | CF$_3$ | |
| 1-87 | OCOMe | n-Pr | 0 | CF$_3$ | |
| 1-88 | OCOMe | i-Pr | 0 | CF$_3$ | |
| 1-89 | OCOMe | Me | 1 | CF$_3$ | |
| 1-90 | OCOMe | Et | 1 | CF$_3$ | |
| 1-91 | OCOMe | n-Pr | 1 | CF$_3$ | |

TABLE 1-continued

Compounds of the formula (I) according to the invention in which $R^2$ is hydroxyl and $R^3$ to $R^8$ are each hydrogen.

(I)

| No. | X | $R^1$ | n | Y | Physical data: $^1$H-NMR: δ [CDCl$_3$] |
|---|---|---|---|---|---|
| 1-92 | OCOMe | i-Pr | 1 | CF$_3$ | |
| 1-93 | OCOMe | Me | 2 | CF$_3$ | |
| 1-94 | OCOMe | Et | 2 | CF$_3$ | |
| 1-95 | OCOMe | n-Pr | 2 | CF$_3$ | |
| 1-96 | OCOMe | i-Pr | 2 | CF$_3$ | |
| 1-97 | OSO$_2$Me | Me | 0 | CF$_3$ | |
| 1-98 | OSO$_2$Me | Et | 0 | CF$_3$ | |
| 1-99 | OSO$_2$Me | n-Pr | 0 | CF$_3$ | |
| 1-100 | OSO$_2$Me | i-Pr | 0 | CF$_3$ | |
| 1-101 | OSO$_2$Me | Me | 1 | CF$_3$ | |
| 1-102 | OSO$_2$Me | Et | 1 | CF$_3$ | |
| 1-103 | OSO$_2$Me | n-Pr | 1 | CF$_3$ | |
| 1-104 | OSO$_2$Me | i-Pr | 1 | CF$_3$ | |
| 1-105 | OSO$_2$Me | Me | 2 | CF$_3$ | |
| 1-106 | OSO$_2$Me | Et | 2 | CF$_3$ | |
| 1-107 | OSO$_2$Me | n-Pr | 2 | CF$_3$ | |
| 1-108 | OSO$_2$Me | i-Pr | 2 | CF$_3$ | |
| 1-109 | OMe | Me | 0 | C$_2$F$_5$ | |
| 1-110 | OMe | Et | 0 | C$_2$F$_5$ | |
| 1-111 | OMe | n-Pr | 0 | C$_2$F$_5$ | |
| 1-112 | OMe | i-Pr | 0 | C$_2$F$_5$ | |
| 1-113 | OMe | Me | 1 | C$_2$F$_5$ | |
| 1-114 | OMe | Et | 1 | C$_2$F$_5$ | |
| 1-115 | OMe | n-Pr | 1 | C$_2$F$_5$ | |
| 1-116 | OMe | i-Pr | 1 | C$_2$F$_5$ | |
| 1-117 | OMe | Me | 2 | C$_2$F$_5$ | |
| 1-118 | OMe | Et | 2 | C$_2$F$_5$ | |
| 1-119 | OMe | n-Pr | 2 | C$_2$F$_5$ | |
| 1-120 | OMe | i-Pr | 2 | C$_2$F$_5$ | |
| 1-121 | OEt | Me | 0 | C$_2$F$_5$ | |
| 1-122 | OEt | Et | 0 | C$_2$F$_5$ | |
| 1-123 | OEt | n-Pr | 0 | C$_2$F$_5$ | |
| 1-124 | OEt | i-Pr | 0 | C$_2$F$_5$ | |
| 1-125 | OEt | Me | 1 | C$_2$F$_5$ | |
| 1-126 | OEt | Et | 1 | C$_2$F$_5$ | |
| 1-127 | OEt | n-Pr | 1 | C$_2$F$_5$ | |
| 1-128 | OEt | i-Pr | 1 | C$_2$F$_5$ | |
| 1-129 | OEt | Me | 2 | C$_2$F$_5$ | |
| 1-130 | OEt | Et | 2 | C$_2$F$_5$ | |
| 1-131 | OEt | n-Pr | 2 | C$_2$F$_5$ | |
| 1-132 | OEt | i-Pr | 2 | C$_2$F$_5$ | |
| 1-133 | O—CH$_2$—c-Pr | Me | 0 | C$_2$F$_5$ | |
| 1-134 | O—CH$_2$—c-Pr | Et | 0 | C$_2$F$_5$ | |
| 1-135 | O—CH$_2$—c-Pr | n-Pr | 0 | C$_2$F$_5$ | |
| 1-136 | O—CH$_2$—c-Pr | i-Pr | 0 | C$_2$F$_5$ | |
| 1-137 | O—CH$_2$—c-Pr | Me | 1 | C$_2$F$_5$ | |
| 1-138 | O—CH$_2$—c-Pr | Et | 1 | C$_2$F$_5$ | |
| 1-139 | O—CH$_2$—c-Pr | n-Pr | 1 | C$_2$F$_5$ | |
| 1-140 | O—CH$_2$—c-Pr | i-Pr | 1 | C$_2$F$_5$ | |
| 1-141 | O—CH$_2$—c-Pr | Me | 2 | C$_2$F$_5$ | |
| 1-142 | O—CH$_2$—c-Pr | Et | 2 | C$_2$F$_5$ | |
| 1-143 | O—CH$_2$—c-Pr | n-Pr | 2 | C$_2$F$_5$ | |
| 1-144 | O—CH$_2$—c-Pr | i-Pr | 2 | C$_2$F$_5$ | |
| 1-145 | OCH$_2$CH$_2$OMe | Me | 0 | C$_2$F$_5$ | |
| 1-146 | OCH$_2$CH$_2$OMe | Et | 0 | C$_2$F$_5$ | |
| 1-147 | OCH$_2$CH$_2$OMe | n-Pr | 0 | C$_2$F$_5$ | |
| 1-148 | OCH$_2$CH$_2$OMe | i-Pr | 0 | C$_2$F$_5$ | |
| 1-149 | OCH$_2$CH$_2$OMe | Me | 1 | C$_2$F$_5$ | |
| 1-150 | OCH$_2$CH$_2$OMe | Et | 1 | C$_2$F$_5$ | |
| 1-151 | OCH$_2$CH$_2$OMe | n-Pr | 1 | C$_2$F$_5$ | |
| 1-152 | OCH$_2$CH$_2$OMe | i-Pr | 1 | C$_2$F$_5$ | |
| 1-153 | OCH$_2$CH$_2$OMe | Me | 2 | C$_2$F$_5$ | |
| 1-154 | OCH$_2$CH$_2$OMe | Et | 2 | C$_2$F$_5$ | |
| 1-155 | OCH$_2$CH$_2$OMe | n-Pr | 2 | C$_2$F$_5$ | |
| 1-156 | OCH$_2$CH$_2$OMe | i-Pr | 2 | C$_2$F$_5$ | |

TABLE 1-continued

Compounds of the formula (I) according to the invention in which $R^2$ is hydroxyl and $R^3$ to $R^8$ are each hydrogen.

$$\text{(I)}$$

| No. | X | $R^1$ | n | Y | Physical data: $^1$H-NMR: δ [CDCl$_3$] |
|---|---|---|---|---|---|
| 1-157 | OCH$_2$CH$_2$SMe | Me | 0 | C$_2$F$_5$ | |
| 1-158 | OCH$_2$CH$_2$SMe | Et | 0 | C$_2$F$_5$ | |
| 1-159 | OCH$_2$CH$_2$SMe | n-Pr | 0 | C$_2$F$_5$ | |
| 1-160 | OCH$_2$CH$_2$SMe | i-Pr | 0 | C$_2$F$_5$ | |
| 1-161 | OCH$_2$CH$_2$SMe | Me | 1 | C$_2$F$_5$ | |
| 1-162 | OCH$_2$CH$_2$SMe | Et | 1 | C$_2$F$_5$ | |
| 1-163 | OCH$_2$CH$_2$SMe | n-Pr | 1 | C$_2$F$_5$ | |
| 1-164 | OCH$_2$CH$_2$SMe | i-Pr | 1 | C$_2$F$_5$ | |
| 1-165 | OCH$_2$CH$_2$SMe | Me | 2 | C$_2$F$_5$ | |
| 1-166 | OCH$_2$CH$_2$SMe | Et | 2 | C$_2$F$_5$ | |
| 1-167 | OCH$_2$CH$_2$SMe | n-Pr | 2 | C$_2$F$_5$ | |
| 1-168 | OCH$_2$CH$_2$SMe | i-Pr | 2 | C$_2$F$_5$ | |
| 1-169 | OCH$_2$CH$_2$SO$_2$Me | Me | 0 | C$_2$F$_5$ | |
| 1-170 | OCH$_2$CH$_2$SO$_2$Me | Et | 0 | C$_2$F$_5$ | |
| 1-171 | OCH$_2$CH$_2$SO$_2$Me | n-Pr | 0 | C$_2$F$_5$ | |
| 1-172 | OCH$_2$CH$_2$SO$_2$Me | i-Pr | 0 | C$_2$F$_5$ | |
| 1-173 | OCH$_2$CH$_2$SO$_2$Me | Me | 1 | C$_2$F$_5$ | |
| 1-174 | OCH$_2$CH$_2$SO$_2$Me | Et | 1 | C$_2$F$_5$ | |
| 1-175 | OCH$_2$CH$_2$SO$_2$Me | n-Pr | 1 | C$_2$F$_5$ | |
| 1-176 | OCH$_2$CH$_2$SO$_2$Me | i-Pr | 1 | C$_2$F$_5$ | |
| 1-177 | OCH$_2$CH$_2$SO$_2$Me | Me | 2 | C$_2$F$_5$ | |
| 1-178 | OCH$_2$CH$_2$SO$_2$Me | Et | 2 | C$_2$F$_5$ | |
| 1-179 | OCH$_2$CH$_2$SO$_2$Me | n-Pr | 2 | C$_2$F$_5$ | |
| 1-180 | OCH$_2$CH$_2$SO$_2$Me | i-Pr | 2 | C$_2$F$_5$ | |
| 1-181 | OMe | Me | 0 | CCl$_3$ | |
| 1-182 | OMe | Et | 0 | CCl$_3$ | |
| 1-183 | OMe | n-Pr | 0 | CCl$_3$ | |
| 1-184 | OMe | i-Pr | 0 | CCl$_3$ | |
| 1-185 | OMe | Me | 1 | CCl$_3$ | |
| 1-186 | OMe | Et | 1 | CCl$_3$ | |
| 1-187 | OMe | n-Pr | 1 | CCl$_3$ | |
| 1-188 | OMe | i-Pr | 1 | CCl$_3$ | |
| 1-189 | OMe | Me | 2 | CCl$_3$ | |
| 1-190 | OMe | Et | 2 | CCl$_3$ | |
| 1-191 | OMe | n-Pr | 2 | CCl$_3$ | |
| 1-192 | OMe | i-Pr | 2 | CCl$_3$ | |
| 1-193 | OEt | Me | 0 | CCl$_3$ | |
| 1-194 | OEt | Et | 0 | CCl$_3$ | |
| 1-195 | OEt | n-Pr | 0 | CCl$_3$ | |
| 1-196 | OEt | i-Pr | 0 | CCl$_3$ | |
| 1-197 | OEt | Me | 1 | CCl$_3$ | |
| 1-198 | OEt | Et | 1 | CCl$_3$ | |
| 1-199 | OEt | n-Pr | 1 | CCl$_3$ | |
| 1-200 | OEt | i-Pr | 1 | CCl$_3$ | |
| 1-201 | OEt | Me | 2 | CCl$_3$ | |
| 1-202 | OEt | Et | 2 | CCl$_3$ | |
| 1-203 | OEt | n-Pr | 2 | CCl$_3$ | |
| 1-204 | OEt | i-Pr | 2 | CCl$_3$ | |
| 1-205 | O—CH$_2$—c-Pr | Me | 0 | CCl$_3$ | |
| 1-206 | O—CH$_2$—c-Pr | Et | 0 | CCl$_3$ | |
| 1-207 | O—CH$_2$—c-Pr | n-Pr | 0 | CCl$_3$ | |
| 1-208 | O—CH$_2$—c-Pr | i-Pr | 0 | CCl$_3$ | |
| 1-209 | O—CH$_2$—c-Pr | Me | 1 | CCl$_3$ | |
| 1-210 | O—CH$_2$—c-Pr | Et | 1 | CCl$_3$ | |
| 1-211 | O—CH$_2$—c-Pr | n-Pr | 1 | CCl$_3$ | |
| 1-212 | O—CH$_2$—c-Pr | i-Pr | 1 | CCl$_3$ | |
| 1-213 | O—CH$_2$—c-Pr | Me | 2 | CCl$_3$ | |
| 1-214 | O—CH$_2$—c-Pr | Et | 2 | CCl$_3$ | |
| 1-215 | O—CH$_2$—c-Pr | n-Pr | 2 | CCl$_3$ | |
| 1-216 | O—CH$_2$—c-Pr | i-Pr | 2 | CCl$_3$ | |
| 1-217 | OCH$_2$CH$_2$OMe | Me | 0 | CCl$_3$ | |
| 1-218 | OCH$_2$CH$_2$OMe | Et | 0 | CCl$_3$ | |
| 1-219 | OCH$_2$CH$_2$OMe | n-Pr | 0 | CCl$_3$ | |
| 1-220 | OCH$_2$CH$_2$OMe | i-Pr | 0 | CCl$_3$ | |
| 1-221 | OCH$_2$CH$_2$OMe | Me | 1 | CCl$_3$ | |

TABLE 1-continued

Compounds of the formula (I) according to the invention in which $R^2$ is hydroxyl and $R^3$ to $R^8$ are each hydrogen.

$$\text{(I)}$$

| No. | X | $R^1$ | n | Y | Physical data: $^1$H-NMR: δ [CDCl$_3$] |
|---|---|---|---|---|---|
| 1-222 | OCH$_2$CH$_2$OMe | Et | 1 | CCl$_3$ | |
| 1-223 | OCH$_2$CH$_2$OMe | n-Pr | 1 | CCl$_3$ | |
| 1-224 | OCH$_2$CH$_2$OMe | i-Pr | 1 | CCl$_3$ | |
| 1-225 | OCH$_2$CH$_2$OMe | Me | 2 | CCl$_3$ | |
| 1-226 | OCH$_2$CH$_2$OMe | Et | 2 | CCl$_3$ | |
| 1-227 | OCH$_2$CH$_2$OMe | n-Pr | 2 | CCl$_3$ | |
| 1-228 | OCH$_2$CH$_2$OMe | i-Pr | 2 | CCl$_3$ | |
| 1-229 | OCH$_2$CH$_2$SMe | Me | 0 | CCl$_3$ | |
| 1-230 | OCH$_2$CH$_2$SMe | Et | 0 | CCl$_3$ | |
| 1-231 | OCH$_2$CH$_2$SMe | n-Pr | 0 | CCl$_3$ | |
| 1-232 | OCH$_2$CH$_2$SMe | i-Pr | 0 | CCl$_3$ | |
| 1-233 | OCH$_2$CH$_2$SMe | Me | 1 | CCl$_3$ | |
| 1-234 | OCH$_2$CH$_2$SMe | Et | 1 | CCl$_3$ | |
| 1-235 | OCH$_2$CH$_2$SMe | n-Pr | 1 | CCl$_3$ | |
| 1-236 | OCH$_2$CH$_2$SMe | i-Pr | 1 | CCl$_3$ | |
| 1-237 | OCH$_2$CH$_2$SMe | Me | 2 | CCl$_3$ | |
| 1-238 | OCH$_2$CH$_2$SMe | Et | 2 | CCl$_3$ | |
| 1-239 | OCH$_2$CH$_2$SMe | n-Pr | 2 | CCl$_3$ | |
| 1-240 | OCH$_2$CH$_2$SMe | i-Pr | 2 | CCl$_3$ | |
| 1-241 | OCH$_2$CH$_2$SO$_2$Me | Me | 0 | CCl$_3$ | |
| 1-242 | OCH$_2$CH$_2$SO$_2$Me | Et | 0 | CCl$_3$ | |
| 1-243 | OCH$_2$CH$_2$SO$_2$Me | n-Pr | 0 | CCl$_3$ | |
| 1-244 | OCH$_2$CH$_2$SO$_2$Me | i-Pr | 0 | CCl$_3$ | |
| 1-245 | OCH$_2$CH$_2$SO$_2$Me | Me | 1 | CCl$_3$ | |
| 1-246 | OCH$_2$CH$_2$SO$_2$Me | Et | 1 | CCl$_3$ | |
| 1-247 | OCH$_2$CH$_2$SO$_2$Me | n-Pr | 1 | CCl$_3$ | |
| 1-248 | OCH$_2$CH$_2$SO$_2$Me | i-Pr | 1 | CCl$_3$ | |
| 1-249 | OCH$_2$CH$_2$SO$_2$Me | Me | 2 | CCl$_3$ | |
| 1-250 | OCH$_2$CH$_2$SO$_2$Me | Et | 2 | CCl$_3$ | |
| 1-251 | OCH$_2$CH$_2$SO$_2$Me | n-Pr | 2 | CCl$_3$ | |
| 1-252 | OCH$_2$CH$_2$SO$_2$Me | i-Pr | 2 | CCl$_3$ | |
| 1-253 | OMe | Me | 0 | CHF2 | |
| 1-254 | OMe | Et | 0 | CHF2 | |
| 1-255 | OMe | n-Pr | 0 | CHF2 | |
| 1-256 | OMe | i-Pr | 0 | CHF2 | |
| 1-257 | OMe | Me | 1 | CHF2 | |
| 1-258 | OMe | Et | 1 | CHF2 | |
| 1-259 | OMe | n-Pr | 1 | CHF2 | |
| 1-260 | OMe | i-Pr | 1 | CHF2 | |
| 1-261 | OMe | Me | 2 | CHF2 | |
| 1-262 | OMe | Et | 2 | CHF2 | |
| 1-263 | OMe | n-Pr | 2 | CHF2 | |
| 1-264 | OMe | i-Pr | 2 | CHF2 | |
| 1-265 | OEt | Me | 0 | CHF2 | |
| 1-266 | OEt | Et | 0 | CHF2 | |
| 1-267 | OEt | n-Pr | 0 | CHF2 | |
| 1-268 | OEt | i-Pr | 0 | CHF2 | |
| 1-269 | OEt | Me | 1 | CHF2 | |
| 1-270 | OEt | Et | 1 | CHF2 | |
| 1-271 | OEt | n-Pr | 1 | CHF2 | |
| 1-272 | OEt | i-Pr | 1 | CHF2 | |
| 1-273 | OEt | Me | 2 | CHF2 | |
| 1-274 | OEt | Et | 2 | CHF2 | |
| 1-275 | OEt | n-Pr | 2 | CHF2 | |
| 1-276 | OEt | i-Pr | 2 | CHF2 | |
| 1-277 | O—CH$_2$—c-Pr | Me | 0 | CHF2 | |
| 1-278 | O—CH$_2$—c-Pr | Et | 0 | CHF2 | |
| 1-279 | O—CH$_2$—c-Pr | n-Pr | 0 | CHF2 | |
| 1-280 | O—CH$_2$—c-Pr | i-Pr | 0 | CHF2 | |
| 1-281 | O—CH$_2$—c-Pr | Me | 1 | CHF2 | |
| 1-282 | O—CH$_2$—c-Pr | Et | 1 | CHF2 | |
| 1-283 | O—CH$_2$—c-Pr | n-Pr | 1 | CHF2 | |
| 1-284 | O—CH$_2$—c-Pr | i-Pr | 1 | CHF2 | |
| 1-285 | O—CH$_2$—c-Pr | Me | 2 | CHF2 | |
| 1-286 | O—CH$_2$—c-Pr | Et | 2 | CHF2 | |

TABLE 1-continued

Compounds of the formula (I) according to the invention in which $R^2$ is hydroxyl and $R^3$ to $R^8$ are each hydrogen.

(I)

| No. | X | $R^1$ | n | Y | Physical data: $^1$H-NMR: δ [CDCl$_3$] |
|---|---|---|---|---|---|
| 1-287 | O—CH$_2$—c-Pr | n-Pr | 2 | CHF2 | |
| 1-288 | O—CH$_2$—c-Pr | i-Pr | 2 | CHF2 | |
| 1-289 | OCH$_2$CH$_2$OMe | Me | 0 | CHF2 | |
| 1-290 | OCH$_2$CH$_2$OMe | Et | 0 | CHF2 | |
| 1-291 | OCH$_2$CH$_2$OMe | n-Pr | 0 | CHF2 | |
| 1-292 | OCH$_2$CH$_2$OMe | i-Pr | 0 | CHF2 | |
| 1-293 | OCH$_2$CH$_2$OMe | Me | 1 | CHF2 | |
| 1-294 | OCH$_2$CH$_2$OMe | Et | 1 | CHF2 | |
| 1-295 | OCH$_2$CH$_2$OMe | n-Pr | 1 | CHF2 | |
| 1-296 | OCH$_2$CH$_2$OMe | i-Pr | 1 | CHF2 | |
| 1-297 | OCH$_2$CH$_2$OMe | Me | 2 | CHF2 | |
| 1-298 | OCH$_2$CH$_2$OMe | Et | 2 | CHF2 | |
| 1-299 | OCH$_2$CH$_2$OMe | n-Pr | 2 | CHF2 | |
| 1-300 | OCH$_2$CH$_2$OMe | i-Pr | 2 | CHF2 | |
| 1-301 | OCH$_2$CH$_2$SMe | Me | 0 | CHF2 | |
| 1-302 | OCH$_2$CH$_2$SMe | Et | 0 | CHF2 | |
| 1-303 | OCH$_2$CH$_2$SMe | n-Pr | 0 | CHF2 | |
| 1-304 | OCH$_2$CH$_2$SMe | i-Pr | 0 | CHF2 | |
| 1-305 | OCH$_2$CH$_2$SMe | Me | 1 | CHF2 | |
| 1-306 | OCH$_2$CH$_2$SMe | Et | 1 | CHF2 | |
| 1-307 | OCH$_2$CH$_2$SMe | n-Pr | 1 | CHF2 | |
| 1-308 | OCH$_2$CH$_2$SMe | i-Pr | 1 | CHF2 | |
| 1-309 | OCH$_2$CH$_2$SMe | Me | 2 | CHF2 | |
| 1-310 | OCH$_2$CH$_2$SMe | Et | 2 | CHF2 | |
| 1-311 | OCH$_2$CH$_2$SMe | n-Pr | 2 | CHF2 | |
| 1-312 | OCH$_2$CH$_2$SMe | i-Pr | 2 | CHF2 | |
| 1-313 | OCH$_2$CH$_2$SO$_2$Me | Me | 0 | CHF2 | |
| 1-314 | OCH$_2$CH$_2$SO$_2$Me | Et | 0 | CHF2 | |
| 1-315 | OCH$_2$CH$_2$SO$_2$Me | n-Pr | 0 | CHF2 | |
| 1-316 | OCH$_2$CH$_2$SO$_2$Me | i-Pr | 0 | CHF2 | |
| 1-317 | OCH$_2$CH$_2$SO$_2$Me | Me | 1 | CHF2 | |
| 1-318 | OCH$_2$CH$_2$SO$_2$Me | Et | 1 | CHF2 | |
| 1-319 | OCH$_2$CH$_2$SO$_2$Me | n-Pr | 1 | CHF2 | |
| 1-320 | OCH$_2$CH$_2$SO$_2$Me | i-Pr | 1 | CHF2 | |
| 1-321 | OCH$_2$CH$_2$SO$_2$Me | Me | 2 | CHF2 | |
| 1-322 | OCH$_2$CH$_2$SO$_2$Me | Et | 2 | CHF2 | |
| 1-323 | OCH$_2$CH$_2$SO$_2$Me | n-Pr | 2 | CHF2 | |
| 1-324 | OCH$_2$CH$_2$SO$_2$Me | i-Pr | 2 | CHF2 | |
| 1-325 | OMe | Me | 0 | CF(CF$_3$)$_2$ | |
| 1-326 | OMe | Et | 0 | CF(CF$_3$)$_2$ | |
| 1-327 | OMe | n-Pr | 0 | CF(CF$_3$)$_2$ | |
| 1-328 | OMe | i-Pr | 0 | CF(CF$_3$)$_2$ | |
| 1-329 | OMe | Me | 1 | CF(CF$_3$)$_2$ | |
| 1-330 | OMe | Et | 1 | CF(CF$_3$)$_2$ | |
| 1-331 | OMe | n-Pr | 1 | CF(CF$_3$)$_2$ | |
| 1-332 | OMe | i-Pr | 1 | CF(CF$_3$)$_2$ | |
| 1-333 | OMe | Me | 2 | CF(CF$_3$)$_2$ | |
| 1-334 | OMe | Et | 2 | CF(CF$_3$)$_2$ | |
| 1-335 | OMe | n-Pr | 2 | CF(CF$_3$)$_2$ | |
| 1-336 | OMe | i-Pr | 2 | CF(CF$_3$)$_2$ | |
| 1-337 | OEt | Me | 0 | CF(CF$_3$)$_2$ | |
| 1-338 | OEt | Et | 0 | CF(CF$_3$)$_2$ | |
| 1-339 | OEt | n-Pr | 0 | CF(CF$_3$)$_2$ | |
| 1-340 | OEt | i-Pr | 0 | CF(CF$_3$)$_2$ | |
| 1-341 | OEt | Me | 1 | CF(CF$_3$)$_2$ | |
| 1-342 | OEt | Et | 1 | CF(CF$_3$)$_2$ | |
| 1-343 | OEt | n-Pr | 1 | CF(CF$_3$)$_2$ | |
| 1-344 | OEt | i-Pr | 1 | CF(CF$_3$)$_2$ | |

TABLE 1-continued

Compounds of the formula (I) according to the invention in which $R^2$ is hydroxyl and $R^3$ to $R^8$ are each hydrogen.

$$\text{(I)}$$

| No. | X | $R^1$ | n | Y | Physical data: $^1$H-NMR: δ [CDCl$_3$] |
|---|---|---|---|---|---|
| 1-345 | OEt | Me | 2 | CF(CF$_3$)$_2$ | |
| 1-346 | OEt | Et | 2 | CF(CF$_3$)$_2$ | |
| 1-347 | OEt | n-Pr | 2 | CF(CF$_3$)$_2$ | |
| 1-348 | OEt | i-Pr | 2 | CF(CF$_3$)$_2$ | |
| 1-349 | O—CH$_2$—c-Pr | Me | 0 | CF(CF$_3$)$_2$ | |
| 1-350 | O—CH$_2$—c-Pr | Et | 0 | CF(CF$_3$)$_2$ | |
| 1-351 | O—CH$_2$—c-Pr | n-Pr | 0 | CF(CF$_3$)$_2$ | |
| 1-352 | O—CH$_2$—c-Pr | i-Pr | 0 | CF(CF$_3$)$_2$ | |
| 1-353 | O—CH$_2$—c-Pr | Me | 1 | CF(CF$_3$)$_2$ | |
| 1-354 | O—CH$_2$—c-Pr | Et | 1 | CF(CF$_3$)$_2$ | |
| 1-355 | O—CH$_2$—c-Pr | n-Pr | 1 | CF(CF$_3$)$_2$ | |
| 1-356 | O—CH$_2$—c-Pr | i-Pr | 1 | CF(CF$_3$)$_2$ | |
| 1-357 | O—CH$_2$—c-Pr | Me | 2 | CF(CF$_3$)$_2$ | |
| 1-358 | O—CH$_2$—c-Pr | Et | 2 | CF(CF$_3$)$_2$ | |
| 1-359 | O—CH$_2$—c-Pr | n-Pr | 2 | CF(CF$_3$)$_2$ | |
| 1-360 | O—CH$_2$—c-Pr | i-Pr | 2 | CF(CF$_3$)$_2$ | |
| 1-361 | OCH$_2$CH$_2$OMe | Me | 0 | CF(CF$_3$)$_2$ | |
| 1-362 | OCH$_2$CH$_2$OMe | Et | 0 | CF(CF$_3$)$_2$ | |
| 1-363 | OCH$_2$CH$_2$OMe | n-Pr | 0 | CF(CF$_3$)$_2$ | |
| 1-364 | OCH$_2$CH$_2$OMe | i-Pr | 0 | CF(CF$_3$)$_2$ | |
| 1-365 | OCH$_2$CH$_2$OMe | Me | 1 | CF(CF$_3$)$_2$ | |
| 1-366 | OCH$_2$CH$_2$OMe | Et | 1 | CF(CF$_3$)$_2$ | |
| 1-367 | OCH$_2$CH$_2$OMe | n-Pr | 1 | CF(CF$_3$)$_2$ | |
| 1-368 | OCH$_2$CH$_2$OMe | i-Pr | 1 | CF(CF$_3$)$_2$ | |
| 1-369 | OCH$_2$CH$_2$OMe | Me | 2 | CF(CF$_3$)$_2$ | |
| 1-370 | OCH$_2$CH$_2$OMe | Et | 2 | CF(CF$_3$)$_2$ | |
| 1-371 | OCH$_2$CH$_2$OMe | n-Pr | 2 | CF(CF$_3$)$_2$ | |
| 1-372 | OCH$_2$CH$_2$OMe | i-Pr | 2 | CF(CF$_3$)$_2$ | |
| 1-373 | OCH$_2$CH$_2$SMe | Me | 0 | CF(CF$_3$)$_2$ | |
| 1-374 | OCH$_2$CH$_2$SMe | Et | 0 | CF(CF$_3$)$_2$ | |
| 1-375 | OCH$_2$CH$_2$SMe | n-Pr | 0 | CF(CF$_3$)$_2$ | |
| 1-376 | OCH$_2$CH$_2$SMe | i-Pr | 0 | CF(CF$_3$)$_2$ | |
| 1-377 | OCH$_2$CH$_2$SMe | Me | 1 | CF(CF$_3$)$_2$ | |
| 1-378 | OCH$_2$CH$_2$SMe | Et | 1 | CF(CF$_3$)$_2$ | |
| 1-379 | OCH$_2$CH$_2$SMe | n-Pr | 1 | CF(CF$_3$)$_2$ | |
| 1-380 | OCH$_2$CH$_2$SMe | i-Pr | 1 | CF(CF$_3$)$_2$ | |
| 1-381 | OCH$_2$CH$_2$SMe | Me | 2 | CF(CF$_3$)$_2$ | |
| 1-382 | OCH$_2$CH$_2$SMe | Et | 2 | CF(CF$_3$)$_2$ | |
| 1-383 | OCH$_2$CH$_2$SMe | n-Pr | 2 | CF(CF$_3$)$_2$ | |
| 1-384 | OCH$_2$CH$_2$SMe | i-Pr | 2 | CF(CF$_3$)$_2$ | |
| 1-385 | OCH$_2$CH$_2$SO$_2$Me | Me | 0 | CF(CF$_3$)$_2$ | |
| 1-386 | OCH$_2$CH$_2$SO$_2$Me | Et | 0 | CF(CF$_3$)$_2$ | |
| 1-387 | OCH$_2$CH$_2$SO$_2$Me | n-Pr | 0 | CF(CF$_3$)$_2$ | |
| 1-388 | OCH$_2$CH$_2$SO$_2$Me | i-Pr | 0 | CF(CF$_3$)$_2$ | |
| 1-389 | OCH$_2$CH$_2$SO$_2$Me | Me | 1 | CF(CF$_3$)$_2$ | |
| 1-390 | OCH$_2$CH$_2$SO$_2$Me | Et | 1 | CF(CF$_3$)$_2$ | |
| 1-391 | OCH$_2$CH$_2$SO$_2$Me | n-Pr | 1 | CF(CF$_3$)$_2$ | |
| 1-392 | OCH$_2$CH$_2$SO$_2$Me | i-Pr | 1 | CF(CF$_3$)$_2$ | |
| 1-393 | OCH$_2$CH$_2$SO$_2$Me | Me | 2 | CF(CF$_3$)$_2$ | |
| 1-394 | OCH$_2$CH$_2$SO$_2$Me | Et | 2 | CF(CF$_3$)$_2$ | |
| 1-395 | OCH$_2$CH$_2$SO$_2$Me | n-Pr | 2 | CF(CF$_3$)$_2$ | |
| 1-396 | OCH$_2$CH$_2$SO$_2$Me | i-Pr | 2 | CF(CF$_3$)$_2$ | |

TABLE 2

Compounds of the formula (I) according to the invention in which $R^2$ is hydroxyl, $R^3$ to $R^6$ are each hydrogen and $R^7$ and $R^8$ are each methyl.

(I)

| No. | X | $R^1$ | n | Y | Physical data: $^1$H-NMR: δ [CDCl$_3$] |
|---|---|---|---|---|---|
| 2-1 | OH | Me | 0 | CF$_3$ | |
| 2-2 | OH | Et | 0 | CF$_3$ | |
| 2-3 | OH | n-Pr | 0 | CF$_3$ | |
| 2-4 | OH | i-Pr | 0 | CF$_3$ | |
| 2-5 | OH | Me | 1 | CF$_3$ | |
| 2-6 | OH | Et | 1 | CF$_3$ | |
| 2-7 | OH | n-Pr | 1 | CF$_3$ | |
| 2-8 | OH | i-Pr | 1 | CF$_3$ | |
| 2-9 | OH | Me | 2 | CF$_3$ | |
| 2-10 | OH | Et | 2 | CF$_3$ | |
| 2-11 | OH | n-Pr | 2 | CF$_3$ | |
| 2-12 | OH | i-Pr | 2 | CF$_3$ | |
| 2-13 | OMe | Me | 0 | CF$_3$ | 17.37/16.60 (s, 1H), 7.52-7.47 (d/d, 1H), 7.23-7.18 (m, 1H), 3.83/3.80 (s, 3H), 2.79/2.47 (t, 2H), 2.42/2.41 (s, 3H), 1.93-1.85 (m, 2H), 1.38/1.11 (s, 6H) |
| 2-14 | OMe | Et | 0 | CF$_3$ | |
| 2-15 | OMe | n-Pr | 0 | CF$_3$ | |
| 2-16 | OMe | i-Pr | 0 | CF$_3$ | |
| 2-17 | OMe | Me | 1 | CF$_3$ | 17.12/16.33 (s, 1H), 7.58/7.55 (d, 1H), 7.50-7.42 (m, 1H), 3.86/3.84 (s, 3H), 3.07/3.05 (s, 3H), 2.82/2.49 (m, 2H), 1.89 (m, 2H), 1.42/1.21 (s, 3H), 1.37/1.07 (s, 3H) |
| 2-18 | OMe | Et | 1 | CF$_3$ | |
| 2-19 | OMe | n-Pr | 1 | CF$_3$ | |
| 2-20 | OMe | i-Pr | 1 | CF$_3$ | |
| 2-21 | OMe | Me | 2 | CF$_3$ | 17.13/16.39 (s, 1H), 7.73/7.72 (d, 1H), 7.55/7.52 (d, 1H), 3.83/3.82 (s, 3H), 3.29/3.27 (s, 3H), 2.82/2.47 (t, 2H), 1.94-1.87 (m, 2H), 1.41/1.12 (s, 6H) |
| 2-22 | OMe | Et | 2 | CF$_3$ | |
| 2-23 | OMe | n-Pr | 2 | CF$_3$ | |
| 2-24 | OMe | i-Pr | 2 | CF$_3$ | |
| 2-25 | OEt | Me | 0 | CF$_3$ | |
| 2-26 | OEt | Et | 0 | CF$_3$ | |
| 2-27 | OEt | n-Pr | 0 | CF$_3$ | |
| 2-28 | OEt | i-Pr | 0 | CF$_3$ | |
| 2-29 | OEt | Me | 1 | CF$_3$ | |
| 2-30 | OEt | Et | 1 | CF$_3$ | |
| 2-31 | OEt | n-Pr | 1 | CF$_3$ | |
| 2-32 | OEt | i-Pr | 1 | CF$_3$ | |
| 2-33 | OEt | Me | 2 | CF$_3$ | |
| 2-34 | OEt | Et | 2 | CF$_3$ | |
| 2-35 | OEt | n-Pr | 2 | CF$_3$ | |
| 2-36 | OEt | i-Pr | 2 | CF$_3$ | |
| 2-37 | O—CH$_2$—c-Pr | Me | 0 | CF$_3$ | |
| 2-38 | O—CH$_2$—c-Pr | Et | 0 | CF$_3$ | |
| 2-39 | O—CH$_2$—c-Pr | n-Pr | 0 | CF$_3$ | |
| 2-40 | O—CH$_2$—c-Pr | i-Pr | 0 | CF$_3$ | |
| 2-41 | O—CH$_2$—c-Pr | Me | 1 | CF$_3$ | |
| 2-42 | O—CH$_2$—c-Pr | Et | 1 | CF$_3$ | |
| 2-43 | O—CH$_2$—c-Pr | n-Pr | 1 | CF$_3$ | |
| 2-44 | O—CH$_2$—c-Pr | i-Pr | 1 | CF$_3$ | |
| 2-45 | O—CH$_2$—c-Pr | Me | 2 | CF$_3$ | |
| 2-46 | O—CH$_2$—c-Pr | Et | 2 | CF$_3$ | |
| 2-47 | O—CH$_2$—c-Pr | n-Pr | 2 | CF$_3$ | |
| 2-48 | O—CH$_2$—c-Pr | i-Pr | 2 | CF$_3$ | |
| 2-49 | OCH$_2$CH$_2$OMe | Me | 0 | CF$_3$ | |
| 2-50 | OCH$_2$CH$_2$OMe | Et | 0 | CF$_3$ | |
| 2-51 | OCH$_2$CH$_2$OMe | n-Pr | 0 | CF$_3$ | |
| 2-52 | OCH$_2$CH$_2$OMe | i-Pr | 0 | CF$_3$ | |
| 2-53 | OCH$_2$CH$_2$OMe | Me | 1 | CF$_3$ | |
| 2-54 | OCH$_2$CH$_2$OMe | Et | 1 | CF$_3$ | |
| 2-55 | OCH$_2$CH$_2$OMe | n-Pr | 1 | CF$_3$ | |
| 2-56 | OCH$_2$CH$_2$OMe | i-Pr | 1 | CF$_3$ | |
| 2-57 | OCH$_2$CH$_2$OMe | Me | 2 | CF$_3$ | |
| 2-58 | OCH$_2$CH$_2$OMe | Et | 2 | CF$_3$ | |
| 2-59 | OCH$_2$CH$_2$OMe | n-Pr | 2 | CF$_3$ | |
| 2-60 | OCH$_2$CH$_2$OMe | i-Pr | 2 | CF$_3$ | |
| 2-61 | OCH$_2$CH$_2$SMe | Me | 0 | CF$_3$ | |
| 2-62 | OCH$_2$CH$_2$SMe | Et | 0 | CF$_3$ | |
| 2-63 | OCH$_2$CH$_2$SMe | n-Pr | 0 | CF$_3$ | |
| 2-64 | OCH$_2$CH$_2$SMe | i-Pr | 0 | CF$_3$ | |
| 2-65 | OCH$_2$CH$_2$SMe | Me | 1 | CF$_3$ | |
| 2-66 | OCH$_2$CH$_2$SMe | Et | 1 | CF$_3$ | |
| 2-67 | OCH$_2$CH$_2$SMe | n-Pr | 1 | CF$_3$ | |
| 2-68 | OCH$_2$CH$_2$SMe | i-Pr | 1 | CF$_3$ | |
| 2-69 | OCH$_2$CH$_2$SMe | Me | 2 | CF$_3$ | |
| 2-70 | OCH$_2$CH$_2$SMe | Et | 2 | CF$_3$ | |
| 2-71 | OCH$_2$CH$_2$SMe | n-Pr | 2 | CF$_3$ | |
| 2-72 | OCH$_2$CH$_2$SMe | i-Pr | 2 | CF$_3$ | |
| 2-73 | OCH$_2$CH$_2$SO$_2$Me | Me | 0 | CF$_3$ | |
| 2-74 | OCH$_2$CH$_2$SO$_2$Me | Et | 0 | CF$_3$ | |
| 2-75 | OCH$_2$CH$_2$SO$_2$Me | n-Pr | 0 | CF$_3$ | |
| 2-76 | OCH$_2$CH$_2$SO$_2$Me | i-Pr | 0 | CF$_3$ | |
| 2-77 | OCH$_2$CH$_2$SO$_2$Me | Me | 1 | CF$_3$ | |
| 2-78 | OCH$_2$CH$_2$SO$_2$Me | Et | 1 | CF$_3$ | |
| 2-79 | OCH$_2$CH$_2$SO$_2$Me | n-Pr | 1 | CF$_3$ | |
| 2-80 | OCH$_2$CH$_2$SO$_2$Me | i-Pr | 1 | CF$_3$ | |
| 2-81 | OCH$_2$CH$_2$SO$_2$Me | Me | 2 | CF$_3$ | |
| 2-82 | OCH$_2$CH$_2$SO$_2$Me | Et | 2 | CF$_3$ | |
| 2-83 | OCH$_2$CH$_2$SO$_2$Me | n-Pr | 2 | CF$_3$ | |
| 2-84 | OCH$_2$CH$_2$SO$_2$Me | i-Pr | 2 | CF$_3$ | |
| 2-85 | OCOMe | Me | 0 | CF$_3$ | |
| 2-86 | OCOMe | Et | 0 | CF$_3$ | |
| 2-87 | OCOMe | n-Pr | 0 | CF$_3$ | |
| 2-88 | OCOMe | i-Pr | 0 | CF$_3$ | |
| 2-89 | OCOMe | Me | 1 | CF$_3$ | |
| 2-90 | OCOMe | Et | 1 | CF$_3$ | |
| 2-91 | OCOMe | n-Pr | 1 | CF$_3$ | |
| 2-92 | OCOMe | i-Pr | 1 | CF$_3$ | |
| 2-93 | OCOMe | Me | 2 | CF$_3$ | |
| 2-94 | OCOMe | Et | 2 | CF$_3$ | |
| 2-95 | OCOMe | n-Pr | 2 | CF$_3$ | |
| 2-96 | OCOMe | i-Pr | 2 | CF$_3$ | |

TABLE 2-continued

Compounds of the formula (I) according to the invention in which $R^2$ is hydroxyl, $R^3$ to $R^6$ are each hydrogen and $R^7$ and $R^8$ are each methyl.

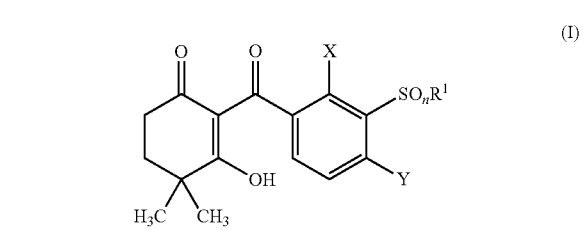

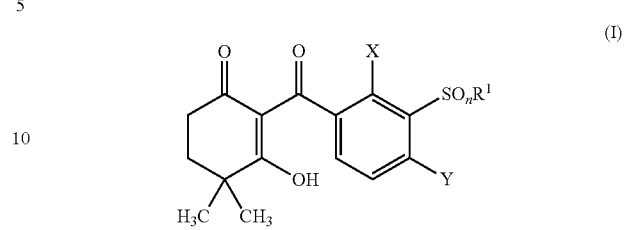

| No. | X | $R^1$ | n | Y | Physical data: $^1$H-NMR: δ [CDCl$_3$] |
|---|---|---|---|---|---|
| 2-97 | OSO$_2$Me | Me | 0 | CF$_3$ | |
| 2-98 | OSO$_2$Me | Et | 0 | CF$_3$ | |
| 2-99 | OSO$_2$Me | n-Pr | 0 | CF$_3$ | |
| 2-100 | OSO$_2$Me | i-Pr | 0 | CF$_3$ | |
| 2-101 | OSO$_2$Me | Me | 1 | CF$_3$ | |
| 2-102 | OSO$_2$Me | Et | 1 | CF$_3$ | |
| 2-103 | OSO$_2$Me | n-Pr | 1 | CF$_3$ | |
| 2-104 | OSO$_2$Me | i-Pr | 1 | CF$_3$ | |
| 2-105 | OSO$_2$Me | Me | 2 | CF$_3$ | |
| 2-106 | OSO$_2$Me | Et | 2 | CF$_3$ | |
| 2-107 | OSO$_2$Me | n-Pr | 2 | CF$_3$ | |
| 2-108 | OSO$_2$Me | i-Pr | 2 | CF$_3$ | |
| 2-109 | OMe | Me | 0 | C$_2$F$_5$ | |
| 2-110 | OMe | Et | 0 | C$_2$F$_5$ | |
| 2-111 | OMe | n-Pr | 0 | C$_2$F$_5$ | |
| 2-112 | OMe | i-Pr | 0 | C$_2$F$_5$ | |
| 2-113 | OMe | Me | 1 | C$_2$F$_5$ | |
| 2-114 | OMe | Et | 1 | C$_2$F$_5$ | |
| 2-115 | OMe | n-Pr | 1 | C$_2$F$_5$ | |
| 2-116 | OMe | i-Pr | 1 | C$_2$F$_5$ | |
| 2-117 | OMe | Me | 2 | C$_2$F$_5$ | |
| 2-118 | OMe | Et | 2 | C$_2$F$_5$ | |
| 2-119 | OMe | n-Pr | 2 | C$_2$F$_5$ | |
| 2-120 | OMe | i-Pr | 2 | C$_2$F$_5$ | |
| 2-121 | OEt | Me | 0 | C$_2$F$_5$ | |
| 2-122 | OEt | Et | 0 | C$_2$F$_5$ | |
| 2-123 | OEt | n-Pr | 0 | C$_2$F$_5$ | |
| 2-124 | OEt | i-Pr | 0 | C$_2$F$_5$ | |
| 2-125 | OEt | Me | 1 | C$_2$F$_5$ | |
| 2-126 | OEt | Et | 1 | C$_2$F$_5$ | |
| 2-127 | OEt | n-Pr | 1 | C$_2$F$_5$ | |
| 2-128 | OEt | i-Pr | 1 | C$_2$F$_5$ | |
| 2-129 | OEt | Me | 2 | C$_2$F$_5$ | |
| 2-130 | OEt | Et | 2 | C$_2$F$_5$ | |
| 2-131 | OEt | n-Pr | 2 | C$_2$F$_5$ | |
| 2-132 | OEt | i-Pr | 2 | C$_2$F$_5$ | |
| 2-133 | O—CH$_2$—c-Pr | Me | 0 | C$_2$F$_5$ | |
| 2-134 | O—CH$_2$—c-Pr | Et | 0 | C$_2$F$_5$ | |
| 2-135 | O—CH$_2$—c-Pr | n-Pr | 0 | C$_2$F$_5$ | |
| 2-136 | O—CH$_2$—c-Pr | i-Pr | 0 | C$_2$F$_5$ | |
| 2-137 | O—CH$_2$—c-Pr | Me | 1 | C$_2$F$_5$ | |
| 2-138 | O—CH$_2$—c-Pr | Et | 1 | C$_2$F$_5$ | |
| 2-139 | O—CH$_2$—c-Pr | n-Pr | 1 | C$_2$F$_5$ | |
| 2-140 | O—CH$_2$—c-Pr | i-Pr | 1 | C$_2$F$_5$ | |
| 2-141 | O—CH$_2$—c-Pr | Me | 2 | C$_2$F$_5$ | |
| 2-142 | O—CH$_2$—c-Pr | Et | 2 | C$_2$F$_5$ | |
| 2-143 | O—CH$_2$—c-Pr | n-Pr | 2 | C$_2$F$_5$ | |
| 2-144 | O—CH$_2$—c-Pr | i-Pr | 2 | C$_2$F$_5$ | |
| 2-145 | OCH$_2$CH$_2$OMe | Me | 0 | C$_2$F$_5$ | |
| 2-146 | OCH$_2$CH$_2$OMe | Et | 0 | C$_2$F$_5$ | |
| 2-147 | OCH$_2$CH$_2$OMe | n-Pr | 0 | C$_2$F$_5$ | |
| 2-148 | OCH$_2$CH$_2$OMe | i-Pr | 0 | C$_2$F$_5$ | |
| 2-149 | OCH$_2$CH$_2$OMe | Me | 1 | C$_2$F$_5$ | |
| 2-150 | OCH$_2$CH$_2$OMe | Et | 1 | C$_2$F$_5$ | |
| 2-151 | OCH$_2$CH$_2$OMe | n-Pr | 1 | C$_2$F$_5$ | |
| 2-152 | OCH$_2$CH$_2$OMe | i-Pr | 1 | C$_2$F$_5$ | |
| 2-153 | OCH$_2$CH$_2$OMe | Me | 2 | C$_2$F$_5$ | |
| 2-154 | OCH$_2$CH$_2$OMe | Et | 2 | C$_2$F$_5$ | |
| 2-155 | OCH$_2$CH$_2$OMe | n-Pr | 2 | C$_2$F$_5$ | |
| 2-156 | OCH$_2$CH$_2$OMe | i-Pr | 2 | C$_2$F$_5$ | |
| 2-157 | OCH$_2$CH$_2$SMe | Me | 0 | C$_2$F$_5$ | |
| 2-158 | OCH$_2$CH$_2$SMe | Et | 0 | C$_2$F$_5$ | |
| 2-159 | OCH$_2$CH$_2$SMe | n-Pr | 0 | C$_2$F$_5$ | |
| 2-160 | OCH$_2$CH$_2$SMe | i-Pr | 0 | C$_2$F$_5$ | |
| 2-161 | OCH$_2$CH$_2$SMe | Me | 1 | C$_2$F$_5$ | |
| 2-162 | OCH$_2$CH$_2$SMe | Et | 1 | C$_2$F$_5$ | |
| 2-163 | OCH$_2$CH$_2$SMe | n-Pr | 1 | C$_2$F$_5$ | |
| 2-164 | OCH$_2$CH$_2$SMe | i-Pr | 1 | C$_2$F$_5$ | |
| 2-165 | OCH$_2$CH$_2$SMe | Me | 2 | C$_2$F$_5$ | |
| 2-166 | OCH$_2$CH$_2$SMe | Et | 2 | C$_2$F$_5$ | |
| 2-167 | OCH$_2$CH$_2$SMe | n-Pr | 2 | C$_2$F$_5$ | |
| 2-168 | OCH$_2$CH$_2$SMe | i-Pr | 2 | C$_2$F$_5$ | |
| 2-169 | OCH$_2$CH$_2$SO$_2$Me | Me | 0 | C$_2$F$_5$ | |
| 2-170 | OCH$_2$CH$_2$SO$_2$Me | Et | 0 | C$_2$F$_5$ | |
| 2-171 | OCH$_2$CH$_2$SO$_2$Me | n-Pr | 0 | C$_2$F$_5$ | |
| 2-172 | OCH$_2$CH$_2$SO$_2$Me | i-Pr | 0 | C$_2$F$_5$ | |
| 2-173 | OCH$_2$CH$_2$SO$_2$Me | Me | 1 | C$_2$F$_5$ | |
| 2-174 | OCH$_2$CH$_2$SO$_2$Me | Et | 1 | C$_2$F$_5$ | |
| 2-175 | OCH$_2$CH$_2$SO$_2$Me | n-Pr | 1 | C$_2$F$_5$ | |
| 2-176 | OCH$_2$CH$_2$SO$_2$Me | i-Pr | 1 | C$_2$F$_5$ | |
| 2-177 | OCH$_2$CH$_2$SO$_2$Me | Me | 2 | C$_2$F$_5$ | |
| 2-178 | OCH$_2$CH$_2$SO$_2$Me | Et | 2 | C$_2$F$_5$ | |
| 2-179 | OCH$_2$CH$_2$SO$_2$Me | n-Pr | 2 | C$_2$F$_5$ | |
| 2-180 | OCH$_2$CH$_2$SO$_2$Me | i-Pr | 2 | C$_2$F$_5$ | |
| 2-181 | OMe | Me | 0 | CCl$_3$ | |
| 2-182 | OMe | Et | 0 | CCl$_3$ | |
| 2-183 | OMe | n-Pr | 0 | CCl$_3$ | |
| 2-184 | OMe | i-Pr | 0 | CCl$_3$ | |
| 2-185 | OMe | Me | 1 | CCl$_3$ | |
| 2-186 | OMe | Et | 1 | CCl$_3$ | |
| 2-187 | OMe | n-Pr | 1 | CCl$_3$ | |
| 2-188 | OMe | i-Pr | 1 | CCl$_3$ | |
| 2-189 | OMe | Me | 2 | CCl$_3$ | |
| 2-190 | OMe | Et | 2 | CCl$_3$ | |
| 2-191 | OMe | n-Pr | 2 | CCl$_3$ | |
| 2-192 | OMe | i-Pr | 2 | CCl$_3$ | |
| 2-193 | OEt | Me | 0 | CCl$_3$ | |
| 2-194 | OEt | Et | 0 | CCl$_3$ | |
| 2-195 | OEt | n-Pr | 0 | CCl$_3$ | |
| 2-196 | OEt | i-Pr | 0 | CCl$_3$ | |
| 2-197 | OEt | Me | 1 | CCl$_3$ | |
| 2-198 | OEt | Et | 1 | CCl$_3$ | |
| 2-199 | OEt | n-Pr | 1 | CCl$_3$ | |
| 2-200 | OEt | i-Pr | 1 | CCl$_3$ | |
| 2-201 | OEt | Me | 2 | CCl$_3$ | |
| 2-202 | OEt | Et | 2 | CCl$_3$ | |
| 2-203 | OEt | n-Pr | 2 | CCl$_3$ | |
| 2-204 | OEt | i-Pr | 2 | CCl$_3$ | |
| 2-205 | O—CH$_2$—c-Pr | Me | 0 | CCl$_3$ | |
| 2-206 | O—CH$_2$—c-Pr | Et | 0 | CCl$_3$ | |
| 2-207 | O—CH$_2$—c-Pr | n-Pr | 0 | CCl$_3$ | |
| 2-208 | O—CH$_2$—c-Pr | i-Pr | 0 | CCl$_3$ | |
| 2-209 | O—CH$_2$—c-Pr | Me | 1 | CCl$_3$ | |
| 2-210 | O—CH$_2$—c-Pr | Et | 1 | CCl$_3$ | |
| 2-211 | O—CH$_2$—c-Pr | n-Pr | 1 | CCl$_3$ | |
| 2-212 | O—CH$_2$—c-Pr | i-Pr | 1 | CCl$_3$ | |
| 2-213 | O—CH$_2$—c-Pr | Me | 2 | CCl$_3$ | |
| 2-214 | O—CH$_2$—c-Pr | Et | 2 | CCl$_3$ | |
| 2-215 | O—CH$_2$—c-Pr | n-Pr | 2 | CCl$_3$ | |
| 2-216 | O—CH$_2$—c-Pr | i-Pr | 2 | CCl$_3$ | |
| 2-217 | OCH$_2$CH$_2$OMe | Me | 0 | CCl$_3$ | |
| 2-218 | OCH$_2$CH$_2$OMe | Et | 0 | CCl$_3$ | |

TABLE 2-continued

Compounds of the formula (I) according to the invention in which $R^2$ is hydroxyl, $R^3$ to $R^6$ are each hydrogen and $R^7$ and $R^8$ are each methyl.

$$(I)$$

| No. | X | $R^1$ | n | Y | Physical data: $^1$H-NMR: δ [CDCl$_3$] |
|---|---|---|---|---|---|
| 2-219 | OCH$_2$CH$_2$OMe | n-Pr | 0 | CCl$_3$ | |
| 2-220 | OCH$_2$CH$_2$OMe | i-Pr | 0 | CCl$_3$ | |
| 2-221 | OCH$_2$CH$_2$OMe | Me | 1 | CCl$_3$ | |
| 2-222 | OCH$_2$CH$_2$OMe | Et | 1 | CCl$_3$ | |
| 2-223 | OCH$_2$CH$_2$OMe | n-Pr | 1 | CCl$_3$ | |
| 2-224 | OCH$_2$CH$_2$OMe | i-Pr | 1 | CCl$_3$ | |
| 2-225 | OCH$_2$CH$_2$OMe | Me | 2 | CCl$_3$ | |
| 2-226 | OCH$_2$CH$_2$OMe | Et | 2 | CCl$_3$ | |
| 2-227 | OCH$_2$CH$_2$OMe | n-Pr | 2 | CCl$_3$ | |
| 2-228 | OCH$_2$CH$_2$OMe | i-Pr | 2 | CCl$_3$ | |
| 2-229 | OCH$_2$CH$_2$SMe | Me | 0 | CCl$_3$ | |
| 2-230 | OCH$_2$CH$_2$SMe | Et | 0 | CCl$_3$ | |
| 2-231 | OCH$_2$CH$_2$SMe | n-Pr | 0 | CCl$_3$ | |
| 2-232 | OCH2CH2SMe | i-Pr | 0 | CCl$_3$ | |
| 2-233 | OCH$_2$CH$_2$SMe | Me | 1 | CCl$_3$ | |
| 2-234 | OCH$_2$CH$_2$SMe | Et | 1 | CCl$_3$ | |
| 2-235 | OCH$_2$CH$_2$SMe | n-Pr | 1 | CCl$_3$ | |
| 2-236 | OCH$_2$CH$_2$SMe | i-Pr | 1 | CCl$_3$ | |
| 2-237 | OCH$_2$CH$_2$SMe | Me | 2 | CCl$_3$ | |
| 2-238 | OCH$_2$CH$_2$SMe | Et | 2 | CCl$_3$ | |
| 2-239 | OCH$_2$CH$_2$SMe | n-Pr | 2 | CCl$_3$ | |
| 2-240 | OCH$_2$CH$_2$SMe | i-Pr | 2 | CCl$_3$ | |
| 2-241 | OCH$_2$CH$_2$SO$_2$Me | Me | 0 | CCl$_3$ | |
| 2-242 | OCH$_2$CH$_2$SO$_2$Me | Et | 0 | CCl$_3$ | |
| 2-243 | OCH$_2$CH$_2$SO$_2$Me | n-Pr | 0 | CCl$_3$ | |
| 2-244 | OCH$_2$CH$_2$SO$_2$Me | i-Pr | 0 | CCl$_3$ | |
| 2-245 | OCH$_2$CH$_2$SO$_2$Me | Me | 1 | CCl$_3$ | |
| 2-246 | OCH$_2$CH$_2$SO$_2$Me | Et | 1 | CCl$_3$ | |
| 2-247 | OCH$_2$CH$_2$SO$_2$Me | n-Pr | 1 | CCl$_3$ | |
| 2-248 | OCH$_2$CH$_2$SO$_2$Me | i-Pr | 1 | CCl$_3$ | |
| 2-249 | OCH$_2$CH$_2$SO$_2$Me | Me | 2 | CCl$_3$ | |
| 2-250 | OCH$_2$CH$_2$SO$_2$Me | Et | 2 | CCl$_3$ | |
| 2-251 | OCH$_2$CH$_2$SO$_2$Me | n-Pr | 2 | CCl$_3$ | |
| 2-252 | OCH$_2$CH$_2$SO$_2$Me | i-Pr | 2 | CCl$_3$ | |
| 2-253 | OMe | Me | 0 | CHF$_2$ | |
| 2-254 | OMe | Et | 0 | CHF$_2$ | |
| 2-255 | OMe | n-Pr | 0 | CHF$_2$ | |
| 2-256 | OMe | i-Pr | 0 | CHF$_2$ | |
| 2-257 | OMe | Me | 1 | CHF$_2$ | |
| 2-258 | OMe | Et | 1 | CHF$_2$ | |
| 2-259 | OMe | n-Pr | 1 | CHF$_2$ | |
| 2-260 | OMe | i-Pr | 1 | CHF$_2$ | |
| 2-261 | OMe | Me | 2 | CHF$_2$ | |
| 2-262 | OMe | Et | 2 | CHF$_2$ | |
| 2-263 | OMe | n-Pr | 2 | CHF$_2$ | |
| 2-264 | OMe | i-Pr | 2 | CHF$_2$ | |
| 2-265 | OEt | Me | 0 | CHF$_2$ | |
| 2-266 | OEt | Et | 0 | CHF$_2$ | |
| 2-267 | OEt | n-Pr | 0 | CHF$_2$ | |
| 2-268 | OEt | i-Pr | 0 | CHF$_2$ | |
| 2-269 | OEt | Me | 1 | CHF$_2$ | |
| 2-270 | OEt | Et | 1 | CHF$_2$ | |
| 2-271 | OEt | n-Pr | 1 | CHF$_2$ | |
| 2-272 | OEt | i-Pr | 1 | CHF$_2$ | |
| 2-273 | OEt | Me | 2 | CHF$_2$ | |
| 2-274 | OEt | Et | 2 | CHF$_2$ | |
| 2-275 | OEt | n-Pr | 2 | CHF$_2$ | |
| 2-276 | OEt | i-Pr | 2 | CHF$_2$ | |
| 2-277 | O—CH$_2$—c-Pr | Me | 0 | CHF$_2$ | |
| 2-278 | O—CH$_2$—c-Pr | Et | 0 | CHF$_2$ | |
| 2-279 | O—CH$_2$—c-Pr | n-Pr | 0 | CHF$_2$ | |
| 2-280 | O—CH$_2$—c-Pr | i-Pr | 0 | CHF$_2$ | |
| 2-281 | O—CH$_2$—c-Pr | Me | 1 | CHF$_2$ | |
| 2-282 | O—CH$_2$—c-Pr | Et | 1 | CHF$_2$ | |
| 2-283 | O—CH$_2$—c-Pr | n-Pr | 1 | CHF$_2$ | |
| 2-284 | O—CH$_2$—c-Pr | i-Pr | 1 | CHF$_2$ | |
| 2-285 | O—CH$_2$—c-Pr | Me | 2 | CHF$_2$ | |
| 2-286 | O—CH$_2$—c-Pr | Et | 2 | CHF$_2$ | |
| 2-287 | O—CH$_2$—c-Pr | n-Pr | 2 | CHF$_2$ | |
| 2-288 | O—CH$_2$—c-Pr | i-Pr | 2 | CHF$_2$ | |
| 2-289 | OCH$_2$CH$_2$OMe | Me | 0 | CHF$_2$ | |
| 2-290 | OCH$_2$CH$_2$OMe | Et | 0 | CHF$_2$ | |
| 2-291 | OCH$_2$CH$_2$OMe | n-Pr | 0 | CHF$_2$ | |
| 2-292 | OCH$_2$CH$_2$OMe | i-Pr | 0 | CHF$_2$ | |
| 2-293 | OCH$_2$CH$_2$OMe | Me | 1 | CHF$_2$ | |
| 2-294 | OCH$_2$CH$_2$OMe | Et | 1 | CHF$_2$ | |
| 2-295 | OCH$_2$CH$_2$OMe | n-Pr | 1 | CHF$_2$ | |
| 2-296 | OCH$_2$CH$_2$OMe | i-Pr | 1 | CHF$_2$ | |
| 2-297 | OCH$_2$CH$_2$OMe | Me | 2 | CHF$_2$ | |
| 2-298 | OCH$_2$CH$_2$OMe | Et | 2 | CHF$_2$ | |
| 2-299 | OCH$_2$CH$_2$OMe | n-Pr | 2 | CHF$_2$ | |
| 2-300 | OCH$_2$CH$_2$OMe | i-Pr | 2 | CHF$_2$ | |
| 2-301 | OCH$_2$CH$_2$SMe | Me | 0 | CHF$_2$ | |
| 2-302 | OCH$_2$CH$_2$SMe | Et | 0 | CHF$_2$ | |
| 2-303 | OCH$_2$CH$_2$SMe | n-Pr | 0 | CHF$_2$ | |
| 2-304 | OCH$_2$CH$_2$SMe | i-Pr | 0 | CHF$_2$ | |
| 2-305 | OCH$_2$CH$_2$SMe | Me | 1 | CHF$_2$ | |
| 2-306 | OCH$_2$CH$_2$SMe | Et | 1 | CHF$_2$ | |
| 2-307 | OCH$_2$CH$_2$SMe | n-Pr | 1 | CHF$_2$ | |
| 2-308 | OCH$_2$CH$_2$SMe | i-Pr | 1 | CHF$_2$ | |
| 2-309 | OCH$_2$CH$_2$SMe | Me | 2 | CHF$_2$ | |
| 2-310 | OCH$_2$CH$_2$SMe | Et | 2 | CHF$_2$ | |
| 2-311 | OCH$_2$CH$_2$SMe | n-Pr | 2 | CHF$_2$ | |
| 2-312 | OCH$_2$CH$_2$SMe | i-Pr | 2 | CHF$_2$ | |
| 2-313 | OCH$_2$CH$_2$SO$_2$Me | Me | 0 | CHF$_2$ | |
| 2-314 | OCH$_2$CH$_2$SO$_2$Me | Et | 0 | CHF$_2$ | |
| 2-315 | OCH$_2$CH$_2$SO$_2$Me | n-Pr | 0 | CHF$_2$ | |
| 2-316 | OCH$_2$CH$_2$SO$_2$Me | i-Pr | 0 | CHF$_2$ | |
| 2-317 | OCH$_2$CH$_2$SO$_2$Me | Me | 1 | CHF$_2$ | |
| 2-318 | OCH$_2$CH$_2$SO$_2$Me | Et | 1 | CHF$_2$ | |
| 2-319 | OCH$_2$CH$_2$SO$_2$Me | n-Pr | 1 | CHF$_2$ | |
| 2-320 | OCH$_2$CH$_2$SO$_2$Me | i-Pr | 1 | CHF$_2$ | |
| 2-321 | OCH$_2$CH$_2$SO$_2$Me | Me | 2 | CHF$_2$ | |
| 2-322 | OCH$_2$CH$_2$SO$_2$Me | Et | 2 | CHF$_2$ | |
| 2-323 | OCH$_2$CH$_2$SO$_2$Me | n-Pr | 2 | CHF$_2$ | |
| 2-324 | OCH$_2$CH$_2$SO$_2$Me | i-Pr | 2 | CHF$_2$ | |
| 2-325 | OMe | Me | 0 | CF(CF$_3$)$_2$ | |
| 2-326 | OMe | Et | 0 | CF(CF$_3$)$_2$ | |
| 2-327 | OMe | n-Pr | 0 | CF(CF$_3$)$_2$ | |
| 2-328 | OMe | i-Pr | 0 | CF(CF$_3$)$_2$ | |
| 2-329 | OMe | Me | 1 | CF(CF$_3$)$_2$ | |
| 2-330 | OMe | Et | 1 | CF(CF$_3$)$_2$ | |
| 2-331 | OMe | n-Pr | 1 | CF(CF$_3$)$_2$ | |
| 2-332 | OMe | i-Pr | 1 | CF(CF$_3$)$_2$ | |
| 2-333 | OMe | Me | 2 | CF(CF$_3$)$_2$ | |
| 2-334 | OMe | Et | 2 | CF(CF$_3$)$_2$ | |
| 2-335 | OMe | n-Pr | 2 | CF(CF$_3$)$_2$ | |
| 2-336 | OMe | i-Pr | 2 | CF(CF$_3$)$_2$ | |
| 2-337 | OEt | Me | 0 | CF(CF$_3$)$_2$ | |
| 2-338 | OEt | Et | 0 | CF(CF$_3$)$_2$ | |
| 2-339 | OEt | n-Pr | 0 | CF(CF$_3$)$_2$ | |
| 2-340 | OEt | i-Pr | 0 | CF(CF$_3$)$_2$ | |

TABLE 2-continued

Compounds of the formula (I) according to the invention in which $R^2$ is hydroxyl, $R^3$ to $R^6$ are each hydrogen and $R^7$ and $R^8$ are each methyl.

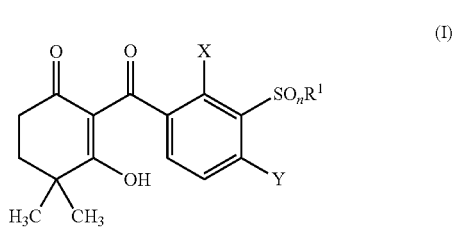

(I)

| No. | X | $R^1$ | n | Y | Physical data: $^1$H-NMR: δ [CDCl$_3$] |
|---|---|---|---|---|---|
| 2-341 | OEt | Me | 1 | CF(CF$_3$)$_2$ | |
| 2-342 | OEt | Et | 1 | CF(CF$_3$)$_2$ | |
| 2-343 | OEt | n-Pr | 1 | CF(CF$_3$)$_2$ | |
| 2-344 | OEt | i-Pr | 1 | CF(CF$_3$)$_2$ | |
| 2-345 | OEt | Me | 2 | CF(CF$_3$)$_2$ | |
| 2-346 | OEt | Et | 2 | CF(CF$_3$)$_2$ | |
| 2-347 | OEt | n-Pr | 2 | CF(CF$_3$)$_2$ | |
| 2-348 | OEt | i-Pr | 2 | CF(CF$_3$)$_2$ | |
| 2-349 | O—CH$_2$—c-Pr | Me | 0 | CF(CF$_3$)$_2$ | |
| 2-350 | O—CH$_2$—c-Pr | Et | 0 | CF(CF$_3$)$_2$ | |
| 2-351 | O—CH$_2$—c-Pr | n-Pr | 0 | CF(CF$_3$)$_2$ | |
| 2-352 | O—CH$_2$—c-Pr | i-Pr | 0 | CF(CF$_3$)$_2$ | |
| 2-353 | O—CH$_2$—c-Pr | Me | 1 | CF(CF$_3$)$_2$ | |
| 2-354 | O—CH$_2$—c-Pr | Et | 1 | CF(CF$_3$)$_2$ | |
| 2-355 | O—CH$_2$—c-Pr | n-Pr | 1 | CF(CF$_3$)$_2$ | |
| 2-356 | O—CH$_2$—c-Pr | i-Pr | 1 | CF(CF$_3$)$_2$ | |
| 2-357 | O—CH$_2$—c-Pr | Me | 2 | CF(CF$_3$)$_2$ | |
| 2-358 | O—CH$_2$—c-Pr | Et | 2 | CF(CF$_3$)$_2$ | |
| 2-359 | O—CH$_2$—c-Pr | n-Pr | 2 | CF(CF$_3$)$_2$ | |
| 2-360 | O—CH$_2$—c-Pr | i-Pr | 2 | CF(CF$_3$)$_2$ | |
| 2-361 | OCH$_2$CH$_2$OMe | Me | 0 | CF(CF$_3$)$_2$ | |
| 2-362 | OCH$_2$CH$_2$OMe | Et | 0 | CF(CF$_3$)$_2$ | |
| 2-363 | OCH$_2$CH$_2$OMe | n-Pr | 0 | CF(CF$_3$)$_2$ | |
| 2-364 | OCH$_2$CH$_2$OMe | i-Pr | 0 | CF(CF$_3$)$_2$ | |
| 2-365 | OCH$_2$CH$_2$OMe | Me | 1 | CF(CF$_3$)$_2$ | |
| 2-366 | OCH$_2$CH$_2$OMe | Et | 1 | CF(CF$_3$)$_2$ | |
| 2-367 | OCH$_2$CH$_2$OMe | n-Pr | 1 | CF(CF$_3$)$_2$ | |
| 2-368 | OCH$_2$CH$_2$OMe | i-Pr | 1 | CF(CF$_3$)$_2$ | |
| 2-369 | OCH$_2$CH$_2$OMe | Me | 2 | CF(CF$_3$)$_2$ | |
| 2-370 | OCH$_2$CH$_2$OMe | Et | 2 | CF(CF$_3$)$_2$ | |
| 2-371 | OCH$_2$CH$_2$OMe | n-Pr | 2 | CF(CF$_3$)$_2$ | |
| 2-372 | OCH$_2$CH$_2$OMe | i-Pr | 2 | CF(CF$_3$)$_2$ | |
| 2-373 | OCH$_2$CH$_2$SMe | Me | 0 | CF(CF$_3$)$_2$ | |
| 2-374 | OCH$_2$CH$_2$SMe | Et | 0 | CF(CF$_3$)$_2$ | |
| 2-375 | OCH$_2$CH$_2$SMe | n-Pr | 0 | CF(CF$_3$)$_2$ | |
| 2-376 | OCH$_2$CH$_2$SMe | i-Pr | 0 | CF(CF$_3$)$_2$ | |
| 2-377 | OCH$_2$CH$_2$SMe | Me | 1 | CF(CF$_3$)$_2$ | |
| 2-378 | OCH$_2$CH$_2$SMe | Et | 1 | CF(CF$_3$)$_2$ | |
| 2-379 | OCH$_2$CH$_2$SMe | n-Pr | 1 | CF(CF$_3$)$_2$ | |
| 2-380 | OCH$_2$CH$_2$SMe | i-Pr | 1 | CF(CF$_3$)$_2$ | |
| 2-381 | OCH$_2$CH$_2$SMe | Me | 2 | CF(CF$_3$)$_2$ | |
| 2-382 | OCH$_2$CH$_2$SMe | Et | 2 | CF(CF$_3$)$_2$ | |
| 2-383 | OCH$_2$CH$_2$SMe | n-Pr | 2 | CF(CF$_3$)$_2$ | |
| 2-384 | OCH$_2$CH$_2$SMe | i-Pr | 2 | CF(CF$_3$)$_2$ | |
| 2-385 | OCH$_2$CH$_2$SO$_2$Me | Me | 0 | CF(CF$_3$)$_2$ | |
| 2-386 | OCH$_2$CH$_2$SO$_2$Me | Et | 0 | CF(CF$_3$)$_2$ | |
| 2-387 | OCH$_2$CH$_2$SO$_2$Me | n-Pr | 0 | CF(CF$_3$)$_2$ | |
| 2-388 | OCH$_2$CH$_2$SO$_2$Me | i-Pr | 0 | CF(CF$_3$)$_2$ | |
| 2-389 | OCH$_2$CH$_2$SO$_2$Me | Me | 1 | CF(CF$_3$)$_2$ | |
| 2-390 | OCH$_2$CH$_2$SO$_2$Me | Et | 1 | CF(CF$_3$)$_2$ | |
| 2-391 | OCH$_2$CH$_2$SO$_2$Me | n-Pr | 1 | CF(CF$_3$)$_2$ | |
| 2-392 | OCH$_2$CH$_2$SO$_2$Me | i-Pr | 1 | CF(CF$_3$)$_2$ | |
| 2-393 | OCH$_2$CH$_2$SO$_2$Me | Me | 2 | CF(CF$_3$)$_2$ | |
| 2-394 | OCH$_2$CH$_2$SO$_2$Me | Et | 2 | CF(CF$_3$)$_2$ | |
| 2-395 | OCH$_2$CH$_2$SO$_2$Me | n-Pr | 2 | CF(CF$_3$)$_2$ | |
| 2-396 | OCH$_2$CH$_2$SO$_2$Me | i-Pr | 2 | CF(CF$_3$)$_2$ | |

TABLE 3

Compounds of the formula (I) according to the invention in which $R^2$ is hydroxyl, $R^3$, $R^4$, $R^7$ and $R^8$ are each hydrogen and $R^5$ and $R^6$ are each methyl.

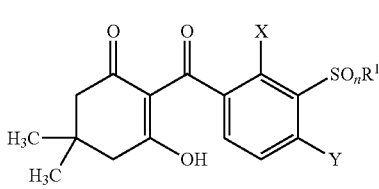

(I)

| No. | X | $R^1$ | n | Y | Physical data: $^1$H-NMR: δ [CDCl$_3$] |
|---|---|---|---|---|---|
| 3-1 | OH | Me | 0 | CF$_3$ | |
| 3-2 | OH | Et | 0 | CF$_3$ | |
| 3-3 | OH | n-Pr | 0 | CF$_3$ | |
| 3-4 | OH | i-Pr | 0 | CF$_3$ | |
| 3-5 | OH | Me | 1 | CF$_3$ | |
| 3-6 | OH | Et | 1 | CF$_3$ | |
| 3-7 | OH | n-Pr | 1 | CF$_3$ | |
| 3-8 | OH | i-Pr | 1 | CF$_3$ | |
| 3-9 | OH | Me | 2 | CF$_3$ | |
| 3-10 | OH | Et | 2 | CF$_3$ | |

TABLE 3-continued

Compounds of the formula (I) according to the invention in which $R^2$ is hydroxyl, $R^3$, $R^4$, $R^7$ and $R^8$ are each hydrogen and $R^5$ and $R^6$ are each methyl.

$$\text{(I)}$$

| No. | X | $R^1$ | n | Y | Physical data: $^1$H-NMR: δ [CDCl$_3$] |
|---|---|---|---|---|---|
| 3-11 | OH | n-Pr | 2 | CF$_3$ | |
| 3-12 | OH | i-Pr | 2 | CF$_3$ | |
| 3-13 | OMe | Me | 0 | CF$_3$ | |
| 3-14 | OMe | Et | 0 | CF$_3$ | |
| 3-15 | OMe | n-Pr | 0 | CF$_3$ | |
| 3-16 | OMe | i-Pr | 0 | CF$_3$ | |
| 3-17 | OMe | Me | 1 | CF$_3$ | 16.71 (s, 1H), 7.57 (d, 1H), 7.42 (d, 1H), 3.87 (s, 3H), 3.07 (s, 3H), 2.71 (d, 1H), 2.64 (d, 1H), 2.38 (d, 1H), 2.24 (d, 1H), 1.17 (s, 3H), 1.11 (s, 3H) |
| 3-18 | OMe | Et | 1 | CF$_3$ | |
| 3-19 | OMe | n-Pr | 1 | CF$_3$ | |
| 3-20 | OMe | i-Pr | 1 | CF$_3$ | |
| 3-21 | OMe | Me | 2 | CF$_3$ | |
| 3-22 | OMe | Et | 2 | CF$_3$ | |
| 3-23 | OMe | n-Pr | 2 | CF$_3$ | |
| 3-24 | OMe | i-Pr | 2 | CF$_3$ | |
| 3-25 | OEt | Me | 0 | CF$_3$ | |
| 3-26 | OEt | Et | 0 | CF$_3$ | |
| 3-27 | OEt | n-Pr | 0 | CF$_3$ | |
| 3-28 | OEt | i-Pr | 0 | CF$_3$ | |
| 3-29 | OEt | Me | 1 | CF$_3$ | |
| 3-30 | OEt | Et | 1 | CF$_3$ | |
| 3-31 | OEt | n-Pr | 1 | CF$_3$ | |
| 3-32 | OEt | i-Pr | 1 | CF$_3$ | |
| 3-33 | OEt | Me | 2 | CF$_3$ | |
| 3-34 | OEt | Et | 2 | CF$_3$ | |
| 3-35 | OEt | n-Pr | 2 | CF$_3$ | |
| 3-36 | OEt | i-Pr | 2 | CF$_3$ | |
| 3-37 | O—CH$_2$—c-Pr | Me | 0 | CF$_3$ | |
| 3-38 | O—CH$_2$—c-Pr | Et | 0 | CF$_3$ | |
| 3-39 | O—CH$_2$—c-Pr | n-Pr | 0 | CF$_3$ | |
| 3-40 | O—CH$_2$—c-Pr | i-Pr | 0 | CF$_3$ | |
| 3-41 | O—CH$_2$—c-Pr | Me | 1 | CF$_3$ | |
| 3-42 | O—CH$_2$—c-Pr | Et | 1 | CF$_3$ | |
| 3-43 | O—CH$_2$—c-Pr | n-Pr | 1 | CF$_3$ | |
| 3-44 | O—CH$_2$—c-Pr | i-Pr | 1 | CF$_3$ | |
| 3-45 | O—CH$_2$—c-Pr | Me | 2 | CF$_3$ | |
| 3-46 | O—CH$_2$—c-Pr | Et | 2 | CF$_3$ | |
| 3-47 | O—CH$_2$—c-Pr | n-Pr | 2 | CF$_3$ | |
| 3-48 | O—CH$_2$—c-Pr | i-Pr | 2 | CF$_3$ | |
| 3-49 | OCH$_2$CH$_2$OMe | Me | 0 | CF$_3$ | |
| 3-50 | OCH$_2$CH$_2$OMe | Et | 0 | CF$_3$ | |
| 3-51 | OCH$_2$CH$_2$OMe | n-Pr | 0 | CF$_3$ | |
| 3-52 | OCH$_2$CH$_2$OMe | i-Pr | 0 | CF$_3$ | |
| 3-53 | OCH$_2$CH$_2$OMe | Me | 1 | CF$_3$ | |
| 3-54 | OCH$_2$CH$_2$OMe | Et | 1 | CF$_3$ | |
| 3-55 | OCH$_2$CH$_2$OMe | n-Pr | 1 | CF$_3$ | |
| 3-56 | OCH$_2$CH$_2$OMe | i-Pr | 1 | CF$_3$ | |
| 3-57 | OCH$_2$CH$_2$OMe | Me | 2 | CF$_3$ | |
| 3-58 | OCH$_2$CH$_2$OMe | Et | 2 | CF$_3$ | |
| 3-59 | OCH$_2$CH$_2$OMe | n-Pr | 2 | CF$_3$ | |
| 3-60 | OCH$_2$CH$_2$OMe | i-Pr | 2 | CF$_3$ | |
| 3-61 | OCH$_2$CH$_2$SMe | Me | 0 | CF$_3$ | |
| 3-62 | OCH$_2$CH$_2$SMe | Et | 0 | CF$_3$ | |
| 3-63 | OCH$_2$CH$_2$SMe | n-Pr | 0 | CF$_3$ | |
| 3-64 | OCH$_2$CH$_2$SMe | i-Pr | 0 | CF$_3$ | |
| 3-65 | OCH$_2$CH$_2$SMe | Me | 1 | CF$_3$ | |
| 3-66 | OCH$_2$CH$_2$SMe | Et | 1 | CF$_3$ | |
| 3-67 | OCH$_2$CH$_2$SMe | n-Pr | 1 | CF$_3$ | |
| 3-68 | OCH$_2$CH$_2$SMe | i-Pr | 1 | CF$_3$ | |
| 3-69 | OCH$_2$CH$_2$SMe | Me | 2 | CF$_3$ | |
| 3-70 | OCH$_2$CH$_2$SMe | Et | 2 | CF$_3$ | |

TABLE 3-continued

Compounds of the formula (I) according to the invention in which $R^2$ is hydroxyl, $R^3$, $R^4$, $R^7$ and $R^8$ are each hydrogen and $R^5$ and $R^6$ are each methyl.

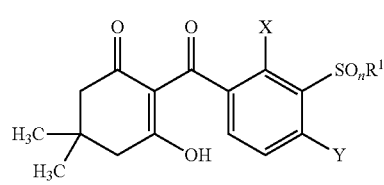
(I)

| No. | X | $R^1$ | n | Y | Physical data: $^1$H-NMR: δ [CDCl$_3$] |
|---|---|---|---|---|---|
| 3-71 | OCH$_2$CH$_2$SMe | n-Pr | 2 | CF$_3$ | |
| 3-72 | OCH$_2$CH$_2$SMe | i-Pr | 2 | CF$_3$ | |
| 3-73 | OCH$_2$CH$_2$SO$_2$Me | Me | 0 | CF$_3$ | |
| 3-74 | OCH$_2$CH$_2$SO$_2$Me | Et | 0 | CF$_3$ | |
| 3-75 | OCH$_2$CH$_2$SO$_2$Me | n-Pr | 0 | CF$_3$ | |
| 3-76 | OCH$_2$CH$_2$SO$_2$Me | i-Pr | 0 | CF$_3$ | |
| 3-77 | OCH$_2$CH$_2$SO$_2$Me | Me | 1 | CF$_3$ | |
| 3-78 | OCH$_2$CH$_2$SO$_2$Me | Et | 1 | CF$_3$ | |
| 3-79 | OCH$_2$CH$_2$SO$_2$Me | n-Pr | 1 | CF$_3$ | |
| 3-80 | OCH$_2$CH$_2$SO$_2$Me | i-Pr | 1 | CF$_3$ | |
| 3-81 | OCH$_2$CH$_2$SO$_2$Me | Me | 2 | CF$_3$ | |
| 3-82 | OCH$_2$CH$_2$SO$_2$Me | Et | 2 | CF$_3$ | |
| 3-83 | OCH$_2$CH$_2$SO$_2$Me | n-Pr | 2 | CF$_3$ | |
| 3-84 | OCH$_2$CH$_2$SO$_2$Me | i-Pr | 2 | CF$_3$ | |
| 3-85 | OCOMe | Me | 0 | CF$_3$ | |
| 3-86 | OCOMe | Et | 0 | CF$_3$ | |
| 3-87 | OCOMe | n-Pr | 0 | CF$_3$ | |
| 3-88 | OCOMe | i-Pr | 0 | CF$_3$ | |
| 3-89 | OCOMe | Me | 1 | CF$_3$ | |
| 3-90 | OCOMe | Et | 1 | CF$_3$ | |
| 3-91 | OCOMe | n-Pr | 1 | CF$_3$ | |
| 3-92 | OCOMe | i-Pr | 1 | CF$_3$ | |
| 3-93 | OCOMe | Me | 2 | CF$_3$ | |
| 3-94 | OCOMe | Et | 2 | CF$_3$ | |
| 3-95 | OCOMe | n-Pr | 2 | CF$_3$ | |
| 3-96 | OCOMe | i-Pr | 2 | CF$_3$ | |
| 3-97 | OSO$_2$Me | Me | 0 | CF$_3$ | |
| 3-98 | OSO$_2$Me | Et | 0 | CF$_3$ | |
| 3-99 | OSO$_2$Me | n-Pr | 0 | CF$_3$ | |
| 3-100 | OSO$_2$Me | i-Pr | 0 | CF$_3$ | |
| 3-101 | OSO$_2$Me | Me | 1 | CF$_3$ | |
| 3-102 | OSO$_2$Me | Et | 1 | CF$_3$ | |
| 3-103 | OSO$_2$Me | n-Pr | 1 | CF$_3$ | |
| 3-104 | OSO$_2$Me | i-Pr | 1 | CF$_3$ | |
| 3-105 | OSO$_2$Me | Me | 2 | CF$_3$ | |
| 3-106 | OSO$_2$Me | Et | 2 | CF$_3$ | |
| 3-107 | OSO$_2$Me | n-Pr | 2 | CF$_3$ | |
| 3-108 | OSO$_2$Me | i-Pr | 2 | CF$_3$ | |
| 3-109 | OMe | Me | 0 | C$_2$F$_5$ | |
| 3-110 | OMe | Et | 0 | C$_2$F$_5$ | |
| 3-111 | OMe | n-Pr | 0 | C$_2$F$_5$ | |
| 3-112 | OMe | i-Pr | 0 | C$_2$F$_5$ | |
| 3-113 | OMe | Me | 1 | C$_2$F$_5$ | |
| 3-114 | OMe | Et | 1 | C$_2$F$_5$ | |
| 3-115 | OMe | n-Pr | 1 | C$_2$F$_5$ | |
| 3-116 | OMe | i-Pr | 1 | C$_2$F$_5$ | |
| 3-117 | OMe | Me | 2 | C$_2$F$_5$ | |
| 3-118 | OMe | Et | 2 | C$_2$F$_5$ | |
| 3-119 | OMe | n-Pr | 2 | C$_2$F$_5$ | |
| 3-120 | OMe | i-Pr | 2 | C$_2$F$_5$ | |
| 3-121 | OEt | Me | 0 | C$_2$F$_5$ | |
| 3-122 | OEt | Et | 0 | C$_2$F$_5$ | |
| 3-123 | OEt | n-Pr | 0 | C$_2$F$_5$ | |
| 3-124 | OEt | i-Pr | 0 | C$_2$F$_5$ | |
| 3-125 | OEt | Me | 1 | C$_2$F$_5$ | |
| 3-126 | OEt | Et | 1 | C$_2$F$_5$ | |
| 3-127 | OEt | n-Pr | 1 | C$_2$F$_5$ | |
| 3-128 | OEt | i-Pr | 1 | C$_2$F$_5$ | |
| 3-129 | OEt | Me | 2 | C$_2$F$_5$ | |
| 3-130 | OEt | Et | 2 | C$_2$F$_5$ | |
| 3-131 | OEt | n-Pr | 2 | C$_2$F$_5$ | |
| 3-132 | OEt | i-Pr | 2 | C$_2$F$_5$ | |
| 3-133 | O—CH$_2$—c-Pr | Me | 0 | C$_2$F$_5$ | |

TABLE 3-continued

Compounds of the formula (I) according to the invention in which $R^2$ is hydroxyl, $R^3$, $R^4$, $R^7$ and $R^8$ are each hydrogen and $R^5$ and $R^6$ are each methyl.

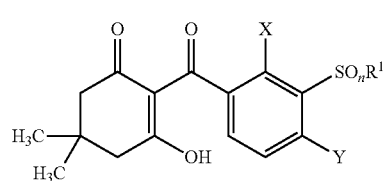

(I)

| No. | X | $R^1$ | n | Y | Physical data: $^1$H-NMR: δ [CDCl$_3$] |
|---|---|---|---|---|---|
| 3-134 | O—CH$_2$—c-Pr | Et | 0 | C$_2$F$_5$ | |
| 3-135 | O—CH$_2$—c-Pr | n-Pr | 0 | C$_2$F$_5$ | |
| 3-136 | O—CH$_2$—c-Pr | i-Pr | 0 | C$_2$F$_5$ | |
| 3-137 | O—CH$_2$—c-Pr | Me | 1 | C$_2$F$_5$ | |
| 3-138 | O—CH$_2$—c-Pr | Et | 1 | C$_2$F$_5$ | |
| 3-139 | O—CH$_2$—c-Pr | n-Pr | 1 | C$_2$F$_5$ | |
| 3-140 | O—CH$_2$—c-Pr | i-Pr | 1 | C$_2$F$_5$ | |
| 3-141 | O—CH$_2$—c-Pr | Me | 2 | C$_2$F$_5$ | |
| 3-142 | O—CH$_2$—c-Pr | Et | 2 | C$_2$F$_5$ | |
| 3-143 | O—CH$_2$—c-Pr | n-Pr | 2 | C$_2$F$_5$ | |
| 3-144 | O—CH$_2$—c-Pr | i-Pr | 2 | C$_2$F$_5$ | |
| 3-145 | OCH$_2$CH$_2$OMe | Me | 0 | C$_2$F$_5$ | |
| 3-146 | OCH$_2$CH$_2$OMe | Et | 0 | C$_2$F$_5$ | |
| 3-147 | OCH$_2$CH$_2$OMe | n-Pr | 0 | C$_2$F$_5$ | |
| 3-148 | OCH$_2$CH$_2$OMe | i-Pr | 0 | C$_2$F$_5$ | |
| 3-149 | OCH$_2$CH$_2$OMe | Me | 1 | C$_2$F$_5$ | |
| 3-150 | OCH$_2$CH$_2$OMe | Et | 1 | C$_2$F$_5$ | |
| 3-151 | OCH$_2$CH$_2$OMe | n-Pr | 1 | C$_2$F$_5$ | |
| 3-152 | OCH$_2$CH$_2$OMe | i-Pr | 1 | C$_2$F$_5$ | |
| 3-153 | OCH$_2$CH$_2$OMe | Me | 2 | C$_2$F$_5$ | |
| 3-154 | OCH$_2$CH$_2$OMe | Et | 2 | C$_2$F$_5$ | |
| 3-155 | OCH$_2$CH$_2$OMe | n-Pr | 2 | C$_2$F$_5$ | |
| 3-156 | OCH$_2$CH$_2$OMe | i-Pr | 2 | C$_2$F$_5$ | |
| 3-157 | OCH$_2$CH$_2$SMe | Me | 0 | C$_2$F$_5$ | |
| 3-158 | OCH$_2$CH$_2$SMe | Et | 0 | C$_2$F$_5$ | |
| 3-159 | OCH$_2$CH$_2$SMe | n-Pr | 0 | C$_2$F$_5$ | |
| 3-160 | OCH$_2$CH$_2$SMe | i-Pr | 0 | C$_2$F$_5$ | |
| 3-161 | OCH$_2$CH$_2$SMe | Me | 1 | C$_2$F$_5$ | |
| 3-162 | OCH$_2$CH$_2$SMe | Et | 1 | C$_2$F$_5$ | |
| 3-163 | OCH$_2$CH$_2$SMe | n-Pr | 1 | C$_2$F$_5$ | |
| 3-164 | OCH$_2$CH$_2$SMe | i-Pr | 1 | C$_2$F$_5$ | |
| 3-165 | OCH$_2$CH$_2$SMe | Me | 2 | C$_2$F$_5$ | |
| 3-166 | OCH$_2$CH$_2$SMe | Et | 2 | C$_2$F$_5$ | |
| 3-167 | OCH$_2$CH$_2$SMe | n-Pr | 2 | C$_2$F$_5$ | |
| 3-168 | OCH$_2$CH$_2$SMe | i-Pr | 2 | C$_2$F$_5$ | |
| 3-169 | OCH$_2$CH$_2$SO$_2$Me | Me | 0 | C$_2$F$_5$ | |
| 3-170 | OCH$_2$CH$_2$SO$_2$Me | Et | 0 | C$_2$F$_5$ | |
| 3-171 | OCH$_2$CH$_2$SO$_2$Me | n-Pr | 0 | C$_2$F$_5$ | |
| 3-172 | OCH$_2$CH$_2$SO$_2$Me | i-Pr | 0 | C$_2$F$_5$ | |
| 3-173 | OCH$_2$CH$_2$SO$_2$Me | Me | 1 | C$_2$F$_5$ | |
| 3-174 | OCH$_2$CH$_2$SO$_2$Me | Et | 1 | C$_2$F$_5$ | |
| 3-175 | OCH$_2$CH$_2$SO$_2$Me | n-Pr | 1 | C$_2$F$_5$ | |
| 3-176 | OCH$_2$CH$_2$SO$_2$Me | i-Pr | 1 | C$_2$F$_5$ | |
| 3-177 | OCH$_2$CH$_2$SO$_2$Me | Me | 2 | C$_2$F$_5$ | |
| 3-178 | OCH$_2$CH$_2$SO$_2$Me | Et | 2 | C$_2$F$_5$ | |
| 3-179 | OCH$_2$CH$_2$SO$_2$Me | n-Pr | 2 | C$_2$F$_5$ | |
| 3-180 | OCH$_2$CH$_2$SO$_2$Me | i-Pr | 2 | C$_2$F$_5$ | |
| 3-181 | OMe | Me | 0 | CCl$_3$ | |
| 3-182 | OMe | Et | 0 | CCl$_3$ | |
| 3-183 | OMe | n-Pr | 0 | CCl$_3$ | |
| 3-184 | OMe | i-Pr | 0 | CCl$_3$ | |
| 3-185 | OMe | Me | 1 | CCl$_3$ | |
| 3-186 | OMe | Et | 1 | CCl$_3$ | |
| 3-187 | OMe | n-Pr | 1 | CCl$_3$ | |
| 3-188 | OMe | i-Pr | 1 | CCl$_3$ | |
| 3-189 | OMe | Me | 2 | CCl$_3$ | |
| 3-190 | OMe | Et | 2 | CCl$_3$ | |
| 3-191 | OMe | n-Pr | 2 | CCl$_3$ | |
| 3-192 | OMe | i-Pr | 2 | CCl$_3$ | |
| 3-193 | OEt | Me | 0 | CCl$_3$ | |
| 3-194 | OEt | Et | 0 | CCl$_3$ | |
| 3-195 | OEt | n-Pr | 0 | CCl$_3$ | |
| 3-196 | OEt | i-Pr | 0 | CCl$_3$ | |

TABLE 3-continued

Compounds of the formula (I) according to the invention in which $R^2$ is hydroxyl, $R^3$, $R^4$, $R^7$ and $R^8$ are each hydrogen and $R^5$ and $R^6$ are each methyl.

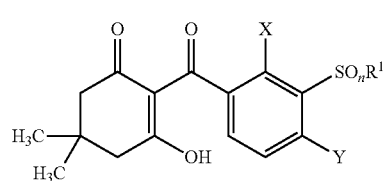
(I)

| No. | X | $R^1$ | n | Y | Physical data: $^1$H-NMR: δ [CDCl$_3$] |
|---|---|---|---|---|---|
| 3-197 | OEt | Me | 1 | CCl$_3$ | |
| 3-198 | OEt | Et | 1 | CCl$_3$ | |
| 3-199 | OEt | n-Pr | 1 | CCl$_3$ | |
| 3-200 | OEt | i-Pr | 1 | CCl$_3$ | |
| 3-201 | OEt | Me | 2 | CCl$_3$ | |
| 3-202 | OEt | Et | 2 | CCl$_3$ | |
| 3-203 | OEt | n-Pr | 2 | CCl$_3$ | |
| 3-204 | OEt | i-Pr | 2 | CCl$_3$ | |
| 3-205 | O—CH$_2$—c-Pr | Me | 0 | CCl$_3$ | |
| 3-206 | O—CH$_2$—c-Pr | Et | 0 | CCl$_3$ | |
| 3-207 | O—CH$_2$—c-Pr | n-Pr | 0 | CCl$_3$ | |
| 3-208 | O—CH$_2$—c-Pr | i-Pr | 0 | CCl$_3$ | |
| 3-209 | O—CH$_2$—c-Pr | Me | 1 | CCl$_3$ | |
| 3-210 | O—CH$_2$—c-Pr | Et | 1 | CCl$_3$ | |
| 3-211 | O—CH$_2$—c-Pr | n-Pr | 1 | CCl$_3$ | |
| 3-212 | O—CH$_2$—c-Pr | i-Pr | 1 | CCl$_3$ | |
| 3-213 | O—CH$_2$—c-Pr | Me | 2 | CCl$_3$ | |
| 3-214 | O—CH$_2$—c-Pr | Et | 2 | CCl$_3$ | |
| 3-215 | O—CH$_2$—c-Pr | n-Pr | 2 | CCl$_3$ | |
| 3-216 | O—CH$_2$—c-Pr | i-Pr | 2 | CCl$_3$ | |
| 3-217 | OCH$_2$CH$_2$OMe | Me | 0 | CCl$_3$ | |
| 3-218 | OCH$_2$CH$_2$OMe | Et | 0 | CCl$_3$ | |
| 3-219 | OCH$_2$CH$_2$OMe | n-Pr | 0 | CCl$_3$ | |
| 3-220 | OCH$_2$CH$_2$OMe | i-Pr | 0 | CCl$_3$ | |
| 3-221 | OCH$_2$CH$_2$OMe | Me | 1 | CCl$_3$ | |
| 3-222 | OCH$_2$CH$_2$OMe | Et | 1 | CCl$_3$ | |
| 3-223 | OCH$_2$CH$_2$OMe | n-Pr | 1 | CCl$_3$ | |
| 3-224 | OCH$_2$CH$_2$OMe | i-Pr | 1 | CCl$_3$ | |
| 3-225 | OCH$_2$CH$_2$OMe | Me | 2 | CCl$_3$ | |
| 3-226 | OCH$_2$CH$_2$OMe | Et | 2 | CCl$_3$ | |
| 3-227 | OCH$_2$CH$_2$OMe | n-Pr | 2 | CCl$_3$ | |
| 3-228 | OCH$_2$CH$_2$OMe | i-Pr | 2 | CCl$_3$ | |
| 3-229 | OCH$_2$CH$_2$SMe | Me | 0 | CCl$_3$ | |
| 3-230 | OCH$_2$CH$_2$SMe | Et | 0 | CCl$_3$ | |
| 3-231 | OCH$_2$CH$_2$SMe | n-Pr | 0 | CCl$_3$ | |
| 3-232 | OCH$_2$CH$_2$SMe | i-Pr | 0 | CCl$_3$ | |
| 3-233 | OCH$_2$CH$_2$SMe | Me | 1 | CCl$_3$ | |
| 3-234 | OCH$_2$CH$_2$SMe | Et | 1 | CCl$_3$ | |
| 3-235 | OCH$_2$CH$_2$SMe | n-Pr | 1 | CCl$_3$ | |
| 3-236 | OCH$_2$CH$_2$SMe | i-Pr | 1 | CCl$_3$ | |
| 3-237 | OCH$_2$CH$_2$SMe | Me | 2 | CCl$_3$ | |
| 3-238 | OCH$_2$CH$_2$SMe | Et | 2 | CCl$_3$ | |
| 3-239 | OCH$_2$CH$_2$SMe | n-Pr | 2 | CCl$_3$ | |
| 3-240 | OCH$_2$CH$_2$SMe | i-Pr | 2 | CCl$_3$ | |
| 3-241 | OCH$_2$CH$_2$SO$_2$Me | Me | 0 | CCl$_3$ | |
| 3-242 | OCH$_2$CH$_2$SO$_2$Me | Et | 0 | CCl$_3$ | |
| 3-243 | OCH$_2$CH$_2$SO$_2$Me | n-Pr | 0 | CCl$_3$ | |
| 3-244 | OCH$_2$CH$_2$SO$_2$Me | i-Pr | 0 | CCl$_3$ | |
| 3-245 | OCH$_2$CH$_2$SO$_2$Me | Me | 1 | CCl$_3$ | |
| 3-246 | OCH$_2$CH$_2$SO$_2$Me | Et | 1 | CCl$_3$ | |
| 3-247 | OCH$_2$CH$_2$SO$_2$Me | n-Pr | 1 | CCl$_3$ | |
| 3-248 | OCH$_2$CH$_2$SO$_2$Me | i-Pr | 1 | CCl$_3$ | |
| 3-249 | OCH$_2$CH$_2$SO$_2$Me | Me | 2 | CCl$_3$ | |
| 3-250 | OCH$_2$CH$_2$SO$_2$Me | Et | 2 | CCl$_3$ | |
| 3-251 | OCH$_2$CH$_2$SO$_2$Me | n-Pr | 2 | CCl$_3$ | |
| 3-252 | OCH$_2$CH$_2$SO$_2$Me | i-Pr | 2 | CCl$_3$ | |
| 3-253 | OMe | Me | 0 | CHF$_2$ | |
| 3-254 | OMe | Et | 0 | CHF$_2$ | |
| 3-255 | OMe | n-Pr | 0 | CHF$_2$ | |
| 3-256 | OMe | i-Pr | 0 | CHF$_2$ | |
| 3-257 | OMe | Me | 1 | CHF$_2$ | |
| 3-258 | OMe | Et | 1 | CHF$_2$ | |
| 3-259 | OMe | n-Pr | 1 | CHF$_2$ | |

TABLE 3-continued

Compounds of the formula (I) according to the invention in which $R^2$ is hydroxyl, $R^3$, $R^4$, $R^7$ and $R^8$ are each hydrogen and $R^5$ and $R^6$ are each methyl.

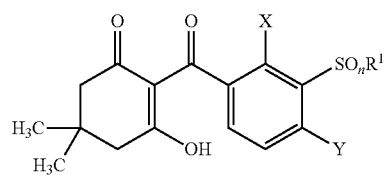

(I)

| No. | X | $R^1$ | n | Y | Physical data: $^1$H-NMR: δ [CDCl$_3$] |
|---|---|---|---|---|---|
| 3-260 | OMe | i-Pr | 1 | CHF$_2$ | |
| 3-261 | OMe | Me | 2 | CHF$_2$ | |
| 3-262 | OMe | Et | 2 | CHF$_2$ | |
| 3-263 | OMe | n-Pr | 2 | CHF$_2$ | |
| 3-264 | OMe | i-Pr | 2 | CHF$_2$ | |
| 3-265 | OEt | Me | 0 | CHF$_2$ | |
| 3-266 | OEt | Et | 0 | CHF$_2$ | |
| 3-267 | OEt | n-Pr | 0 | CHF$_2$ | |
| 3-268 | OEt | i-Pr | 0 | CHF$_2$ | |
| 3-269 | OEt | Me | 1 | CHF$_2$ | |
| 3-270 | OEt | Et | 1 | CHF$_2$ | |
| 3-271 | OEt | n-Pr | 1 | CHF$_2$ | |
| 3-272 | OEt | i-Pr | 1 | CHF$_2$ | |
| 3-273 | OEt | Me | 2 | CHF$_2$ | |
| 3-274 | OEt | Et | 2 | CHF$_2$ | |
| 3-275 | OEt | n-Pr | 2 | CHF$_2$ | |
| 3-276 | OEt | i-Pr | 2 | CHF$_2$ | |
| 3-277 | O—CH$_2$—c-Pr | Me | 0 | CHF$_2$ | |
| 3-278 | O—CH$_2$—c-Pr | Et | 0 | CHF$_2$ | |
| 3-279 | O—CH$_2$—c-Pr | n-Pr | 0 | CHF$_2$ | |
| 3-280 | O—CH$_2$—c-Pr | i-Pr | 0 | CHF$_2$ | |
| 3-281 | O—CH$_2$—c-Pr | Me | 1 | CHF$_2$ | |
| 3-282 | O—CH$_2$—c-Pr | Et | 1 | CHF$_2$ | |
| 3-283 | O—CH$_2$—c-Pr | n-Pr | 1 | CHF$_2$ | |
| 3-284 | O—CH$_2$—c-Pr | i-Pr | 1 | CHF$_2$ | |
| 3-285 | O—CH$_2$—c-Pr | Me | 2 | CHF$_2$ | |
| 3-286 | O—CH$_2$—c-Pr | Et | 2 | CHF$_2$ | |
| 3-287 | O—CH$_2$—c-Pr | n-Pr | 2 | CHF$_2$ | |
| 3-288 | O—CH$_2$—c-Pr | i-Pr | 2 | CHF$_2$ | |
| 3-289 | OCH$_2$CH$_2$OMe | Me | 0 | CHF$_2$ | |
| 3-290 | OCH$_2$CH$_2$OMe | Et | 0 | CHF$_2$ | |
| 3-291 | OCH$_2$CH$_2$OMe | n-Pr | 0 | CHF$_2$ | |
| 3-292 | OCH$_2$CH$_2$OMe | i-Pr | 0 | CHF$_2$ | |
| 3-293 | OCH$_2$CH$_2$OMe | Me | 1 | CHF$_2$ | |
| 3-294 | OCH$_2$CH$_2$OMe | Et | 1 | CHF$_2$ | |
| 3-295 | OCH$_2$CH$_2$OMe | n-Pr | 1 | CHF$_2$ | |
| 3-296 | OCH$_2$CH$_2$OMe | i-Pr | 1 | CHF$_2$ | |
| 3-297 | OCH$_2$CH$_2$OMe | Me | 2 | CHF$_2$ | |
| 3-298 | OCH$_2$CH$_2$OMe | Et | 2 | CHF$_2$ | |
| 3-299 | OCH$_2$CH$_2$OMe | n-Pr | 2 | CHF$_2$ | |
| 3-300 | OCH$_2$CH$_2$OMe | i-Pr | 2 | CHF$_2$ | |
| 3-301 | OCH$_2$CH$_2$SMe | Me | 0 | CHF$_2$ | |
| 3-302 | OCH$_2$CH$_2$SMe | Et | 0 | CHF$_2$ | |
| 3-303 | OCH$_2$CH$_2$SMe | n-Pr | 0 | CHF$_2$ | |
| 3-304 | OCH$_2$CH$_2$SMe | i-Pr | 0 | CHF$_2$ | |
| 3-305 | OCH$_2$CH$_2$SMe | Me | 1 | CHF$_2$ | |
| 3-306 | OCH$_2$CH$_2$SMe | Et | 1 | CHF$_2$ | |
| 3-307 | OCH$_2$CH$_2$SMe | n-Pr | 1 | CHF$_2$ | |
| 3-308 | OCH$_2$CH$_2$SMe | i-Pr | 1 | CHF$_2$ | |
| 3-309 | OCH$_2$CH$_2$SMe | Me | 2 | CHF$_2$ | |
| 3-310 | OCH$_2$CH$_2$SMe | Et | 2 | CHF$_2$ | |
| 3-311 | OCH$_2$CH$_2$SMe | n-Pr | 2 | CHF$_2$ | |
| 3-312 | OCH$_2$CH$_2$SMe | i-Pr | 2 | CHF$_2$ | |
| 3-313 | OCH$_2$CH$_2$SO$_2$Me | Me | 0 | CHF$_2$ | |
| 3-314 | OCH$_2$CH$_2$SO$_2$Me | Et | 0 | CHF$_2$ | |
| 3-315 | OCH$_2$CH$_2$SO$_2$Me | n-Pr | 0 | CHF$_2$ | |
| 3-316 | OCH$_2$CH$_2$SO$_2$Me | i-Pr | 0 | CHF$_2$ | |
| 3-317 | OCH$_2$CH$_2$SO$_2$Me | Me | 1 | CHF$_2$ | |
| 3-318 | OCH$_2$CH$_2$SO$_2$Me | Et | 1 | CHF$_2$ | |
| 3-319 | OCH$_2$CH$_2$SO$_2$Me | n-Pr | 1 | CHF$_2$ | |
| 3-320 | OCH$_2$CH$_2$SO$_2$Me | i-Pr | 1 | CHF$_2$ | |
| 3-321 | OCH$_2$CH$_2$SO$_2$Me | Me | 2 | CHF$_2$ | |
| 3-322 | OCH$_2$CH$_2$SO$_2$Me | Et | 2 | CHF$_2$ | |

TABLE 3-continued

Compounds of the formula (I) according to the invention in which $R^2$ is hydroxyl, $R^3$, $R^4$, $R^7$ and $R^8$ are each hydrogen and $R^5$ and $R^6$ are each methyl.

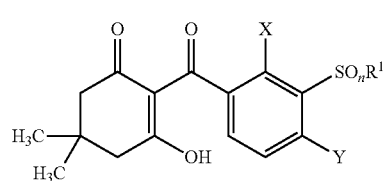

(I)

| No. | X | $R^1$ | n | Y | Physical data: $^1$H-NMR: δ [CDCl$_3$] |
|---|---|---|---|---|---|
| 3-323 | OCH$_2$CH$_2$SO$_2$Me | n-Pr | 2 | CHF$_2$ | |
| 3-324 | OCH$_2$CH$_2$SO$_2$Me | i-Pr | 2 | CHF$_2$ | |
| 3-325 | OMe | Me | 0 | CF(CF$_3$)$_2$ | |
| 3-326 | OMe | Et | 0 | CF(CF$_3$)$_2$ | |
| 3-327 | OMe | n-Pr | 0 | CF(CF$_3$)$_2$ | |
| 3-328 | OMe | i-Pr | 0 | CF(CF$_3$)$_2$ | |
| 3-329 | OMe | Me | 1 | CF(CF$_3$)$_2$ | |
| 3-330 | OMe | Et | 1 | CF(CF$_3$)$_2$ | |
| 3-331 | OMe | n-Pr | 1 | CF(CF$_3$)$_2$ | |
| 3-332 | OMe | i-Pr | 1 | CF(CF$_3$)$_2$ | |
| 3-333 | OMe | Me | 2 | CF(CF$_3$)$_2$ | |
| 3-334 | OMe | Et | 2 | CF(CF$_3$)$_2$ | |
| 3-335 | OMe | n-Pr | 2 | CF(CF$_3$)$_2$ | |
| 3-336 | OMe | i-Pr | 2 | CF(CF$_3$)$_2$ | |
| 3-337 | OEt | Me | 0 | CF(CF$_3$)$_2$ | |
| 3-338 | OEt | Et | 0 | CF(CF$_3$)$_2$ | |
| 3-339 | OEt | n-Pr | 0 | CF(CF$_3$)$_2$ | |
| 3-340 | OEt | i-Pr | 0 | CF(CF$_3$)$_2$ | |
| 3-341 | OEt | Me | 1 | CF(CF$_3$)$_2$ | |
| 3-342 | OEt | Et | 1 | CF(CF$_3$)$_2$ | |
| 3-343 | OEt | n-Pr | 1 | CF(CF$_3$)$_2$ | |
| 3-344 | OEt | i-Pr | 1 | CF(CF$_3$)$_2$ | |
| 3-345 | OEt | Me | 2 | CF(CF$_3$)$_2$ | |
| 3-346 | OEt | Et | 2 | CF(CF$_3$)$_2$ | |
| 3-347 | OEt | n-Pr | 2 | CF(CF$_3$)$_2$ | |
| 3-348 | OEt | i-Pr | 2 | CF(CF$_3$)$_2$ | |
| 3-349 | O—CH$_2$—c-Pr | Me | 0 | CF(CF$_3$)$_2$ | |
| 3-350 | O—CH$_2$—c-Pr | Et | 0 | CF(CF$_3$)$_2$ | |
| 3-351 | O—CH$_2$—c-Pr | n-Pr | 0 | CF(CF$_3$)$_2$ | |
| 3-352 | O—CH$_2$—c-Pr | i-Pr | 0 | CF(CF$_3$)$_2$ | |
| 3-353 | O—CH$_2$—c-Pr | Me | 1 | CF(CF$_3$)$_2$ | |
| 3-354 | O—CH$_2$—c-Pr | Et | 1 | CF(CF$_3$)$_2$ | |
| 3-355 | O—CH$_2$—c-Pr | n-Pr | 1 | CF(CF$_3$)$_2$ | |
| 3-356 | O—CH$_2$—c-Pr | i-Pr | 1 | CF(CF$_3$)$_2$ | |
| 3-357 | O—CH$_2$—c-Pr | Me | 2 | CF(CF$_3$)$_2$ | |
| 3-358 | O—CH$_2$—c-Pr | Et | 2 | CF(CF$_3$)$_2$ | |
| 3-359 | O—CH$_2$—c-Pr | n-Pr | 2 | CF(CF$_3$)$_2$ | |
| 3-360 | O—CH$_2$—c-Pr | i-Pr | 2 | CF(CF$_3$)$_2$ | |
| 3-361 | OCH$_2$CH$_2$OMe | Me | 0 | CF(CF$_3$)$_2$ | |
| 3-362 | OCH$_2$CH$_2$OMe | Et | 0 | CF(CF$_3$)$_2$ | |
| 3-363 | OCH$_2$CH$_2$OMe | n-Pr | 0 | CF(CF$_3$)$_2$ | |
| 3-364 | OCH$_2$CH$_2$OMe | i-Pr | 0 | CF(CF$_3$)$_2$ | |
| 3-365 | OCH$_2$CH$_2$OMe | Me | 1 | CF(CF$_3$)$_2$ | |
| 3-366 | OCH$_2$CH$_2$OMe | Et | 1 | CF(CF$_3$)$_2$ | |
| 3-367 | OCH$_2$CH$_2$OMe | n-Pr | 1 | CF(CF$_3$)$_2$ | |
| 3-368 | OCH$_2$CH$_2$OMe | i-Pr | 1 | CF(CF$_3$)$_2$ | |
| 3-369 | OCH$_2$CH$_2$OMe | Me | 2 | CF(CF$_3$)$_2$ | |
| 3-370 | OCH$_2$CH$_2$OMe | Et | 2 | CF(CF$_3$)$_2$ | |
| 3-371 | OCH$_2$CH$_2$OMe | n-Pr | 2 | CF(CF$_3$)$_2$ | |
| 3-372 | OCH$_2$CH$_2$OMe | i-Pr | 2 | CF(CF$_3$)$_2$ | |
| 3-373 | OCH$_2$CH$_2$SMe | Me | 0 | CF(CF$_3$)$_2$ | |
| 3-374 | OCH$_2$CH$_2$SMe | Et | 0 | CF(CF$_3$)$_2$ | |
| 3-375 | OCH$_2$CH$_2$SMe | n-Pr | 0 | CF(CF$_3$)$_2$ | |
| 3-376 | OCH$_2$CH$_2$SMe | i-Pr | 0 | CF(CF$_3$)$_2$ | |
| 3-377 | OCH$_2$CH$_2$SMe | Me | 1 | CF(CF$_3$)$_2$ | |
| 3-378 | OCH$_2$CH$_2$SMe | Et | 1 | CF(CF$_3$)$_2$ | |
| 3-379 | OCH$_2$CH$_2$SMe | n-Pr | 1 | CF(CF$_3$)$_2$ | |
| 3-380 | OCH$_2$CH$_2$SMe | i-Pr | 1 | CF(CF$_3$)$_2$ | |
| 3-381 | OCH$_2$CH$_2$SMe | Me | 2 | CF(CF$_3$)$_2$ | |
| 3-382 | OCH$_2$CH$_2$SMe | Et | 2 | CF(CF$_3$)$_2$ | |
| 3-383 | OCH$_2$CH$_2$SMe | n-Pr | 2 | CF(CF$_3$)$_2$ | |
| 3-384 | OCH$_2$CH$_2$SMe | i-Pr | 2 | CF(CF$_3$)$_2$ | |
| 3-385 | OCH$_2$CH$_2$SO$_2$Me | Me | 0 | CF(CF$_3$)$_2$ | |

TABLE 3-continued

Compounds of the formula (I) according to the invention in which $R^2$ is hydroxyl, $R^3$, $R^4$, $R^7$ and $R^8$ are each hydrogen and $R^5$ and $R^6$ are each methyl.

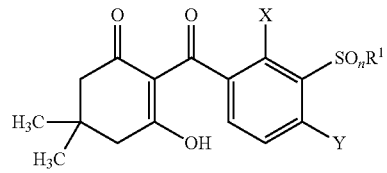

(I)

| No. | X | $R^1$ | n | Y | Physical data: $^1$H-NMR: δ [CDCl$_3$] |
|---|---|---|---|---|---|
| 3-386 | OCH$_2$CH$_2$SO$_2$Me | Et | 0 | CF(CF$_3$)$_2$ | |
| 3-387 | OCH$_2$CH$_2$SO$_2$Me | n-Pr | 0 | CF(CF$_3$)$_2$ | |
| 3-388 | OCH$_2$CH$_2$SO$_2$Me | i-Pr | 0 | CF(CF$_3$)$_2$ | |
| 3-389 | OCH$_2$CH$_2$SO$_2$Me | Me | 1 | CF(CF$_3$)$_2$ | |
| 3-390 | OCH$_2$CH$_2$SO$_2$Me | Et | 1 | CF(CF$_3$)$_2$ | |
| 3-391 | OCH$_2$CH$_2$SO$_2$Me | n-Pr | 1 | CF(CF$_3$)$_2$ | |
| 3-392 | OCH$_2$CH$_2$SO$_2$Me | i-Pr | 1 | CF(CF$_3$)$_2$ | |
| 3-393 | OCH$_2$CH$_2$SO$_2$Me | Me | 2 | CF(CF$_3$)$_2$ | |
| 3-394 | OCH$_2$CH$_2$SO$_2$Me | Et | 2 | CF(CF$_3$)$_2$ | |
| 3-395 | OCH$_2$CH$_2$SO$_2$Me | n-Pr | 2 | CF(CF$_3$)$_2$ | |
| 3-396 | OCH$_2$CH$_2$SO$_2$Me | i-Pr | 2 | CF(CF$_3$)$_2$ | |

TABLE 4

Compounds of the formula (I) according to the invention in which $R^2$ is hydroxyl, $R^3$, $R^4$, $R^5$, $R^7$ and $R^8$ are each hydrogen and $R^6$ is methyl.

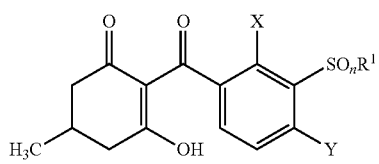

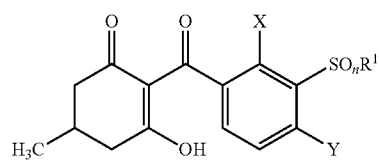

(I)

| No. | X | $R^1$ | n | Y | Physical data: $^1$H-NMR: δ [CDCl$_3$] |
|---|---|---|---|---|---|
| 4-1 | OH | Me | 0 | CF$_3$ | |
| 4-2 | OH | Et | 0 | CF$_3$ | |
| 4-3 | OH | n-Pr | 0 | CF$_3$ | |
| 4-4 | OH | i-Pr | 0 | CF$_3$ | |
| 4-5 | OH | Me | 1 | CF$_3$ | |
| 4-6 | OH | Et | 1 | CF$_3$ | |
| 4-7 | OH | n-Pr | 1 | CF$_3$ | |
| 4-8 | OH | i-Pr | 1 | CF$_3$ | |
| 4-9 | OH | Me | 2 | CF$_3$ | |
| 4-10 | OH | Et | 2 | CF$_3$ | |
| 4-11 | OH | n-Pr | 2 | CF$_3$ | |
| 4-12 | OH | i-Pr | 2 | CF$_3$ | |
| 4-13 | OMe | Me | 0 | CF$_3$ | 16.88 (s, 1H), 7.48 (d, 1H), 7.17 (d, 1H), 3.83 (s, 3H), 2.81 (m, 1H), 2.53-2.45 (m, 2H), 2.42 (s, 3H), 2.31 (m, 1H), 2.13 (dd, 1H), 1.13 (d, 3H) |
| 4-14 | OMe | Et | 0 | CF$_3$ | |
| 4-15 | OMe | n-Pr | 0 | CF$_3$ | |
| 4-16 | OMe | i-Pr | 0 | CF$_3$ | |
| 4-17 | OMe | Me | 1 | CF$_3$ | 16.68/16.57 (s, 1H), 7.54 (d, 1H), 7.41 (d/d, 1H), 3.86 (s/s, 3H), 3.06 (s/s, 3H), 2.84 (m, 1H), 2.60-2.04 (m, 4H), 1.13 (m, 3H) |
| 4-18 | OMe | Et | 1 | CF$_3$ | |
| 4-19 | OMe | n-Pr | 1 | CF$_3$ | |
| 4-20 | OMe | i-Pr | 1 | CF$_3$ | |
| 4-21 | OMe | Me | 2 | CF$_3$ | 16.61 (s, 1H), 7.71 (d, 1H), 7.50 (d, 1H), 3.83 (s, 3H), 3.30 (s, 3H), 2.85 (m, 1H), 2.56-2.46 (m, 2H), 2.32 (m, 1H), 2.15 (dd, 1H), 1.13 (d, 3H) |
| 4-22 | OMe | Et | 2 | CF$_3$ | |
| 4-23 | OMe | n-Pr | 2 | CF$_3$ | |
| 4-24 | OMe | i-Pr | 2 | CF$_3$ | |
| 4-25 | OEt | Me | 0 | CF$_3$ | |
| 4-26 | OEt | Et | 0 | CF$_3$ | |
| 4-27 | OEt | n-Pr | 0 | CF$_3$ | |
| 4-28 | OEt | i-Pr | 0 | CF$_3$ | |
| 4-29 | OEt | Me | 1 | CF$_3$ | |
| 4-30 | OEt | Et | 1 | CF$_3$ | |
| 4-31 | OEt | n-Pr | 1 | CF$_3$ | |
| 4-32 | OEt | i-Pr | 1 | CF$_3$ | |
| 4-33 | OEt | Me | 2 | CF$_3$ | |
| 4-34 | OEt | Et | 2 | CF$_3$ | |
| 4-35 | OEt | n-Pr | 2 | CF$_3$ | |
| 4-36 | OEt | i-Pr | 2 | CF$_3$ | |
| 4-37 | OCH$_2$-c-Pr | Me | 0 | CF$_3$ | |
| 4-38 | OCH$_2$-c-Pr | Et | 0 | CF$_3$ | |
| 4-39 | OCH$_2$-c-Pr | n-Pr | 0 | CF$_3$ | |
| 4-40 | OCH$_2$-c-Pr | i-Pr | 0 | CF$_3$ | |
| 4-41 | OCH$_2$-c-Pr | Me | 1 | CF$_3$ | |
| 4-42 | OCH$_2$-c-Pr | Et | 1 | CF$_3$ | |
| 4-43 | OCH$_2$-c-Pr | n-Pr | 1 | CF$_3$ | |
| 4-44 | OCH$_2$-c-Pr | i-Pr | 1 | CF$_3$ | |
| 4-45 | OCH$_2$-c-Pr | Me | 2 | CF$_3$ | |
| 4-46 | OCH$_2$-c-Pr | Et | 2 | CF$_3$ | |

TABLE 4-continued

Compounds of the formula (I) according to the invention in which $R^2$ is hydroxyl, $R^3$, $R^4$, $R^5$, $R^7$ and $R^8$ are each hydrogen and $R^6$ is methyl.

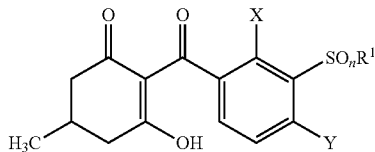

(I)

| No. | X | $R^1$ | n | Y | Physical data: $^1$H-NMR: δ [CDCl$_3$] |
|---|---|---|---|---|---|
| 4-47 | OCH$_2$-c-Pr | n-Pr | 2 | CF$_3$ | |
| 4-48 | OCH$_2$-c-Pr | i-Pr | 2 | CF$_3$ | |
| 4-49 | OCH$_2$CH$_2$OMe | Me | 0 | CF$_3$ | |
| 4-50 | OCH$_2$CH$_2$OMe | Et | 0 | CF$_3$ | |
| 4-51 | OCH$_2$CH$_2$OMe | n-Pr | 0 | CF$_3$ | |
| 4-52 | OCH$_2$CH$_2$OMe | i-Pr | 0 | CF$_3$ | |
| 4-53 | OCH$_2$CH$_2$OMe | Me | 1 | CF$_3$ | |
| 4-54 | OCH$_2$CH$_2$OMe | Et | 1 | CF$_3$ | |
| 4-55 | OCH$_2$CH$_2$OMe | n-Pr | 1 | CF$_3$ | |
| 4-56 | OCH$_2$CH$_2$OMe | i-Pr | 1 | CF$_3$ | |
| 4-57 | OCH$_2$CH$_2$OMe | Me | 2 | CF$_3$ | |
| 4-58 | OCH$_2$CH$_2$OMe | Et | 2 | CF$_3$ | |
| 4-59 | OCH$_2$CH$_2$OMe | n-Pr | 2 | CF$_3$ | |
| 4-60 | OCH$_2$CH$_2$OMe | i-Pr | 2 | CF$_3$ | |
| 4-61 | OCH$_2$CH$_2$SMe | Me | 0 | CF$_3$ | |
| 4-62 | OCH$_2$CH$_2$SMe | Et | 0 | CF$_3$ | |
| 4-63 | OCH$_2$CH$_2$SMe | n-Pr | 0 | CF$_3$ | |
| 4-64 | OCH$_2$CH$_2$SMe | i-Pr | 0 | CF$_3$ | |
| 4-65 | OCH$_2$CH$_2$SMe | Me | 1 | CF$_3$ | |
| 4-66 | OCH$_2$CH$_2$SMe | Et | 1 | CF$_3$ | |
| 4-67 | OCH$_2$CH$_2$SMe | n-Pr | 1 | CF$_3$ | |
| 4-68 | OCH$_2$CH$_2$SMe | i-Pr | 1 | CF$_3$ | |
| 4-69 | OCH$_2$CH$_2$SMe | Me | 2 | CF$_3$ | |
| 4-70 | OCH$_2$CH$_2$SMe | Et | 2 | CF$_3$ | |
| 4-71 | OCH$_2$CH$_2$SMe | n-Pr | 2 | CF$_3$ | |
| 4-72 | OCH$_2$CH$_2$SMe | i-Pr | 2 | CF$_3$ | |
| 4-73 | OCH$_2$CH$_2$SO$_2$Me | Me | 0 | CF$_3$ | |
| 4-74 | OCH$_2$CH$_2$SO$_2$Me | Et | 0 | CF$_3$ | |
| 4-75 | OCH$_2$CH$_2$SO$_2$Me | n-Pr | 0 | CF$_3$ | |
| 4-76 | OCH$_2$CH$_2$SO$_2$Me | i-Pr | 0 | CF$_3$ | |
| 4-77 | OCH$_2$CH$_2$SO$_2$Me | Me | 1 | CF$_3$ | |
| 4-78 | OCH$_2$CH$_2$SO$_2$Me | Et | 1 | CF$_3$ | |
| 4-79 | OCH$_2$CH$_2$SO$_2$Me | n-Pr | 1 | CF$_3$ | |
| 4-80 | OCH$_2$CH$_2$SO$_2$Me | i-Pr | 1 | CF$_3$ | |
| 4-81 | OCH$_2$CH$_2$SO$_2$Me | Me | 2 | CF$_3$ | |
| 4-82 | OCH$_2$CH$_2$SO$_2$Me | Et | 2 | CF$_3$ | |
| 4-83 | OCH$_2$CH$_2$SO$_2$Me | n-Pr | 2 | CF$_3$ | |
| 4-84 | OCH$_2$CH$_2$SO$_2$Me | i-Pr | 2 | CF$_3$ | |
| 4-85 | OCOMe | Me | 0 | CF$_3$ | |
| 4-86 | OCOMe | Et | 0 | CF$_3$ | |
| 4-87 | OCOMe | n-Pr | 0 | CF$_3$ | |
| 4-88 | OCOMe | i-Pr | 0 | CF$_3$ | |
| 4-89 | OCOMe | Me | 1 | CF$_3$ | |
| 4-90 | OCOMe | Et | 1 | CF$_3$ | |
| 4-91 | OCOMe | n-Pr | 1 | CF$_3$ | |
| 4-92 | OCOMe | i-Pr | 1 | CF$_3$ | |
| 4-93 | OCOMe | Me | 2 | CF$_3$ | |
| 4-94 | OCOMe | Et | 2 | CF$_3$ | |
| 4-95 | OCOMe | n-Pr | 2 | CF$_3$ | |
| 4-96 | OCOMe | i-Pr | 2 | CF$_3$ | |
| 4-97 | OSO$_2$Me | Me | 0 | CF$_3$ | |
| 4-98 | OSO$_2$Me | Et | 0 | CF$_3$ | |
| 4-99 | OSO$_2$Me | n-Pr | 0 | CF$_3$ | |
| 4-100 | OSO$_2$Me | i-Pr | 0 | CF$_3$ | |
| 4-101 | OSO$_2$Me | Me | 1 | CF$_3$ | |
| 4-102 | OSO$_2$Me | Et | 1 | CF$_3$ | |
| 4-103 | OSO$_2$Me | n-Pr | 1 | CF$_3$ | |
| 4-104 | OSO$_2$Me | i-Pr | 1 | CF$_3$ | |
| 4-105 | OSO$_2$Me | Me | 2 | CF$_3$ | |
| 4-106 | OSO$_2$Me | Et | 2 | CF$_3$ | |
| 4-107 | OSO$_2$Me | n-Pr | 2 | CF$_3$ | |
| 4-108 | OSO$_2$Me | i-Pr | 2 | CF$_3$ | |
| 4-109 | OMe | Me | 0 | C$_2$F$_5$ | |
| 4-110 | OMe | Et | 0 | C$_2$F$_5$ | |

TABLE 4-continued

Compounds of the formula (I) according to the invention in which $R^2$ is hydroxyl, $R^3$, $R^4$, $R^5$, $R^7$ and $R^8$ are each hydrogen and $R^6$ is methyl.

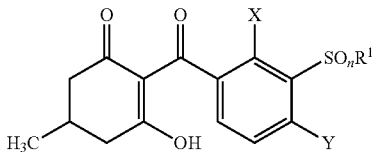

(I)

| No. | X | $R^1$ | n | Y | Physical data: $^1$H-NMR: δ [CDCl$_3$] |
|---|---|---|---|---|---|
| 4-111 | OMe | n-Pr | 0 | C$_2$F$_5$ | |
| 4-112 | OMe | i-Pr | 0 | C$_2$F$_5$ | |
| 4-113 | OMe | Me | 1 | C$_2$F$_5$ | |
| 4-114 | OMe | Et | 1 | C$_2$F$_5$ | |
| 4-115 | OMe | n-Pr | 1 | C$_2$F$_5$ | |
| 4-116 | OMe | i-Pr | 1 | C$_2$F$_5$ | |
| 4-117 | OMe | Me | 2 | C$_2$F$_5$ | |
| 4-118 | OMe | Et | 2 | C$_2$F$_5$ | |
| 4-119 | OMe | n-Pr | 2 | C$_2$F$_5$ | |
| 4-120 | OMe | i-Pr | 2 | C$_2$F$_5$ | |
| 4-121 | OEt | Me | 0 | C$_2$F$_5$ | |
| 4-122 | OEt | Et | 0 | C$_2$F$_5$ | |
| 4-123 | OEt | n-Pr | 0 | C$_2$F$_5$ | |
| 4-124 | OEt | i-Pr | 0 | C$_2$F$_5$ | |
| 4-125 | OEt | Me | 1 | C$_2$F$_5$ | |
| 4-126 | OEt | Et | 1 | C$_2$F$_5$ | |
| 4-127 | OEt | n-Pr | 1 | C$_2$F$_5$ | |
| 4-128 | OEt | i-Pr | 1 | C$_2$F$_5$ | |
| 4-129 | OEt | Me | 2 | C$_2$F$_5$ | |
| 4-130 | OEt | Et | 2 | C$_2$F$_5$ | |
| 4-131 | OEt | n-Pr | 2 | C$_2$F$_5$ | |
| 4-132 | OEt | i-Pr | 2 | C$_2$F$_5$ | |
| 4-133 | OCH$_2$-c-Pr | Me | 0 | C$_2$F$_5$ | |
| 4-134 | OCH$_2$-c-Pr | Et | 0 | C$_2$F$_5$ | |
| 4-135 | OCH$_2$-c-Pr | n-Pr | 0 | C$_2$F$_5$ | |
| 4-136 | OCH$_2$-c-Pr | i-Pr | 0 | C$_2$F$_5$ | |
| 4-137 | OCH$_2$-c-Pr | Me | 1 | C$_2$F$_5$ | |
| 4-138 | OCH$_2$-c-Pr | Et | 1 | C$_2$F$_5$ | |
| 4-139 | OCH$_2$-c-Pr | n-Pr | 1 | C$_2$F$_5$ | |
| 4-140 | OCH$_2$-c-Pr | i-Pr | 1 | C$_2$F$_5$ | |
| 4-141 | OCH$_2$-c-Pr | Me | 2 | C$_2$F$_5$ | |
| 4-142 | OCH$_2$-c-Pr | Et | 2 | C$_2$F$_5$ | |
| 4-143 | OCH$_2$-c-Pr | n-Pr | 2 | C$_2$F$_5$ | |
| 4-144 | OCH$_2$-c-Pr | i-Pr | 2 | C$_2$F$_5$ | |
| 4-145 | OCH$_2$CH$_2$OMe | Me | 0 | C$_2$F$_5$ | |
| 4-146 | OCH$_2$CH$_2$OMe | Et | 0 | C$_2$F$_5$ | |
| 4-147 | OCH$_2$CH$_2$OMe | n-Pr | 0 | C$_2$F$_5$ | |
| 4-148 | OCH$_2$CH$_2$OMe | i-Pr | 0 | C$_2$F$_5$ | |
| 4-149 | OCH$_2$CH$_2$OMe | Me | 1 | C$_2$F$_5$ | |
| 4-150 | OCH$_2$CH$_2$OMe | Et | 1 | C$_2$F$_5$ | |
| 4-151 | OCH$_2$CH$_2$OMe | n-Pr | 1 | C$_2$F$_5$ | |
| 4-152 | OCH$_2$CH$_2$OMe | i-Pr | 1 | C$_2$F$_5$ | |
| 4-153 | OCH$_2$CH$_2$OMe | Me | 2 | C$_2$F$_5$ | |
| 4-154 | OCH$_2$CH$_2$OMe | Et | 2 | C$_2$F$_5$ | |
| 4-155 | OCH$_2$CH$_2$OMe | n-Pr | 2 | C$_2$F$_5$ | |
| 4-156 | OCH$_2$CH$_2$OMe | i-Pr | 2 | C$_2$F$_5$ | |
| 4-157 | OCH$_2$CH$_2$SMe | Me | 0 | C$_2$F$_5$ | |
| 4-158 | OCH$_2$CH$_2$SMe | Et | 0 | C$_2$F$_5$ | |
| 4-159 | OCH$_2$CH$_2$SMe | n-Pr | 0 | C$_2$F$_5$ | |
| 4-160 | OCH$_2$CH$_2$SMe | i-Pr | 0 | C$_2$F$_5$ | |
| 4-161 | OCH$_2$CH$_2$SMe | Me | 1 | C$_2$F$_5$ | |
| 4-162 | OCH$_2$CH$_2$SMe | Et | 1 | C$_2$F$_5$ | |
| 4-163 | OCH$_2$CH$_2$SMe | n-Pr | 1 | C$_2$F$_5$ | |
| 4-164 | OCH$_2$CH$_2$SMe | i-Pr | 1 | C$_2$F$_5$ | |
| 4-165 | OCH$_2$CH$_2$SMe | Me | 2 | C$_2$F$_5$ | |
| 4-166 | OCH$_2$CH$_2$SMe | Et | 2 | C$_2$F$_5$ | |
| 4-167 | OCH$_2$CH$_2$SMe | n-Pr | 2 | C$_2$F$_5$ | |
| 4-168 | OCH$_2$CH$_2$SMe | i-Pr | 2 | C$_2$F$_5$ | |
| 4-169 | OCH$_2$CH$_2$SO$_2$Me | Me | 0 | C$_2$F$_5$ | |
| 4-170 | OCH$_2$CH$_2$SO$_2$Me | Et | 0 | C$_2$F$_5$ | |
| 4-171 | OCH$_2$CH$_2$SO$_2$Me | n-Pr | 0 | C$_2$F$_5$ | |
| 4-172 | OCH$_2$CH$_2$SO$_2$Me | i-Pr | 0 | C$_2$F$_5$ | |
| 4-173 | OCH$_2$CH$_2$SO$_2$Me | Me | 1 | C$_2$F$_5$ | |
| 4-174 | OCH$_2$CH$_2$SO$_2$Me | Et | 1 | C$_2$F$_5$ | |

TABLE 4-continued

Compounds of the formula (I) according to the invention in which $R^2$ is hydroxyl, $R^3$, $R^4$, $R^5$, $R^7$ and $R^8$ are each hydrogen and $R^6$ is methyl.

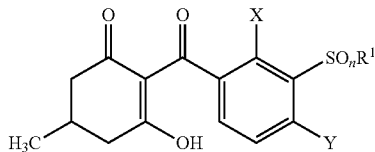

(I)

| No. | X | $R^1$ | n | Y | Physical data: $^1$H-NMR: δ [CDCl$_3$] |
|---|---|---|---|---|---|
| 4-175 | OCH$_2$CH$_2$SO$_2$Me | n-Pr | 1 | C$_2$F$_5$ | |
| 4-176 | OCH$_2$CH$_2$SO$_2$Me | i-Pr | 1 | C$_2$F$_5$ | |
| 4-177 | OCH$_2$CH$_2$SO$_2$Me | Me | 2 | C$_2$F$_5$ | |
| 4-178 | OCH$_2$CH$_2$SO$_2$Me | Et | 2 | C$_2$F$_5$ | |
| 4-179 | OCH$_2$CH$_2$SO$_2$Me | n-Pr | 2 | C$_2$F$_5$ | |
| 4-180 | OCH$_2$CH$_2$SO$_2$Me | i-Pr | 2 | C$_2$F$_5$ | |
| 4-181 | OMe | Me | 0 | CCl$_3$ | |
| 4-182 | OMe | Et | 0 | CCl$_3$ | |
| 4-183 | OMe | n-Pr | 0 | CCl$_3$ | |
| 4-184 | OMe | i-Pr | 0 | CCl$_3$ | |
| 4-185 | OMe | Me | 1 | CCl$_3$ | |
| 4-186 | OMe | Et | 1 | CCl$_3$ | |
| 4-187 | OMe | n-Pr | 1 | CCl$_3$ | |
| 4-188 | OMe | i-Pr | 1 | CCl$_3$ | |
| 4-189 | OMe | Me | 2 | CCl$_3$ | |
| 4-190 | OMe | Et | 2 | CCl$_3$ | |
| 4-191 | OMe | n-Pr | 2 | CCl$_3$ | |
| 4-192 | OMe | i-Pr | 2 | CCl$_3$ | |
| 4-193 | OEt | Me | 0 | CCl$_3$ | |
| 4-194 | OEt | Et | 0 | CCl$_3$ | |
| 4-195 | OEt | n-Pr | 0 | CCl$_3$ | |
| 4-196 | OEt | i-Pr | 0 | CCl$_3$ | |
| 4-197 | OEt | Me | 1 | CCl$_3$ | |
| 4-198 | OEt | Et | 1 | CCl$_3$ | |
| 4-199 | OEt | n-Pr | 1 | CCl$_3$ | |
| 4-200 | OEt | i-Pr | 1 | CCl$_3$ | |
| 4-201 | OEt | Me | 2 | CCl$_3$ | |
| 4-202 | OEt | Et | 2 | CCl$_3$ | |
| 4-203 | OEt | n-Pr | 2 | CCl$_3$ | |
| 4-204 | OEt | i-Pr | 2 | CCl$_3$ | |
| 4-205 | OCH$_2$-c-Pr | Me | 0 | CCl$_3$ | |
| 4-206 | OCH$_2$-c-Pr | Et | 0 | CCl$_3$ | |
| 4-207 | OCH$_2$-c-Pr | n-Pr | 0 | CCl$_3$ | |
| 4-208 | OCH$_2$-c-Pr | i-Pr | 0 | CCl$_3$ | |
| 4-209 | OCH$_2$-c-Pr | Me | 1 | CCl$_3$ | |
| 4-210 | OCH$_2$-c-Pr | Et | 1 | CCl$_3$ | |
| 4-211 | OCH$_2$-c-Pr | n-Pr | 1 | CCl$_3$ | |
| 4-212 | OCH$_2$-c-Pr | i-Pr | 1 | CCl$_3$ | |
| 4-213 | OCH$_2$-c-Pr | Me | 2 | CCl$_3$ | |
| 4-214 | OCH$_2$-c-Pr | Et | 2 | CCl$_3$ | |
| 4-215 | OCH$_2$-c-Pr | n-Pr | 2 | CCl$_3$ | |
| 4-216 | OCH$_2$-c-Pr | i-Pr | 2 | CCl$_3$ | |
| 4-217 | OCH$_2$CH$_2$OMe | Me | 0 | CCl$_3$ | |
| 4-218 | OCH$_2$CH$_2$OMe | Et | 0 | CCl$_3$ | |
| 4-219 | OCH$_2$CH$_2$OMe | n-Pr | 0 | CCl$_3$ | |
| 4-220 | OCH$_2$CH$_2$OMe | i-Pr | 0 | CCl$_3$ | |
| 4-221 | OCH$_2$CH$_2$OMe | Me | 1 | CCl$_3$ | |
| 4-222 | OCH$_2$CH$_2$OMe | Et | 1 | CCl$_3$ | |
| 4-223 | OCH$_2$CH$_2$OMe | n-Pr | 1 | CCl$_3$ | |
| 4-224 | OCH$_2$CH$_2$OMe | i-Pr | 1 | CCl$_3$ | |
| 4-225 | OCH$_2$CH$_2$OMe | Me | 2 | CCl$_3$ | |
| 4-226 | OCH$_2$CH$_2$OMe | Et | 2 | CCl$_3$ | |
| 4-227 | OCH$_2$CH$_2$OMe | n-Pr | 2 | CCl$_3$ | |
| 4-228 | OCH$_2$CH$_2$OMe | i-Pr | 2 | CCl$_3$ | |
| 4-229 | OCH$_2$CH$_2$SMe | Me | 0 | CCl$_3$ | |
| 4-230 | OCH$_2$CH$_2$SMe | Et | 0 | CCl$_3$ | |
| 4-231 | OCH$_2$CH$_2$SMe | n-Pr | 0 | CCl$_3$ | |
| 4-232 | OCH$_2$CH$_2$SMe | i-Pr | 0 | CCl$_3$ | |
| 4-233 | OCH$_2$CH$_2$SMe | Me | 1 | CCl$_3$ | |
| 4-234 | OCH$_2$CH$_2$SMe | Et | 1 | CCl$_3$ | |
| 4-235 | OCH$_2$CH$_2$SMe | n-Pr | 1 | CCl$_3$ | |
| 4-236 | OCH$_2$CH$_2$SMe | i-Pr | 1 | CCl$_3$ | |
| 4-237 | OCH$_2$CH$_2$SMe | Me | 2 | CCl$_3$ | |
| 4-238 | OCH$_2$CH$_2$SMe | Et | 2 | CCl$_3$ | |

TABLE 4-continued

Compounds of the formula (I) according to the invention in which $R^2$ is hydroxyl, $R^3$, $R^4$, $R^5$, $R^7$ and $R^8$ are each hydrogen and $R^6$ is methyl.

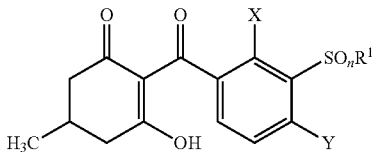

(I)

| No. | X | $R^1$ | n | Y | Physical data: $^1$H-NMR: δ [CDCl$_3$] |
|---|---|---|---|---|---|
| 4-239 | OCH$_2$CH$_2$SMe | n-Pr | 2 | CCl$_3$ | |
| 4-240 | OCH$_2$CH$_2$SMe | i-Pr | 2 | CCl$_3$ | |
| 4-241 | OCH$_2$CH$_2$SO$_2$Me | Me | 0 | CCl$_3$ | |
| 4-242 | OCH$_2$CH$_2$SO$_2$Me | Et | 0 | CCl$_3$ | |
| 4-243 | OCH$_2$CH$_2$SO$_2$Me | n-Pr | 0 | CCl$_3$ | |
| 4-244 | OCH$_2$CH$_2$SO$_2$Me | i-Pr | 0 | CCl$_3$ | |
| 4-245 | OCH$_2$CH$_2$SO$_2$Me | Me | 1 | CCl$_3$ | |
| 4-246 | OCH$_2$CH$_2$SO$_2$Me | Et | 1 | CCl$_3$ | |
| 4-247 | OCH$_2$CH$_2$SO$_2$Me | n-Pr | 1 | CCl$_3$ | |
| 4-248 | OCH$_2$CH$_2$SO$_2$Me | i-Pr | 1 | CCl$_3$ | |
| 4-249 | OCH$_2$CH$_2$SO$_2$Me | Me | 2 | CCl$_3$ | |
| 4-250 | OCH$_2$CH$_2$SO$_2$Me | Et | 2 | CCl$_3$ | |
| 4-251 | OCH$_2$CH$_2$SO$_2$Me | n-Pr | 2 | CCl$_3$ | |
| 4-252 | OCH$_2$CH$_2$SO$_2$Me | i-Pr | 2 | CCl$_3$ | |
| 4-253 | OMe | Me | 0 | CHF$_2$ | |
| 4-254 | OMe | Et | 0 | CHF$_2$ | |
| 4-255 | OMe | n-Pr | 0 | CHF$_2$ | |
| 4-256 | OMe | i-Pr | 0 | CHF$_2$ | |
| 4-257 | OMe | Me | 1 | CHF$_2$ | |
| 4-258 | OMe | Et | 1 | CHF$_2$ | |
| 4-259 | OMe | n-Pr | 1 | CHF$_2$ | |
| 4-260 | OMe | i-Pr | 1 | CHF$_2$ | |
| 4-261 | OMe | Me | 2 | CHF$_2$ | |
| 4-262 | OMe | Et | 2 | CHF$_2$ | |
| 4-263 | OMe | n-Pr | 2 | CHF$_2$ | |
| 4-264 | OMe | i-Pr | 2 | CHF$_2$ | |
| 4-265 | OEt | Me | 0 | CHF$_2$ | |
| 4-266 | OEt | Et | 0 | CHF$_2$ | |
| 4-267 | OEt | n-Pr | 0 | CHF$_2$ | |
| 4-268 | OEt | i-Pr | 0 | CHF$_2$ | |
| 4-269 | OEt | Me | 1 | CHF$_2$ | |
| 4-270 | OEt | Et | 1 | CHF$_2$ | |
| 4-271 | OEt | n-Pr | 1 | CHF$_2$ | |
| 4-272 | OEt | i-Pr | 1 | CHF$_2$ | |
| 4-273 | OEt | Me | 2 | CHF$_2$ | |
| 4-274 | OEt | Et | 2 | CHF$_2$ | |
| 4-275 | OEt | n-Pr | 2 | CHF$_2$ | |
| 4-276 | OEt | i-Pr | 2 | CHF$_2$ | |
| 4-277 | OCH$_2$-c-Pr | Me | 0 | CHF$_2$ | |
| 4-278 | OCH$_2$-c-Pr | Et | 0 | CHF$_2$ | |
| 4-279 | OCH$_2$-c-Pr | n-Pr | 0 | CHF$_2$ | |
| 4-280 | OCH$_2$-c-Pr | i-Pr | 0 | CHF$_2$ | |
| 4-281 | OCH$_2$-c-Pr | Me | 1 | CHF$_2$ | |
| 4-282 | OCH$_2$-c-Pr | Et | 1 | CHF$_2$ | |
| 4-283 | OCH$_2$-c-Pr | n-Pr | 1 | CHF$_2$ | |
| 4-284 | OCH$_2$-c-Pr | i-Pr | 1 | CHF$_2$ | |
| 4-285 | OCH$_2$-c-Pr | Me | 2 | CHF$_2$ | |
| 4-286 | OCH$_2$-c-Pr | Et | 2 | CHF$_2$ | |
| 4-287 | OCH$_2$-c-Pr | n-Pr | 2 | CHF$_2$ | |
| 4-288 | OCH$_2$-c-Pr | i-Pr | 2 | CHF$_2$ | |
| 4-289 | OCH$_2$CH$_2$OMe | Me | 0 | CHF$_2$ | |
| 4-290 | OCH$_2$CH$_2$OMe | Et | 0 | CHF$_2$ | |
| 4-291 | OCH$_2$CH$_2$OMe | n-Pr | 0 | CHF$_2$ | |
| 4-292 | OCH$_2$CH$_2$OMe | i-Pr | 0 | CHF$_2$ | |
| 4-293 | OCH$_2$CH$_2$OMe | Me | 1 | CHF$_2$ | |
| 4-294 | OCH$_2$CH$_2$OMe | Et | 1 | CHF$_2$ | |
| 4-295 | OCH$_2$CH$_2$OMe | n-Pr | 1 | CHF$_2$ | |
| 4-296 | OCH$_2$CH$_2$OMe | i-Pr | 1 | CHF$_2$ | |
| 4-297 | OCH$_2$CH$_2$OMe | Me | 2 | CHF$_2$ | |
| 4-298 | OCH$_2$CH$_2$OMe | Et | 2 | CHF$_2$ | |
| 4-299 | OCH$_2$CH$_2$OMe | n-Pr | 2 | CHF$_2$ | |
| 4-300 | OCH$_2$CH$_2$OMe | i-Pr | 2 | CHF$_2$ | |
| 4-301 | OCH$_2$CH$_2$SMe | Me | 0 | CHF$_2$ | |
| 4-302 | OCH$_2$CH$_2$SMe | Et | 0 | CHF$_2$ | |

TABLE 4-continued

Compounds of the formula (I) according to the invention in which $R^2$ is hydroxyl, $R^3$, $R^4$, $R^5$, $R^7$ and $R^8$ are each hydrogen and $R^6$ is methyl.

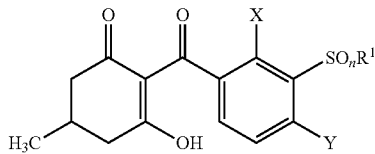

(I)

| No. | X | $R^1$ | n | Y | Physical data: $^1$H-NMR: δ [CDCl$_3$] |
|---|---|---|---|---|---|
| 4-303 | OCH$_2$CH$_2$SMe | n-Pr | 0 | CHF$_2$ | |
| 4-304 | OCH$_2$CH$_2$SMe | i-Pr | 0 | CHF$_2$ | |
| 4-305 | OCH$_2$CH$_2$SMe | Me | 1 | CHF$_2$ | |
| 4-306 | OCH$_2$CH$_2$SMe | Et | 1 | CHF$_2$ | |
| 4-307 | OCH$_2$CH$_2$SMe | n-Pr | 1 | CHF$_2$ | |
| 4-308 | OCH$_2$CH$_2$SMe | i-Pr | 1 | CHF$_2$ | |
| 4-309 | OCH$_2$CH$_2$SMe | Me | 2 | CHF$_2$ | |
| 4-310 | OCH$_2$CH$_2$SMe | Et | 2 | CHF$_2$ | |
| 4-311 | OCH$_2$CH$_2$SMe | n-Pr | 2 | CHF$_2$ | |
| 4-312 | OCH$_2$CH$_2$SMe | i-Pr | 2 | CHF$_2$ | |
| 4-313 | OCH$_2$CH$_2$SO$_2$Me | Me | 0 | CHF$_2$ | |
| 4-314 | OCH$_2$CH$_2$SO$_2$Me | Et | 0 | CHF$_2$ | |
| 4-315 | OCH$_2$CH$_2$SO$_2$Me | n-Pr | 0 | CHF$_2$ | |
| 4-316 | OCH$_2$CH$_2$SO$_2$Me | i-Pr | 0 | CHF$_2$ | |
| 4-317 | OCH$_2$CH$_2$SO$_2$Me | Me | 1 | CHF$_2$ | |
| 4-318 | OCH$_2$CH$_2$SO$_2$Me | Et | 1 | CHF$_2$ | |
| 4-319 | OCH$_2$CH$_2$SO$_2$Me | n-Pr | 1 | CHF$_2$ | |
| 4-320 | OCH$_2$CH$_2$SO$_2$Me | i-Pr | 1 | CHF$_2$ | |
| 4-321 | OCH$_2$CH$_2$SO$_2$Me | Me | 2 | CHF$_2$ | |
| 4-322 | OCH$_2$CH$_2$SO$_2$Me | Et | 2 | CHF$_2$ | |
| 4-323 | OCH$_2$CH$_2$SO$_2$Me | n-Pr | 2 | CHF$_2$ | |
| 4-324 | OCH$_2$CH$_2$SO$_2$Me | i-Pr | 2 | CHF$_2$ | |
| 4-325 | OMe | Me | 0 | CF(CF$_3$)$_2$ | |
| 4-326 | OMe | Et | 0 | CF(CF$_3$)$_2$ | |
| 4-327 | OMe | n-Pr | 0 | CF(CF$_3$)$_2$ | |
| 4-328 | OMe | i-Pr | 0 | CF(CF$_3$)$_2$ | |
| 4-329 | OMe | Me | 1 | CF(CF$_3$)$_2$ | |
| 4-330 | OMe | Et | 1 | CF(CF$_3$)$_2$ | |
| 4-331 | OMe | n-Pr | 1 | CF(CF$_3$)$_2$ | |
| 4-332 | OMe | i-Pr | 1 | CF(CF$_3$)$_2$ | |
| 4-333 | OMe | Me | 2 | CF(CF$_3$)$_2$ | |
| 4-334 | OMe | Et | 2 | CF(CF$_3$)$_2$ | |
| 4-335 | OMe | n-Pr | 2 | CF(CF$_3$)$_2$ | |
| 4-336 | OMe | i-Pr | 2 | CF(CF$_3$)$_2$ | |
| 4-337 | OEt | Me | 0 | CF(CF$_3$)$_2$ | |
| 4-338 | OEt | Et | 0 | CF(CF$_3$)$_2$ | |
| 4-339 | OEt | n-Pr | 0 | CF(CF$_3$)$_2$ | |
| 4-340 | OEt | i-Pr | 0 | CF(CF$_3$)$_2$ | |
| 4-341 | OEt | Me | 1 | CF(CF$_3$)$_2$ | |
| 4-342 | OEt | Et | 1 | CF(CF$_3$)$_2$ | |
| 4-343 | OEt | n-Pr | 1 | CF(CF$_3$)$_2$ | |
| 4-344 | OEt | i-Pr | 1 | CF(CF$_3$)$_2$ | |
| 4-345 | OEt | Me | 2 | CF(CF$_3$)$_2$ | |
| 4-346 | OEt | Et | 2 | CF(CF$_3$)$_2$ | |
| 4-347 | OEt | n-Pr | 2 | CF(CF$_3$)$_2$ | |
| 4-348 | OEt | i-Pr | 2 | CF(CF$_3$)$_2$ | |
| 4-349 | O—CH$_2$—c-Pr | Me | 0 | CF(CF$_3$)$_2$ | |
| 4-350 | O—CH$_2$—c-Pr | Et | 0 | CF(CF$_3$)$_2$ | |
| 4-351 | O—CH$_2$—c-Pr | n-Pr | 0 | CF(CF$_3$)$_2$ | |
| 4-352 | O—CH$_2$—c-Pr | i-Pr | 0 | CF(CF$_3$)$_2$ | |
| 4-353 | O—CH$_2$—c-Pr | Me | 1 | CF(CF$_3$)$_2$ | |
| 4-354 | O—CH$_2$—c-Pr | Et | 1 | CF(CF$_3$)$_2$ | |
| 4-355 | O—CH$_2$—c-Pr | n-Pr | 1 | CF(CF$_3$)$_2$ | |
| 4-356 | O—CH$_2$—c-Pr | i-Pr | 1 | CF(CF$_3$)$_2$ | |
| 4-357 | O—CH$_2$—c-Pr | Me | 2 | CF(CF$_3$)$_2$ | |
| 4-358 | O—CH$_2$—c-Pr | Et | 2 | CF(CF$_3$)$_2$ | |
| 4-359 | O—CH$_2$—c-Pr | n-Pr | 2 | CF(CF$_3$)$_2$ | |
| 4-360 | O—CH$_2$—c-Pr | i-Pr | 2 | CF(CF$_3$)$_2$ | |
| 4-361 | OCH$_2$CH$_2$OMe | Me | 0 | CF(CF$_3$)$_2$ | |
| 4-362 | OCH$_2$CH$_2$OMe | Et | 0 | CF(CF$_3$)$_2$ | |
| 4-363 | OCH$_2$CH$_2$OMe | n-Pr | 0 | CF(CF$_3$)$_2$ | |
| 4-364 | OCH$_2$CH$_2$OMe | i-Pr | 0 | CF(CF$_3$)$_2$ | |
| 4-365 | OCH$_2$CH$_2$OMe | Me | 1 | CF(CF$_3$)$_2$ | |
| 4-366 | OCH$_2$CH$_2$OMe | Et | 1 | CF(CF$_3$)$_2$ | |

TABLE 4-continued

Compounds of the formula (I) according to the invention in which $R^2$ is hydroxyl, $R^3$, $R^4$, $R^5$, $R^7$ and $R^8$ are each hydrogen and $R^6$ is methyl.

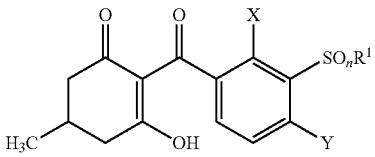

(I)

| No. | X | $R^1$ | n | Y | Physical data: $^1$H-NMR: δ [CDCl$_3$] |
|---|---|---|---|---|---|
| 4-367 | OCH$_2$CH$_2$OMe | n-Pr | 1 | CF(CF$_3$)$_2$ | |
| 4-368 | OCH$_2$CH$_2$OMe | i-Pr | 1 | CF(CF$_3$)$_2$ | |
| 4-369 | OCH$_2$CH$_2$OMe | Me | 2 | CF(CF$_3$)$_2$ | |
| 4-370 | OCH$_2$CH$_2$OMe | Et | 2 | CF(CF$_3$)$_2$ | |
| 4-371 | OCH$_2$CH$_2$OMe | n-Pr | 2 | CF(CF$_3$)$_2$ | |
| 4-372 | OCH$_2$CH$_2$OMe | i-Pr | 2 | CF(CF$_3$)$_2$ | |
| 4-373 | OCH$_2$CH$_2$SMe | Me | 0 | CF(CF$_3$)$_2$ | |
| 4-374 | OCH$_2$CH$_2$SMe | Et | 0 | CF(CF$_3$)$_2$ | |
| 4-375 | OCH$_2$CH$_2$SMe | n-Pr | 0 | CF(CF$_3$)$_2$ | |
| 4-376 | OCH$_2$CH$_2$SMe | i-Pr | 0 | CF(CF$_3$)$_2$ | |
| 4-377 | OCH$_2$CH$_2$SMe | Me | 1 | CF(CF$_3$)$_2$ | |
| 4-378 | OCH$_2$CH$_2$SMe | Et | 1 | CF(CF$_3$)$_2$ | |
| 4-379 | OCH$_2$CH$_2$SMe | n-Pr | 1 | CF(CF$_3$)$_2$ | |
| 4-380 | OCH$_2$CH$_2$SMe | i-Pr | 1 | CF(CF$_3$)$_2$ | |
| 4-381 | OCH$_2$CH$_2$SMe | Me | 2 | CF(CF$_3$)$_2$ | |
| 4-382 | OCH$_2$CH$_2$SMe | Et | 2 | CF(CF$_3$)$_2$ | |
| 4-383 | OCH$_2$CH$_2$SMe | n-Pr | 2 | CF(CF$_3$)$_2$ | |
| 4-384 | OCH$_2$CH$_2$SMe | i-Pr | 2 | CF(CF$_3$)$_2$ | |
| 4-385 | OCH$_2$CH$_2$SO$_2$Me | Me | 0 | CF(CF$_3$)$_2$ | |
| 4-386 | OCH$_2$CH$_2$SO$_2$Me | Et | 0 | CF(CF$_3$)$_2$ | |
| 4-387 | OCH$_2$CH$_2$SO$_2$Me | n-Pr | 0 | CF(CF$_3$)$_2$ | |
| 4-388 | OCH$_2$CH$_2$SO$_2$Me | i-Pr | 0 | CF(CF$_3$)$_2$ | |
| 4-389 | OCH$_2$CH$_2$SO$_2$Me | Me | 1 | CF(CF$_3$)$_2$ | |
| 4-390 | OCH$_2$CH$_2$SO$_2$Me | Et | 1 | CF(CF$_3$)$_2$ | |
| 4-391 | OCH$_2$CH$_2$SO$_2$Me | n-Pr | 1 | CF(CF$_3$)$_2$ | |
| 4-392 | OCH$_2$CH$_2$SO$_2$Me | i-Pr | 1 | CF(CF$_3$)$_2$ | |
| 4-393 | OCH$_2$CH$_2$SO$_2$Me | Me | 2 | CF(CF$_3$)$_2$ | |
| 4-394 | OCH$_2$CH$_2$SO$_2$Me | Et | 2 | CF(CF$_3$)$_2$ | |
| 4-395 | OCH$_2$CH$_2$SO$_2$Me | n-Pr | 2 | CF(CF$_3$)$_2$ | |
| 4-396 | OCH$_2$CH$_2$SO$_2$Me | i-Pr | 2 | CF(CF$_3$)$_2$ | |

TABLE 5

Compounds of the formula (I) according to the invention in which $R^2$ is hydroxyl, $R^4$, $R^5$, $R^6$ and $R^7$ are each hydrogen and $R^3$ and $R^8$ together are an ethylene group.

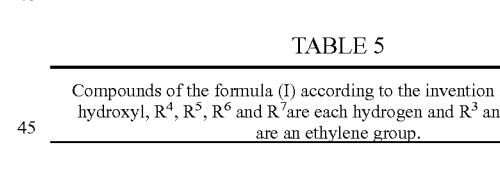

(I)

| No. | X | $R^1$ | n | Y | Physical data: $^1$H-NMR: δ [CDCl$_3$] |
|---|---|---|---|---|---|
| 5-1 | OH | Me | 0 | CF$_3$ | |
| 5-2 | OH | Et | 0 | CF$_3$ | |
| 5-3 | OH | n-Pr | 0 | CF$_3$ | |
| 5-4 | OH | i-Pr | 0 | CF$_3$ | |
| 5-5 | OH | Me | 1 | CF$_3$ | |
| 5-6 | OH | Et | 1 | CF$_3$ | |
| 5-7 | OH | n-Pr | 1 | CF$_3$ | |
| 5-8 | OH | i-Pr | 1 | CF$_3$ | |
| 5-9 | OH | Me | 2 | CF$_3$ | |
| 5-10 | OH | Et | 2 | CF$_3$ | |
| 5-11 | OH | n-Pr | 2 | CF$_3$ | |
| 5-12 | OH | i-Pr | 2 | CF$_3$ | |
| 5-13 | OMe | Me | 0 | CF$_3$ | |

TABLE 5-continued

Compounds of the formula (I) according to the invention in which $R^2$ is hydroxyl, $R^4$, $R^5$, $R^6$ and $R^7$ are each hydrogen and $R^3$ and $R^8$ together are an ethylene group.

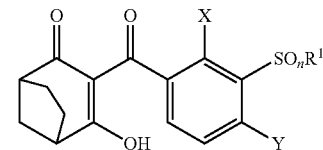

(I)

| No. | X | $R^1$ | n | Y | Physical data: $^1$H-NMR: δ [CDCl$_3$] |
|---|---|---|---|---|---|
| 5-14 | OMe | Et | 0 | CF$_3$ | |
| 5-15 | OMe | n-Pr | 0 | CF$_3$ | |
| 5-16 | OMe | i-Pr | 0 | CF$_3$ | |
| 5-17 | OMe | Me | 1 | CF$_3$ | 16.68 (s, 1H), 7.56 (m, 1H), 7.42 (d, 1H), 3.85/3.83 (s, 3H), 3.17 (m, 1H), 3.09/3.07 (s, 3H), 2.92 (m, 1H), 2.32-1.62 (m, 6H) |
| 5-18 | OMe | Et | 1 | CF$_3$ | |
| 5-19 | OMe | n-Pr | 1 | CF$_3$ | |
| 5-20 | OMe | i-Pr | 1 | CF$_3$ | |
| 5-21 | OMe | Me | 2 | CF$_3$ | 16.68 (s, 1H), 7.72 (d, 1H), 7.53 (d, 1H), 3.82 (s, 3H), 3.31 (s, 3H), 3.18 (m, 1H), 2.91 (m, 1H), 2.32-2.12 (m, 3H), 2.03 (m, 1H), 1.81-1.71 (m, 2H) |
| 5-22 | OMe | Et | 2 | CF$_3$ | |
| 5-23 | OMe | n-Pr | 2 | CF$_3$ | |
| 5-24 | OMe | i-Pr | 2 | CF$_3$ | |
| 5-25 | OEt | Me | 0 | CF$_3$ | |
| 5-26 | OEt | Et | 0 | CF$_3$ | |
| 5-27 | OEt | n-Pr | 0 | CF$_3$ | |
| 5-28 | OEt | i-Pr | 0 | CF$_3$ | |
| 5-29 | OEt | Me | 1 | CF$_3$ | |
| 5-30 | OEt | Et | 1 | CF$_3$ | |
| 5-31 | OEt | n-Pr | 1 | CF$_3$ | |
| 5-32 | OEt | i-Pr | 1 | CF$_3$ | |
| 5-33 | OEt | Me | 2 | CF$_3$ | |
| 5-34 | OEt | Et | 2 | CF$_3$ | |
| 5-35 | OEt | n-Pr | 2 | CF$_3$ | |
| 5-36 | OEt | i-Pr | 2 | CF$_3$ | |
| 5-37 | O—CH$_2$—c-Pr | Me | 0 | CF$_3$ | |
| 5-38 | O—CH$_2$—c-Pr | Et | 0 | CF$_3$ | |
| 5-39 | O—CH$_2$—c-Pr | n-Pr | 0 | CF$_3$ | |
| 5-40 | O—CH$_2$—c-Pr | i-Pr | 0 | CF$_3$ | |
| 5-41 | O—CH$_2$—c-Pr | Me | 1 | CF$_3$ | |
| 5-42 | O—CH$_2$—c-Pr | Et | 1 | CF$_3$ | |
| 5-43 | O—CH$_2$—c-Pr | n-Pr | 1 | CF$_3$ | |
| 5-44 | O—CH$_2$—c-Pr | i-Pr | 1 | CF$_3$ | |
| 5-45 | O—CH$_2$—c-Pr | Me | 2 | CF$_3$ | |
| 5-46 | O—CH$_2$—c-Pr | Et | 2 | CF$_3$ | |
| 5-47 | O—CH$_2$—c-Pr | n-Pr | 2 | CF$_3$ | |
| 5-48 | O—CH$_2$—c-Pr | i-Pr | 2 | CF$_3$ | |
| 5-49 | OCH$_2$CH$_2$OMe | Me | 0 | CF$_3$ | |
| 5-50 | OCH$_2$CH$_2$OMe | Et | 0 | CF$_3$ | |
| 5-51 | OCH$_2$CH$_2$OMe | n-Pr | 0 | CF$_3$ | |
| 5-52 | OCH$_2$CH$_2$OMe | i-Pr | 0 | CF$_3$ | |
| 5-53 | OCH$_2$CH$_2$OMe | Me | 1 | CF$_3$ | |
| 5-54 | OCH$_2$CH$_2$OMe | Et | 1 | CF$_3$ | |
| 5-55 | OCH$_2$CH$_2$OMe | n-Pr | 1 | CF$_3$ | |
| 5-56 | OCH$_2$CH$_2$OMe | i-Pr | 1 | CF$_3$ | |
| 5-57 | OCH$_2$CH$_2$OMe | Me | 2 | CF$_3$ | |
| 5-58 | OCH$_2$CH$_2$OMe | Et | 2 | CF$_3$ | |
| 5-59 | OCH$_2$CH$_2$OMe | n-Pr | 2 | CF$_3$ | |
| 5-60 | OCH$_2$CH$_2$OMe | i-Pr | 2 | CF$_3$ | |
| 5-61 | OCH$_2$CH$_2$SMe | Me | 0 | CF$_3$ | |
| 5-62 | OCH$_2$CH$_2$SMe | Et | 0 | CF$_3$ | |
| 5-63 | OCH$_2$CH$_2$SMe | n-Pr | 0 | CF$_3$ | |
| 5-64 | OCH$_2$CH$_2$SMe | i-Pr | 0 | CF$_3$ | |
| 5-65 | OCH$_2$CH$_2$SMe | Me | 1 | CF$_3$ | |
| 5-66 | OCH$_2$CH$_2$SMe | Et | 1 | CF$_3$ | |
| 5-67 | OCH$_2$CH$_2$SMe | n-Pr | 1 | CF$_3$ | |
| 5-68 | OCH$_2$CH$_2$SMe | i-Pr | 1 | CF$_3$ | |
| 5-69 | OCH$_2$CH$_2$SMe | Me | 2 | CF$_3$ | |
| 5-70 | OCH$_2$CH$_2$SMe | Et | 2 | CF$_3$ | |
| 5-71 | OCH$_2$CH$_2$SMe | n-Pr | 2 | CF$_3$ | |
| 5-72 | OCH$_2$CH$_2$SMe | i-Pr | 2 | CF$_3$ | |
| 5-73 | OCH$_2$CH$_2$SO$_2$Me | Me | 0 | CF$_3$ | |
| 5-74 | OCH$_2$CH$_2$SO$_2$Me | Et | 0 | CF$_3$ | |
| 5-75 | OCH$_2$CH$_2$SO$_2$Me | n-Pr | 0 | CF$_3$ | |
| 5-76 | OCH$_2$CH$_2$SO$_2$Me | i-Pr | 0 | CF$_3$ | |
| 5-77 | OCH$_2$CH$_2$SO$_2$Me | Me | 1 | CF$_3$ | |
| 5-78 | OCH$_2$CH$_2$SO$_2$Me | Et | 1 | CF$_3$ | |
| 5-79 | OCH$_2$CH$_2$SO$_2$Me | n-Pr | 1 | CF$_3$ | |
| 5-80 | OCH$_2$CH$_2$SO$_2$Me | i-Pr | 1 | CF$_3$ | |
| 5-81 | OCH$_2$CH$_2$SO$_2$Me | Me | 2 | CF$_3$ | |
| 5-82 | OCH$_2$CH$_2$SO$_2$Me | Et | 2 | CF$_3$ | |
| 5-83 | OCH$_2$CH$_2$SO$_2$Me | n-Pr | 2 | CF$_3$ | |
| 5-84 | OCH$_2$CH$_2$SO$_2$Me | i-Pr | 2 | CF$_3$ | |
| 5-85 | OCOMe | Me | 0 | CF$_3$ | |
| 5-86 | OCOMe | Et | 0 | CF$_3$ | |
| 5-87 | OCOMe | n-Pr | 0 | CF$_3$ | |
| 5-88 | OCOMe | i-Pr | 0 | CF$_3$ | |
| 5-89 | OCOMe | Me | 1 | CF$_3$ | |
| 5-90 | OCOMe | Et | 1 | CF$_3$ | |
| 5-91 | OCOMe | n-Pr | 1 | CF$_3$ | |
| 5-92 | OCOMe | i-Pr | 1 | CF$_3$ | |
| 5-93 | OCOMe | Me | 2 | CF$_3$ | |
| 5-94 | OCOMe | Et | 2 | CF$_3$ | |
| 5-95 | OCOMe | n-Pr | 2 | CF$_3$ | |
| 5-96 | OCOMe | i-Pr | 2 | CF$_3$ | |
| 5-97 | OSO$_2$Me | Me | 0 | CF$_3$ | |
| 5-98 | OSO$_2$Me | Et | 0 | CF$_3$ | |
| 5-99 | OSO$_2$Me | n-Pr | 0 | CF$_3$ | |
| 5-100 | OSO$_2$Me | i-Pr | 0 | CF$_3$ | |
| 5-101 | OSO$_2$Me | Me | 1 | CF$_3$ | |
| 5-102 | OSO$_2$Me | Et | 1 | CF$_3$ | |
| 5-103 | OSO$_2$Me | n-Pr | 1 | CF$_3$ | |
| 5-104 | OSO$_2$Me | i-Pr | 1 | CF$_3$ | |
| 5-105 | OSO$_2$Me | Me | 2 | CF$_3$ | |
| 5-106 | OSO$_2$Me | Et | 2 | CF$_3$ | |
| 5-107 | OSO$_2$Me | n-Pr | 2 | CF$_3$ | |
| 5-108 | OSO$_2$Me | i-Pr | 2 | CF$_3$ | |
| 5-109 | OMe | Me | 0 | C$_2$F$_5$ | |
| 5-110 | OMe | Et | 0 | C$_2$F$_5$ | |
| 5-111 | OMe | n-Pr | 0 | C$_2$F$_5$ | |
| 5-112 | OMe | i-Pr | 0 | C$_2$F$_5$ | |
| 5-113 | OMe | Me | 1 | C$_2$F$_5$ | |
| 5-114 | OMe | Et | 1 | C$_2$F$_5$ | |
| 5-115 | OMe | n-Pr | 1 | C$_2$F$_5$ | |
| 5-116 | OMe | i-Pr | 1 | C$_2$F$_5$ | |
| 5-117 | OMe | Me | 2 | C$_2$F$_5$ | |
| 5-118 | OMe | Et | 2 | C$_2$F$_5$ | |
| 5-119 | OMe | n-Pr | 2 | C$_2$F$_5$ | |
| 5-120 | OMe | i-Pr | 2 | C$_2$F$_5$ | |
| 5-121 | OEt | Me | 0 | C$_2$F$_5$ | |
| 5-122 | OEt | Et | 0 | C$_2$F$_5$ | |
| 5-123 | OEt | n-Pr | 0 | C$_2$F$_5$ | |
| 5-124 | OEt | i-Pr | 0 | C$_2$F$_5$ | |
| 5-125 | OEt | Me | 1 | C$_2$F$_5$ | |
| 5-126 | OEt | Et | 1 | C$_2$F$_5$ | |
| 5-127 | OEt | n-Pr | 1 | C$_2$F$_5$ | |
| 5-128 | OEt | i-Pr | 1 | C$_2$F$_5$ | |
| 5-129 | OEt | Me | 2 | C$_2$F$_5$ | |
| 5-130 | OEt | Et | 2 | C$_2$F$_5$ | |

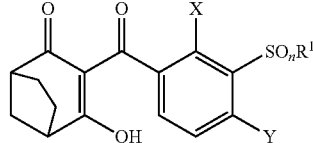

TABLE 5-continued

Compounds of the formula (I) according to the invention in which $R^2$ is hydroxyl, $R^4$, $R^5$, $R^6$ and $R^7$ are each hydrogen and $R^3$ and $R^8$ together are an ethylene group.

(I)

| No. | X | $R^1$ | n | Y | Physical data: $^1$H-NMR: δ [CDCl$_3$] |
|---|---|---|---|---|---|
| 5-131 | OEt | n-Pr | 2 | C$_2$F$_5$ | |
| 5-132 | OEt | i-Pr | 2 | C$_2$F$_5$ | |
| 5-133 | OCH$_2$—c-Pr | Me | 0 | C$_2$F$_5$ | |
| 5-134 | OCH$_2$—c-Pr | Et | 0 | C$_2$F$_5$ | |
| 5-135 | OCH$_2$—c-Pr | n-Pr | 0 | C$_2$F$_5$ | |
| 5-136 | OCH$_2$—c-Pr | i-Pr | 0 | C$_2$F$_5$ | |
| 5-137 | OCH$_2$—c-Pr | Me | 1 | C$_2$F$_5$ | |
| 5-138 | OCH$_2$—c-Pr | Et | 1 | C$_2$F$_5$ | |
| 5-139 | OCH$_2$—c-Pr | n-Pr | 1 | C$_2$F$_5$ | |
| 5-140 | OCH$_2$—c-Pr | i-Pr | 1 | C$_2$F$_5$ | |
| 5-141 | OCH$_2$—c-Pr | Me | 2 | C$_2$F$_5$ | |
| 5-142 | OCH$_2$—c-Pr | Et | 2 | C$_2$F$_5$ | |
| 5-143 | OCH$_2$—c-Pr | n-Pr | 2 | C$_2$F$_5$ | |
| 5-144 | OCH$_2$—c-Pr | i-Pr | 2 | C$_2$F$_5$ | |
| 5-145 | OCH$_2$CH$_2$OMe | Me | 0 | C$_2$F$_5$ | |
| 5-146 | OCH$_2$CH$_2$OMe | Et | 0 | C$_2$F$_5$ | |
| 5-147 | OCH$_2$CH$_2$OMe | n-Pr | 0 | C$_2$F$_5$ | |
| 5-148 | OCH$_2$CH$_2$OMe | i-Pr | 0 | C$_2$F$_5$ | |
| 5-149 | OCH$_2$CH$_2$OMe | Me | 1 | C$_2$F$_5$ | |
| 5-150 | OCH$_2$CH$_2$OMe | Et | 1 | C$_2$F$_5$ | |
| 5-151 | OCH$_2$CH$_2$OMe | n-Pr | 1 | C$_2$F$_5$ | |
| 5-152 | OCH$_2$CH$_2$OMe | i-Pr | 1 | C$_2$F$_5$ | |
| 5-153 | OCH$_2$CH$_2$OMe | Me | 2 | C$_2$F$_5$ | |
| 5-154 | OCH$_2$CH$_2$OMe | Et | 2 | C$_2$F$_5$ | |
| 5-155 | OCH$_2$CH$_2$OMe | n-Pr | 2 | C$_2$F$_5$ | |
| 5-156 | OCH$_2$CH$_2$OMe | i-Pr | 2 | C$_2$F$_5$ | |
| 5-157 | OCH$_2$CH$_2$SMe | Me | 0 | C$_2$F$_5$ | |
| 5-158 | OCH$_2$CH$_2$SMe | Et | 0 | C$_2$F$_5$ | |
| 5-159 | OCH$_2$CH$_2$SMe | n-Pr | 0 | C$_2$F$_5$ | |
| 5-160 | OCH$_2$CH$_2$SMe | i-Pr | 0 | C$_2$F$_5$ | |
| 5-161 | OCH$_2$CH$_2$SMe | Me | 1 | C$_2$F$_5$ | |
| 5-162 | OCH$_2$CH$_2$SMe | Et | 1 | C$_2$F$_5$ | |
| 5-163 | OCH$_2$CH$_2$SMe | n-Pr | 1 | C$_2$F$_5$ | |
| 5-164 | OCH$_2$CH$_2$SMe | i-Pr | 1 | C$_2$F$_5$ | |
| 5-165 | OCH$_2$CH$_2$SMe | Me | 2 | C$_2$F$_5$ | |
| 5-166 | OCH$_2$CH$_2$SMe | Et | 2 | C$_2$F$_5$ | |
| 5-167 | OCH$_2$CH$_2$SMe | n-Pr | 2 | C$_2$F$_5$ | |
| 5-168 | OCH$_2$CH$_2$SMe | i-Pr | 2 | C$_2$F$_5$ | |
| 5-169 | OCH$_2$CH$_2$SO$_2$Me | Me | 0 | C$_2$F$_5$ | |
| 5-170 | OCH$_2$CH$_2$SO$_2$Me | Et | 0 | C$_2$F$_5$ | |
| 5-171 | OCH$_2$CH$_2$SO$_2$Me | n-Pr | 0 | C$_2$F$_5$ | |
| 5-172 | OCH$_2$CH$_2$SO$_2$Me | i-Pr | 0 | C$_2$F$_5$ | |
| 5-173 | OCH$_2$CH$_2$SO$_2$Me | Me | 1 | C$_2$F$_5$ | |
| 5-174 | OCH$_2$CH$_2$SO$_2$Me | Et | 1 | C$_2$F$_5$ | |
| 5-175 | OCH$_2$CH$_2$SO$_2$Me | n-Pr | 1 | C$_2$F$_5$ | |
| 5-176 | OCH$_2$CH$_2$SO$_2$Me | i-Pr | 1 | C$_2$F$_5$ | |
| 5-177 | OCH$_2$CH$_2$SO$_2$Me | Me | 2 | C$_2$F$_5$ | |
| 5-178 | OCH$_2$CH$_2$SO$_2$Me | Et | 2 | C$_2$F$_5$ | |
| 5-179 | OCH$_2$CH$_2$SO$_2$Me | n-Pr | 2 | C$_2$F$_5$ | |
| 5-180 | OCH$_2$CH$_2$SO$_2$Me | i-Pr | 2 | C$_2$F$_5$ | |
| 5-181 | OMe | Me | 0 | CCl$_3$ | |
| 5-182 | OMe | Et | 0 | CCl$_3$ | |
| 5-183 | OMe | n-Pr | 0 | CCl$_3$ | |
| 5-184 | OMe | i-Pr | 0 | CCl$_3$ | |
| 5-185 | OMe | Me | 1 | CCl$_3$ | |
| 5-186 | OMe | Et | 1 | CCl$_3$ | |
| 5-187 | OMe | n-Pr | 1 | CCl$_3$ | |
| 5-188 | OMe | i-Pr | 1 | CCl$_3$ | |
| 5-189 | OMe | Me | 2 | CCl$_3$ | |
| 5-190 | OMe | Et | 2 | CCl$_3$ | |
| 5-191 | OMe | n-Pr | 2 | CCl$_3$ | |
| 5-192 | OMe | i-Pr | 2 | CCl$_3$ | |
| 5-193 | OEt | Me | 0 | CCl$_3$ | |
| 5-194 | OEt | Et | 0 | CCl$_3$ | |
| 5-195 | OEt | n-Pr | 0 | CCl$_3$ | |
| 5-196 | OEt | i-Pr | 0 | CCl$_3$ | |
| 5-197 | OEt | Me | 1 | CCl$_3$ | |
| 5-198 | OEt | Et | 1 | CCl$_3$ | |
| 5-199 | OEt | n-Pr | 1 | CCl$_3$ | |
| 5-200 | OEt | i-Pr | 1 | CCl$_3$ | |
| 5-201 | OEt | Me | 2 | CCl$_3$ | |
| 5-202 | OEt | Et | 2 | CCl$_3$ | |
| 5-203 | OEt | n-Pr | 2 | CCl$_3$ | |
| 5-204 | OEt | i-Pr | 2 | CCl$_3$ | |
| 5-205 | OCH$_2$—c-Pr | Me | 0 | CCl$_3$ | |
| 5-206 | OCH$_2$—c-Pr | Et | 0 | CCl$_3$ | |
| 5-207 | OCH$_2$—c-Pr | n-Pr | 0 | CCl$_3$ | |
| 5-208 | OCH$_2$—c-Pr | i-Pr | 0 | CCl$_3$ | |
| 5-209 | OCH$_2$—c-Pr | Me | 1 | CCl$_3$ | |
| 5-210 | OCH$_2$—c-Pr | Et | 1 | CCl$_3$ | |
| 5-211 | OCH$_2$—c-Pr | n-Pr | 1 | CCl$_3$ | |
| 5-212 | OCH$_2$—c-Pr | i-Pr | 1 | CCl$_3$ | |
| 5-213 | OCH$_2$—c-Pr | Me | 2 | CCl$_3$ | |
| 5-214 | OCH$_2$—c-Pr | Et | 2 | CCl$_3$ | |
| 5-215 | OCH$_2$—c-Pr | n-Pr | 2 | CCl$_3$ | |
| 5-216 | OCH$_2$—c-Pr | i-Pr | 2 | CCl$_3$ | |
| 5-217 | OCH$_2$CH$_2$OMe | Me | 0 | CCl$_3$ | |
| 5-218 | OCH$_2$CH$_2$OMe | Et | 0 | CCl$_3$ | |
| 5-219 | OCH$_2$CH$_2$OMe | n-Pr | 0 | CCl$_3$ | |
| 5-220 | OCH$_2$CH$_2$OMe | i-Pr | 0 | CCl$_3$ | |
| 5-221 | OCH$_2$CH$_2$OMe | Me | 1 | CCl$_3$ | |
| 5-222 | OCH$_2$CH$_2$OMe | Et | 1 | CCl$_3$ | |
| 5-223 | OCH$_2$CH$_2$OMe | n-Pr | 1 | CCl$_3$ | |
| 5-224 | OCH$_2$CH$_2$OMe | i-Pr | 1 | CCl$_3$ | |
| 5-225 | OCH$_2$CH$_2$OMe | Me | 2 | CCl$_3$ | |
| 5-226 | OCH$_2$CH$_2$OMe | Et | 2 | CCl$_3$ | |
| 5-227 | OCH$_2$CH$_2$OMe | n-Pr | 2 | CCl$_3$ | |
| 5-228 | OCH$_2$CH$_2$OMe | i-Pr | 2 | CCl$_3$ | |
| 5-229 | OCH$_2$CH$_2$SMe | Me | 0 | CCl$_3$ | |
| 5-230 | OCH$_2$CH$_2$SMe | Et | 0 | CCl$_3$ | |
| 5-231 | OCH$_2$CH$_2$SMe | n-Pr | 0 | CCl$_3$ | |
| 5-232 | OCH$_2$CH$_2$SMe | i-Pr | 0 | CCl$_3$ | |
| 5-233 | OCH$_2$CH$_2$SMe | Me | 1 | CCl$_3$ | |
| 5-234 | OCH$_2$CH$_2$SMe | Et | 1 | CCl$_3$ | |
| 5-235 | OCH$_2$CH$_2$SMe | n-Pr | 1 | CCl$_3$ | |
| 5-236 | OCH$_2$CH$_2$SMe | i-Pr | 1 | CCl$_3$ | |
| 5-237 | OCH$_2$CH$_2$SMe | Me | 2 | CCl$_3$ | |
| 5-238 | OCH$_2$CH$_2$SMe | Et | 2 | CCl$_3$ | |
| 5-239 | OCH$_2$CH$_2$SMe | n-Pr | 2 | CCl$_3$ | |
| 5-240 | OCH$_2$CH$_2$SMe | i-Pr | 2 | CCl$_3$ | |
| 5-241 | OCH$_2$CH$_2$SO$_2$Me | Me | 0 | CCl$_3$ | |
| 5-242 | OCH$_2$CH$_2$SO$_2$Me | Et | 0 | CCl$_3$ | |
| 5-243 | OCH$_2$CH$_2$SO$_2$Me | n-Pr | 0 | CCl$_3$ | |
| 5-244 | OCH$_2$CH$_2$SO$_2$Me | i-Pr | 0 | CCl$_3$ | |
| 5-245 | OCH$_2$CH$_2$SO$_2$Me | Me | 1 | CCl$_3$ | |
| 5-246 | OCH$_2$CH$_2$SO$_2$Me | Et | 1 | CCl$_3$ | |
| 5-247 | OCH$_2$CH$_2$SO$_2$Me | n-Pr | 1 | CCl$_3$ | |
| 5-248 | OCH$_2$CH$_2$SO$_2$Me | i-Pr | 1 | CCl$_3$ | |
| 5-249 | OCH$_2$CH$_2$SO$_2$Me | Me | 2 | CCl$_3$ | |
| 5-250 | OCH$_2$CH$_2$SO$_2$Me | Et | 2 | CCl$_3$ | |
| 5-251 | OCH$_2$CH$_2$SO$_2$Me | n-Pr | 2 | CCl$_3$ | |
| 5-252 | OCH$_2$CH$_2$SO$_2$Me | i-Pr | 2 | CCl$_3$ | |
| 5-253 | OMe | Me | 0 | CHF2 | |
| 5-254 | OMe | Et | 0 | CHF2 | |
| 5-255 | OMe | n-Pr | 0 | CHF2 | |
| 5-256 | OMe | i-Pr | 0 | CHF2 | |
| 5-257 | OMe | Me | 1 | CHF2 | |
| 5-258 | OMe | Et | 1 | CHF2 | |

TABLE 5-continued

Compounds of the formula (I) according to the invention in which $R^2$ is hydroxyl, $R^4$, $R^5$, $R^6$ and $R^7$ are each hydrogen and $R^3$ and $R^8$ together are an ethylene group.

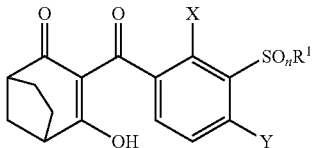

(I)

| No. | X | $R^1$ | n | Y | Physical data: $^1$H-NMR: δ [CDCl$_3$] |
|---|---|---|---|---|---|
| 5-259 | OMe | n-Pr | 1 | CHF2 | |
| 5-260 | OMe | i-Pr | 1 | CHF2 | |
| 5-261 | OMe | Me | 2 | CHF2 | |
| 5-262 | OMe | Et | 2 | CHF2 | |
| 5-263 | OMe | n-Pr | 2 | CHF2 | |
| 5-264 | OMe | i-Pr | 2 | CHF2 | |
| 5-265 | OEt | Me | 0 | CHF2 | |
| 5-266 | OEt | Et | 0 | CHF2 | |
| 5-267 | OEt | n-Pr | 0 | CHF2 | |
| 5-268 | OEt | i-Pr | 0 | CHF2 | |
| 5-269 | OEt | Me | 1 | CHF2 | |
| 5-270 | OEt | Et | 1 | CHF2 | |
| 5-271 | OEt | n-Pr | 1 | CHF2 | |
| 5-272 | OEt | i-Pr | 1 | CHF2 | |
| 5-273 | OEt | Me | 2 | CHF2 | |
| 5-274 | OEt | Et | 2 | CHF2 | |
| 5-275 | OEt | n-Pr | 2 | CHF2 | |
| 5-276 | OEt | i-Pr | 2 | CHF2 | |
| 5-277 | O—CH$_2$—c-Pr | Me | 0 | CHF2 | |
| 5-278 | O—CH$_2$—c-Pr | Et | 0 | CHF2 | |
| 5-279 | O—CH$_2$—c-Pr | n-Pr | 0 | CHF2 | |
| 5-280 | O—CH$_2$—c-Pr | i-Pr | 0 | CHF2 | |
| 5-281 | O—CH$_2$—c-Pr | Me | 1 | CHF2 | |
| 5-282 | O—CH$_2$—c-Pr | Et | 1 | CHF2 | |
| 5-283 | O—CH$_2$—c-Pr | n-Pr | 1 | CHF2 | |
| 5-284 | O—CH$_2$—c-Pr | i-Pr | 1 | CHF2 | |
| 5-285 | O—CH$_2$—c-Pr | Me | 2 | CHF2 | |
| 5-286 | O—CH$_2$—c-Pr | Et | 2 | CHF2 | |
| 5-287 | O—CH$_2$—c-Pr | n-Pr | 2 | CHF2 | |
| 5-288 | O—CH$_2$—c-Pr | i-Pr | 2 | CHF2 | |
| 5-289 | OCH$_2$CH$_2$OMe | Me | 0 | CHF2 | |
| 5-290 | OCH$_2$CH$_2$OMe | Et | 0 | CHF2 | |
| 5-291 | OCH$_2$CH$_2$OMe | n-Pr | 0 | CHF2 | |
| 5-292 | OCH$_2$CH$_2$OMe | i-Pr | 0 | CHF2 | |
| 5-293 | OCH$_2$CH$_2$OMe | Me | 1 | CHF2 | |
| 5-294 | OCH$_2$CH$_2$OMe | Et | 1 | CHF2 | |
| 5-295 | OCH$_2$CH$_2$OMe | n-Pr | 1 | CHF2 | |
| 5-296 | OCH$_2$CH$_2$OMe | i-Pr | 1 | CHF2 | |
| 5-297 | OCH$_2$CH$_2$OMe | Me | 2 | CHF2 | |
| 5-298 | OCH$_2$CH$_2$OMe | Et | 2 | CHF2 | |
| 5-299 | OCH$_2$CH$_2$OMe | n-Pr | 2 | CHF2 | |
| 5-300 | OCH$_2$CH$_2$OMe | i-Pr | 2 | CHF2 | |
| 5-301 | OCH$_2$CH$_2$SMe | Me | 0 | CHF2 | |
| 5-302 | OCH$_2$CH$_2$SMe | Et | 0 | CHF2 | |
| 5-303 | OCH$_2$CH$_2$SMe | n-Pr | 0 | CHF2 | |
| 5-304 | OCH$_2$CH$_2$SMe | i-Pr | 0 | CHF2 | |
| 5-305 | OCH$_2$CH$_2$SMe | Me | 1 | CHF2 | |
| 5-306 | OCH$_2$CH$_2$SMe | Et | 1 | CHF2 | |
| 5-307 | OCH$_2$CH$_2$SMe | n-Pr | 1 | CHF2 | |
| 5-308 | OCH$_2$CH$_2$SMe | i-Pr | 1 | CHF2 | |
| 5-309 | OCH$_2$CH$_2$SMe | Me | 2 | CHF2 | |
| 5-310 | OCH$_2$CH$_2$SMe | Et | 2 | CHF2 | |
| 5-311 | OCH$_2$CH$_2$SMe | n-Pr | 2 | CHF2 | |
| 5-312 | OCH$_2$CH$_2$SMe | i-Pr | 2 | CHF2 | |
| 5-313 | OCH$_2$CH$_2$SO$_2$Me | Me | 0 | CHF2 | |
| 5-314 | OCH$_2$CH$_2$SO$_2$Me | Et | 0 | CHF2 | |
| 5-315 | OCH$_2$CH$_2$SO$_2$Me | n-Pr | 0 | CHF2 | |
| 5-316 | OCH$_2$CH$_2$SO$_2$Me | i-Pr | 0 | CHF2 | |
| 5-317 | OCH$_2$CH$_2$SO$_2$Me | Me | 1 | CHF2 | |
| 5-318 | OCH$_2$CH$_2$SO$_2$Me | Et | 1 | CHF2 | |
| 5-319 | OCH$_2$CH$_2$SO$_2$Me | n-Pr | 1 | CHF2 | |
| 5-320 | OCH$_2$CH$_2$SO$_2$Me | i-Pr | 1 | CHF2 | |
| 5-321 | OCH$_2$CH$_2$SO$_2$Me | Me | 2 | CHF2 | |
| 5-322 | OCH$_2$CH$_2$SO$_2$Me | Et | 2 | CHF2 | |

TABLE 5-continued

Compounds of the formula (I) according to the invention in which $R^2$ is hydroxyl, $R^4$, $R^5$, $R^6$ and $R^7$ are each hydrogen and $R^3$ and $R^8$ together are an ethylene group.

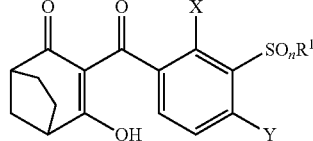

(I)

| No. | X | $R^1$ | n | Y | Physical data: $^1$H-NMR: δ [CDCl$_3$] |
|---|---|---|---|---|---|
| 5-323 | OCH$_2$CH$_2$SO$_2$Me | n-Pr | 2 | CHF2 | |
| 5-324 | OCH$_2$CH$_2$SO$_2$Me | i-Pr | 2 | CHF2 | |
| 5-325 | OMe | Me | 0 | CF(CF$_3$)$_2$ | |
| 5-326 | OMe | Et | 0 | CF(CF$_3$)$_2$ | |
| 5-327 | OMe | n-Pr | 0 | CF(CF$_3$)$_2$ | |
| 5-328 | OMe | i-Pr | 0 | CF(CF$_3$)$_2$ | |
| 5-329 | OMe | Me | 1 | CF(CF$_3$)$_2$ | |
| 5-330 | OMe | Et | 1 | CF(CF$_3$)$_2$ | |
| 5-331 | OMe | n-Pr | 1 | CF(CF$_3$)$_2$ | |
| 5-332 | OMe | i-Pr | 1 | CF(CF$_3$)$_2$ | |
| 5-333 | OMe | Me | 2 | CF(CF$_3$)$_2$ | |
| 5-334 | OMe | Et | 2 | CF(CF$_3$)$_2$ | |
| 5-335 | OMe | n-Pr | 2 | CF(CF$_3$)$_2$ | |
| 5-336 | OMe | i-Pr | 2 | CF(CF$_3$)$_2$ | |
| 5-337 | OEt | Me | 0 | CF(CF$_3$)$_2$ | |
| 5-338 | OEt | Et | 0 | CF(CF$_3$)$_2$ | |
| 5-339 | OEt | n-Pr | 0 | CF(CF$_3$)$_2$ | |
| 5-340 | OEt | i-Pr | 0 | CF(CF$_3$)$_2$ | |
| 5-341 | OEt | Me | 1 | CF(CF$_3$)$_2$ | |
| 5-342 | OEt | Et | 1 | CF(CF$_3$)$_2$ | |
| 5-343 | OEt | n-Pr | 1 | CF(CF$_3$)$_2$ | |
| 5-344 | OEt | i-Pr | 1 | CF(CF$_3$)$_2$ | |
| 5-345 | OEt | Me | 2 | CF(CF$_3$)$_2$ | |
| 5-346 | OEt | Et | 2 | CF(CF$_3$)$_2$ | |
| 5-347 | OEt | n-Pr | 2 | CF(CF$_3$)$_2$ | |
| 5-348 | OEt | i-Pr | 2 | CF(CF$_3$)$_2$ | |
| 5-349 | O—CH$_2$—c-Pr | Me | 0 | CF(CF$_3$)$_2$ | |
| 5-350 | O—CH$_2$—c-Pr | Et | 0 | CF(CF$_3$)$_2$ | |
| 5-351 | O—CH$_2$—c-Pr | n-Pr | 0 | CF(CF$_3$)$_2$ | |
| 5-352 | O—CH$_2$—c-Pr | i-Pr | 0 | CF(CF$_3$)$_2$ | |
| 5-353 | O—CH$_2$—c-Pr | Me | 1 | CF(CF$_3$)$_2$ | |
| 5-354 | O—CH$_2$—c-Pr | Et | 1 | CF(CF$_3$)$_2$ | |
| 5-355 | O—CH$_2$—c-Pr | n-Pr | 1 | CF(CF$_3$)$_2$ | |
| 5-356 | O—CH$_2$—c-Pr | i-Pr | 1 | CF(CF$_3$)$_2$ | |
| 5-357 | O—CH$_2$—c-Pr | Me | 2 | CF(CF$_3$)$_2$ | |
| 5-358 | O—CH$_2$—c-Pr | Et | 2 | CF(CF$_3$)$_2$ | |
| 5-359 | O—CH$_2$—c-Pr | n-Pr | 2 | CF(CF$_3$)$_2$ | |
| 5-360 | O—CH$_2$—c-Pr | i-Pr | 2 | CF(CF$_3$)$_2$ | |
| 5-361 | OCH$_2$CH$_2$OMe | Me | 0 | CF(CF$_3$)$_2$ | |
| 5-362 | OCH$_2$CH$_2$OMe | Et | 0 | CF(CF$_3$)$_2$ | |
| 5-363 | OCH$_2$CH$_2$OMe | n-Pr | 0 | CF(CF$_3$)$_2$ | |
| 5-364 | OCH$_2$CH$_2$OMe | i-Pr | 0 | CF(CF$_3$)$_2$ | |
| 5-365 | OCH$_2$CH$_2$OMe | Me | 1 | CF(CF$_3$)$_2$ | |
| 5-366 | OCH$_2$CH$_2$OMe | Et | 1 | CF(CF$_3$)$_2$ | |
| 5-367 | OCH$_2$CH$_2$OMe | n-Pr | 1 | CF(CF$_3$)$_2$ | |
| 5-368 | OCH$_2$CH$_2$OMe | i-Pr | 1 | CF(CF$_3$)$_2$ | |
| 5-369 | OCH$_2$CH$_2$OMe | Me | 2 | CF(CF$_3$)$_2$ | |
| 5-370 | OCH$_2$CH$_2$OMe | Et | 2 | CF(CF$_3$)$_2$ | |
| 5-371 | OCH$_2$CH$_2$OMe | n-Pr | 2 | CF(CF$_3$)$_2$ | |
| 5-372 | OCH$_2$CH$_2$OMe | i-Pr | 2 | CF(CF$_3$)$_2$ | |
| 5-373 | OCH$_2$CH$_2$SMe | Me | 0 | CF(CF$_3$)$_2$ | |
| 5-374 | OCH$_2$CH$_2$SMe | Et | 0 | CF(CF$_3$)$_2$ | |
| 5-375 | OCH$_2$CH$_2$SMe | n-Pr | 0 | CF(CF$_3$)$_2$ | |
| 5-376 | OCH$_2$CH$_2$SMe | i-Pr | 0 | CF(CF$_3$)$_2$ | |
| 5-377 | OCH$_2$CH$_2$SMe | Me | 1 | CF(CF$_3$)$_2$ | |
| 5-378 | OCH$_2$CH$_2$SMe | Et | 1 | CF(CF$_3$)$_2$ | |
| 5-379 | OCH$_2$CH$_2$SMe | n-Pr | 1 | CF(CF$_3$)$_2$ | |
| 5-380 | OCH$_2$CH$_2$SMe | i-Pr | 1 | CF(CF$_3$)$_2$ | |
| 5-381 | OCH$_2$CH$_2$SMe | Me | 2 | CF(CF$_3$)$_2$ | |
| 5-382 | OCH$_2$CH$_2$SMe | Et | 2 | CF(CF$_3$)$_2$ | |
| 5-383 | OCH$_2$CH$_2$SMe | n-Pr | 2 | CF(CF$_3$)$_2$ | |
| 5-384 | OCH$_2$CH$_2$SMe | i-Pr | 2 | CF(CF$_3$)$_2$ | |
| 5-385 | OCH$_2$CH$_2$SO$_2$Me | Me | 0 | CF(CF$_3$)$_2$ | |
| 5-386 | OCH$_2$CH$_2$SO$_2$Me | Et | 0 | CF(CF$_3$)$_2$ | |

TABLE 5-continued

Compounds of the formula (I) according to the invention in which R² is hydroxyl, R⁴, R⁵, R⁶ and R⁷ are each hydrogen and R³ and R⁸ together are an ethylene group.

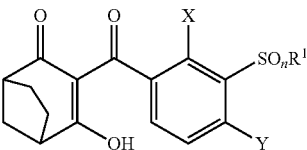

(I)

| No. | X | R¹ | n | Y | Physical data: ¹H-NMR: δ [CDCl₃] |
|---|---|---|---|---|---|
| 5-387 | OCH₂CH₂SO₂Me | n-Pr | 0 | CF(CF₃)₂ | |
| 5-388 | OCH₂CH₂SO₂Me | i-Pr | 0 | CF(CF₃)₂ | |
| 5-389 | OCH₂CH₂SO₂Me | Me | 1 | CF(CF₃)₂ | |
| 5-390 | OCH₂CH₂SO₂Me | Et | 1 | CF(CF₃)₂ | |
| 5-391 | OCH₂CH₂SO₂Me | n-Pr | 1 | CF(CF₃)₂ | |
| 5-392 | OCH₂CH₂SO₂Me | i-Pr | 1 | CF(CF₃)₂ | |
| 5-393 | OCH₂CH₂SO₂Me | Me | 2 | CF(CF₃)₂ | |
| 5-394 | OCH₂CH₂SO₂Me | Et | 2 | CF(CF₃)₂ | |
| 5-395 | OCH₂CH₂SO₂Me | n-Pr | 2 | CF(CF₃)₂ | |
| 5-396 | OCH₂CH₂SO₂Me | i-Pr | 2 | CF(CF₃)₂ | |

TABLE 6

Compounds of the formula (I) according to the invention in which R² is phenylthio and R³ to R⁸ are each hydrogen.

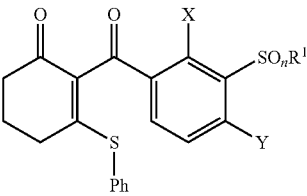

(I)

| No. | X | R¹ | n | Y | Physical data: ¹H-NMR: δ [CDCl₃] |
|---|---|---|---|---|---|
| 6-1 | OMe | Me | 0 | CF₃ | |
| 6-2 | OMe | Et | 0 | CF₃ | |
| 6-3 | OMe | n-Pr | 0 | CF₃ | |
| 6-4 | OMe | i-Pr | 0 | CF₃ | |
| 6-5 | OMe | Me | 1 | CF₃ | |
| 6-6 | OMe | Et | 1 | CF₃ | |
| 6-7 | OMe | n-Pr | 1 | CF₃ | |
| 6-8 | OMe | i-Pr | 1 | CF₃ | |
| 6-9 | OMe | Me | 2 | CF₃ | |
| 6-10 | OMe | Et | 2 | CF₃ | |
| 6-11 | OMe | n-Pr | 2 | CF₃ | |
| 6-12 | OMe | i-Pr | 2 | CF₃ | |
| 6-13 | OEt | Me | 0 | CF₃ | |
| 6-14 | OEt | Et | 0 | CF₃ | |
| 6-15 | OEt | n-Pr | 0 | CF₃ | |
| 6-16 | OEt | i-Pr | 0 | CF₃ | |
| 6-17 | OEt | Me | 1 | CF₃ | |
| 6-18 | OEt | Et | 1 | CF₃ | |
| 6-19 | OEt | n-Pr | 1 | CF₃ | |
| 6-20 | OEt | i-Pr | 1 | CF₃ | |
| 6-21 | OEt | Me | 2 | CF₃ | |
| 6-22 | OEt | Et | 2 | CF₃ | |
| 6-23 | OEt | n-Pr | 2 | CF₃ | |
| 6-24 | OEt | i-Pr | 2 | CF₃ | |
| 6-25 | OCH₂CH₂OMe | Me | 0 | CF₃ | |
| 6-26 | OCH₂CH₂OMe | Et | 0 | CF₃ | |
| 6-27 | OCH₂CH₂OMe | n-Pr | 0 | CF₃ | |
| 6-28 | OCH₂CH₂OMe | i-Pr | 0 | CF₃ | |
| 6-29 | OCH₂CH₂OMe | Me | 1 | CF₃ | |
| 6-30 | OCH₂CH₂OMe | Et | 1 | CF₃ | |
| 6-31 | OCH₂CH₂OMe | n-Pr | 1 | CF₃ | |

TABLE 6-continued

Compounds of the formula (I) according to the invention in which R² is phenylthio and R³ to R⁸ are each hydrogen.

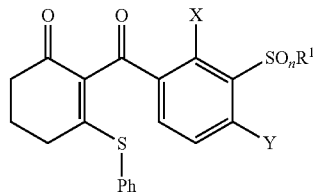

(I)

| No. | X | R¹ | n | Y | Physical data: ¹H-NMR: δ [CDCl₃] |
|---|---|---|---|---|---|
| 6-32 | OCH₂CH₂OMe | i-Pr | 1 | CF₃ | |
| 6-33 | OCH₂CH₂OMe | Me | 2 | CF₃ | |
| 6-34 | OCH₂CH₂OMe | Et | 2 | CF₃ | |
| 6-35 | OCH₂CH₂OMe | n-Pr | 2 | CF₃ | |
| 6-36 | OCH₂CH₂OMe | i-Pr | 2 | CF₃ | |

TABLE 7

Compounds of the formula (I) according to the invention in which R² is phenylthio, R³ and R⁴ are each methyl and R⁵ to R⁸ are each hydrogen.

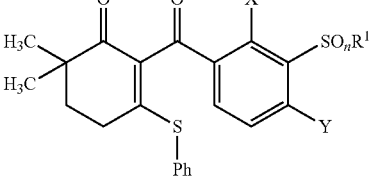

(I)

| No. | X | R¹ | n | Y | Physical data: ¹H-NMR: δ [CDCl₃] |
|---|---|---|---|---|---|
| 7-1 | OMe | Me | 0 | CF₃ | |
| 7-2 | OMe | Et | 0 | CF₃ | |
| 7-3 | OMe | n-Pr | 0 | CF₃ | |
| 7-4 | OMe | i-Pr | 0 | CF₃ | |
| 7-5 | OMe | Me | 1 | CF₃ | |
| 7-6 | OMe | Et | 1 | CF₃ | |
| 7-7 | OMe | n-Pr | 1 | CF₃ | |
| 7-8 | OMe | i-Pr | 1 | CF₃ | |
| 7-9 | OMe | Me | 2 | CF₃ | |
| 7-10 | OMe | Et | 2 | CF₃ | |
| 7-11 | OMe | n-Pr | 2 | CF₃ | |
| 7-12 | OMe | i-Pr | 2 | CF₃ | |
| 7-13 | OEt | Me | 0 | CF₃ | |
| 7-14 | OEt | Et | 0 | CF₃ | |
| 7-15 | OEt | n-Pr | 0 | CF₃ | |
| 7-16 | OEt | i-Pr | 0 | CF₃ | |
| 7-17 | OEt | Me | 1 | CF₃ | |
| 7-18 | OEt | Et | 1 | CF₃ | |
| 7-19 | OEt | n-Pr | 1 | CF₃ | |
| 7-20 | OEt | i-Pr | 1 | CF₃ | |
| 7-21 | OEt | Me | 2 | CF₃ | |
| 7-22 | OEt | Et | 2 | CF₃ | |
| 7-23 | OEt | n-Pr | 2 | CF₃ | |
| 7-24 | OEt | i-Pr | 2 | CF₃ | |
| 7-25 | OCH₂CH₂OMe | Me | 0 | CF₃ | |
| 7-26 | OCH₂CH₂OMe | Et | 0 | CF₃ | |
| 7-27 | OCH₂CH₂OMe | n-Pr | 0 | CF₃ | |
| 7-28 | OCH₂CH₂OMe | i-Pr | 0 | CF₃ | |
| 7-29 | OCH₂CH₂OMe | Me | 1 | CF₃ | |
| 7-30 | OCH₂CH₂OMe | Et | 1 | CF₃ | |
| 7-31 | OCH₂CH₂OMe | n-Pr | 1 | CF₃ | |
| 7-32 | OCH₂CH₂OMe | i-Pr | 1 | CF₃ | |
| 7-33 | OCH₂CH₂OMe | Me | 2 | CF₃ | |
| 7-34 | OCH₂CH₂OMe | Et | 2 | CF₃ | |
| 7-35 | OCH₂CH₂OMe | n-Pr | 2 | CF₃ | |
| 7-36 | OCH₂CH₂OMe | i-Pr | 2 | CF₃ | |

TABLE 8

Compounds of the formula (I) according to the invention in which $R^2$ is phenylthio, $R^3$, $R^4$, $R^7$ and $R^8$ are each hydrogen and $R^5$ and $R^6$ are each methyl.

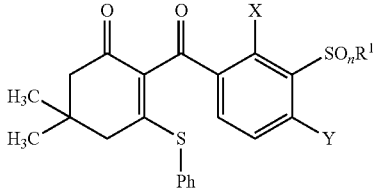

(I)

| No. | X | $R^1$ | n | Y | Physical data: $^1$H-NMR: δ [CDCl$_3$] |
|---|---|---|---|---|---|
| 8-1 | OMe | Me | 0 | CF$_3$ | |
| 8-2 | OMe | Et | 0 | CF$_3$ | |
| 8-3 | OMe | n-Pr | 0 | CF$_3$ | |
| 8-4 | OMe | i-Pr | 0 | CF$_3$ | |
| 8-5 | OMe | Me | 1 | CF$_3$ | |
| 8-6 | OMe | Et | 1 | CF$_3$ | |
| 8-7 | OMe | n-Pr | 1 | CF$_3$ | |
| 8-8 | OMe | i-Pr | 1 | CF$_3$ | |
| 8-9 | OMe | Me | 2 | CF$_3$ | |
| 8-10 | OMe | Et | 2 | CF$_3$ | |
| 8-11 | OMe | n-Pr | 2 | CF$_3$ | |
| 8-12 | OMe | i-Pr | 2 | CF$_3$ | |
| 8-13 | OEt | Me | 0 | CF$_3$ | |
| 8-14 | OEt | Et | 0 | CF$_3$ | |
| 8-15 | OEt | n-Pr | 0 | CF$_3$ | |
| 8-16 | OEt | i-Pr | 0 | CF$_3$ | |
| 8-17 | OEt | Me | 1 | CF$_3$ | |
| 8-18 | OEt | Et | 1 | CF$_3$ | |
| 8-19 | OEt | n-Pr | 1 | CF$_3$ | |
| 8-20 | OEt | i-Pr | 1 | CF$_3$ | |
| 8-21 | OEt | Me | 2 | CF$_3$ | |
| 8-22 | OEt | Et | 2 | CF$_3$ | |
| 8-23 | OEt | n-Pr | 2 | CF$_3$ | |
| 8-24 | OEt | i-Pr | 2 | CF$_3$ | |
| 8-25 | OCH$_2$CH$_2$OMe | Me | 0 | CF$_3$ | |
| 8-26 | OCH$_2$CH$_2$OMe | Et | 0 | CF$_3$ | |
| 8-27 | OCH$_2$CH$_2$OMe | n-Pr | 0 | CF$_3$ | |
| 8-28 | OCH$_2$CH$_2$OMe | i-Pr | 0 | CF$_3$ | |
| 8-29 | OCH$_2$CH$_2$OMe | Me | 1 | CF$_3$ | |
| 8-30 | OCH$_2$CH$_2$OMe | Et | 1 | CF$_3$ | |
| 8-31 | OCH$_2$CH$_2$OMe | n-Pr | 1 | CF$_3$ | |
| 8-32 | OCH$_2$CH$_2$OMe | i-Pr | 1 | CF$_3$ | |
| 8-33 | OCH$_2$CH$_2$OMe | Me | 2 | CF$_3$ | |
| 8-34 | OCH$_2$CH$_2$OMe | Et | 2 | CF$_3$ | |
| 8-35 | OCH$_2$CH$_2$OMe | n-Pr | 2 | CF$_3$ | |
| 8-36 | OCH$_2$CH$_2$OMe | i-Pr | 2 | CF$_3$ | |

TABLE 9

Compounds of the formula (I) according to the invention in which $R^2$ is phenylthio, $R^3$ to $R^6$ are each hydrogen and $R^7$ and $R^8$ are each methyl.

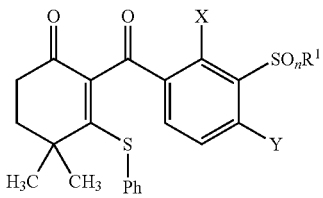

(I)

| No. | X | $R^1$ | n | Y | Physical data: $^1$H-NMR: δ [CDCl$_3$] |
|---|---|---|---|---|---|
| 9-1 | OMe | Me | 0 | CF$_3$ | |
| 9-2 | OMe | Et | 0 | CF$_3$ | |
| 9-3 | OMe | n-Pr | 0 | CF$_3$ | |

TABLE 9-continued

Compounds of the formula (I) according to the invention in which $R^2$ is phenylthio, $R^3$ to $R^6$ are each hydrogen and $R^7$ and $R^8$ are each methyl.

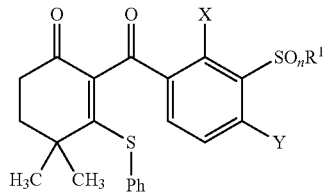

(I)

| No. | X | $R^1$ | n | Y | Physical data: $^1$H-NMR: δ [CDCl$_3$] |
|---|---|---|---|---|---|
| 9-4 | OMe | i-Pr | 0 | CF$_3$ | |
| 9-5 | OMe | Me | 1 | CF$_3$ | |
| 9-6 | OMe | Et | 1 | CF$_3$ | |
| 9-7 | OMe | n-Pr | 1 | CF$_3$ | |
| 9-8 | OMe | i-Pr | 1 | CF$_3$ | |
| 9-9 | OMe | Me | 2 | CF$_3$ | |
| 9-10 | OMe | Et | 2 | CF$_3$ | |
| 9-11 | OMe | n-Pr | 2 | CF$_3$ | |
| 9-12 | OMe | i-Pr | 2 | CF$_3$ | |
| 9-13 | OEt | Me | 0 | CF$_3$ | |
| 9-14 | OEt | Et | 0 | CF$_3$ | |
| 9-15 | OEt | n-Pr | 0 | CF$_3$ | |
| 9-16 | OEt | i-Pr | 0 | CF$_3$ | |
| 9-17 | OEt | Me | 1 | CF$_3$ | |
| 9-18 | OEt | Et | 1 | CF$_3$ | |
| 9-19 | OEt | n-Pr | 1 | CF$_3$ | |
| 9-20 | OEt | i-Pr | 1 | CF$_3$ | |
| 9-21 | OEt | Me | 2 | CF$_3$ | |
| 9-22 | OEt | Et | 2 | CF$_3$ | |
| 9-23 | OEt | n-Pr | 2 | CF$_3$ | |
| 9-24 | OEt | i-Pr | 2 | CF$_3$ | |
| 9-25 | OCH$_2$CH$_2$OMe | Me | 0 | CF$_3$ | |
| 9-26 | OCH$_2$CH$_2$OMe | Et | 0 | CF$_3$ | |
| 9-27 | OCH$_2$CH$_2$OMe | n-Pr | 0 | CF$_3$ | |
| 9-28 | OCH$_2$CH$_2$OMe | i-Pr | 0 | CF$_3$ | |
| 9-29 | OCH$_2$CH$_2$OMe | Me | 1 | CF$_3$ | |
| 9-30 | OCH$_2$CH$_2$OMe | Et | 1 | CF$_3$ | |
| 9-31 | OCH$_2$CH$_2$OMe | n-Pr | 1 | CF$_3$ | |
| 9-32 | OCH$_2$CH$_2$OMe | i-Pr | 1 | CF$_3$ | |
| 9-33 | OCH$_2$CH$_2$OMe | Me | 2 | CF$_3$ | |
| 9-34 | OCH$_2$CH$_2$OMe | Et | 2 | CF$_3$ | |
| 9-35 | OCH$_2$CH$_2$OMe | n-Pr | 2 | CF$_3$ | |
| 9-36 | OCH$_2$CH$_2$OMe | i-Pr | 2 | CF$_3$ | |

TABLE 10

Compounds of the formula (I) according to the invention in which $R^2$ is phenylthio, $R^3$, $R^4$, $R^5$, $R^7$ and $R^8$ are each hydrogen and $R^6$ is methyl.

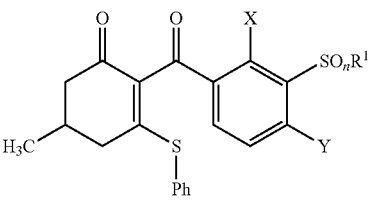

(I)

| No. | X | $R^1$ | n | Y | Physical data: $^1$H-NMR: δ [CDCl$_3$] |
|---|---|---|---|---|---|
| 10-1 | OMe | Me | 0 | CF$_3$ | |
| 10-2 | OMe | Et | 0 | CF$_3$ | |
| 10-3 | OMe | n-Pr | 0 | CF$_3$ | |
| 10-4 | OMe | i-Pr | 0 | CF$_3$ | |
| 10-5 | OMe | Me | 1 | CF$_3$ | |
| 10-6 | OMe | Et | 1 | CF$_3$ | |
| 10-7 | OMe | n-Pr | 1 | CF$_3$ | |

TABLE 10-continued

Compounds of the formula (I) according to the invention in which $R^2$ is phenylthio, $R^3$, $R^4$, $R^5$, $R^7$ and $R^8$ are each hydrogen and $R^6$ is methyl.

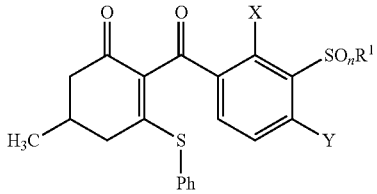

(I)

| No. | X | $R^1$ | n | Y | Physical data: $^1$H-NMR: δ [CDCl$_3$] |
|---|---|---|---|---|---|
| 10-8 | OMe | i-Pr | 1 | CF$_3$ | |
| 10-9 | OMe | Me | 2 | CF$_3$ | |
| 10-10 | OMe | Et | 2 | CF$_3$ | |
| 10-11 | OMe | n-Pr | 2 | CF$_3$ | |
| 10-12 | OMe | i-Pr | 2 | CF$_3$ | |
| 10-13 | OEt | Me | 0 | CF$_3$ | |
| 10-14 | OEt | Et | 0 | CF$_3$ | |
| 10-15 | OEt | n-Pr | 0 | CF$_3$ | |
| 10-16 | OEt | i-Pr | 0 | CF$_3$ | |
| 10-17 | OEt | Me | 1 | CF$_3$ | |
| 10-18 | OEt | Et | 1 | CF$_3$ | |
| 10-19 | OEt | n-Pr | 1 | CF$_3$ | |
| 10-20 | OEt | i-Pr | 1 | CF$_3$ | |
| 10-21 | OEt | Me | 2 | CF$_3$ | |
| 10-22 | OEt | Et | 2 | CF$_3$ | |
| 10-23 | OEt | n-Pr | 2 | CF$_3$ | |
| 10-24 | OEt | i-Pr | 2 | CF$_3$ | |
| 10-25 | OCH$_2$CH$_2$OMe | Me | 0 | CF$_3$ | |
| 10-26 | OCH$_2$CH$_2$OMe | Et | 0 | CF$_3$ | |
| 10-27 | OCH$_2$CH$_2$OMe | n-Pr | 0 | CF$_3$ | |
| 10-28 | OCH$_2$CH$_2$OMe | i-Pr | 0 | CF$_3$ | |
| 10-29 | OCH$_2$CH$_2$OMe | Me | 1 | CF$_3$ | |
| 10-30 | OCH$_2$CH$_2$OMe | Et | 1 | CF$_3$ | |
| 10-31 | OCH$_2$CH$_2$OMe | n-Pr | 1 | CF$_3$ | |
| 10-32 | OCH$_2$CH$_2$OMe | i-Pr | 1 | CF$_3$ | |
| 10-33 | OCH$_2$CH$_2$OMe | Me | 2 | CF$_3$ | |
| 10-34 | OCH$_2$CH$_2$OMe | Et | 2 | CF$_3$ | |
| 10-35 | OCH$_2$CH$_2$OMe | n-Pr | 2 | CF$_3$ | |
| 10-36 | OCH$_2$CH$_2$OMe | i-Pr | 2 | CF$_3$ | |

TABLE 11

Compounds of the formula (I) according to the invention in which $R^2$ is phenylthio, $R^4$, $R^5$, $R^6$ and $R^7$ are each hydrogen and $R^3$ and $R^8$ together are an ethylene group.

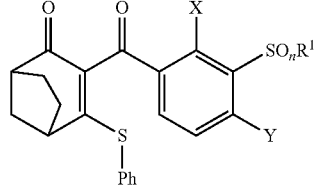

(I)

| No. | X | $R^1$ | n | Y | Physical data: $^1$H-NMR: δ [CDCl$_3$] |
|---|---|---|---|---|---|
| 11-1 | OMe | Me | 0 | CF$_3$ | |
| 11-2 | OMe | Et | 0 | CF$_3$ | |
| 11-3 | OMe | n-Pr | 0 | CF$_3$ | |
| 11-4 | OMe | i-Pr | 0 | CF$_3$ | |
| 11-5 | OMe | Me | 1 | CF$_3$ | |
| 11-6 | OMe | Et | 1 | CF$_3$ | |
| 11-7 | OMe | n-Pr | 1 | CF$_3$ | |
| 11-8 | OMe | i-Pr | 1 | CF$_3$ | |
| 11-9 | OMe | Me | 2 | CF$_3$ | |
| 11-10 | OMe | Et | 2 | CF$_3$ | |

TABLE 11-continued

Compounds of the formula (I) according to the invention in which $R^2$ is phenylthio, $R^4$, $R^5$, $R^6$ and $R^7$ are each hydrogen and $R^3$ and $R^8$ together are an ethylene group.

(I)

| No. | X | $R^1$ | n | Y | Physical data: $^1$H-NMR: δ [CDCl$_3$] |
|---|---|---|---|---|---|
| 11-11 | OMe | n-Pr | 2 | CF$_3$ | |
| 11-12 | OMe | i-Pr | 2 | CF$_3$ | |
| 11-13 | OEt | Me | 0 | CF$_3$ | |
| 11-14 | OEt | Et | 0 | CF$_3$ | |
| 11-15 | OEt | n-Pr | 0 | CF$_3$ | |
| 11-16 | OEt | i-Pr | 0 | CF$_3$ | |
| 11-17 | OEt | Me | 1 | CF$_3$ | |
| 11-18 | OEt | Et | 1 | CF$_3$ | |
| 11-19 | OEt | n-Pr | 1 | CF$_3$ | |
| 11-20 | OEt | i-Pr | 1 | CF$_3$ | |
| 11-21 | OEt | Me | 2 | CF$_3$ | |
| 11-22 | OEt | Et | 2 | CF$_3$ | |
| 11-23 | OEt | n-Pr | 2 | CF$_3$ | |
| 11-24 | OEt | i-Pr | 2 | CF$_3$ | |
| 11-25 | OCH$_2$CH$_2$OMe | Me | 0 | CF$_3$ | |
| 11-26 | OCH$_2$CH$_2$OMe | Et | 0 | CF$_3$ | |
| 11-27 | OCH$_2$CH$_2$OMe | n-Pr | 0 | CF$_3$ | |
| 11-28 | OCH$_2$CH$_2$OMe | i-Pr | 0 | CF$_3$ | |
| 11-29 | OCH$_2$CH$_2$OMe | Me | 1 | CF$_3$ | |
| 11-30 | OCH$_2$CH$_2$OMe | Et | 1 | CF$_3$ | |
| 11-31 | OCH$_2$CH$_2$OMe | n-Pr | 1 | CF$_3$ | |
| 11-32 | OCH$_2$CH$_2$OMe | i-Pr | 1 | CF$_3$ | |
| 11-33 | OCH$_2$CH$_2$OMe | Me | 2 | CF$_3$ | |
| 11-34 | OCH$_2$CH$_2$OMe | Et | 2 | CF$_3$ | |
| 11-35 | OCH$_2$CH$_2$OMe | n-Pr | 2 | CF$_3$ | |
| 11-36 | OCH$_2$CH$_2$OMe | i-Pr | 2 | CF$_3$ | |

TABLE 12

Compounds of the formula (II) according to the invention

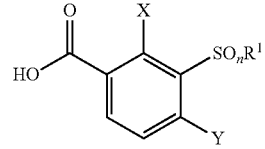

(II)

| No. | X | $R^1$ | n | Y | Physical data: $^1$H-NMR: δ [DMSO-d$_6$] |
|---|---|---|---|---|---|
| 12-1 | OH | Me | 0 | CF$_3$ | |
| 12-2 | OH | Et | 0 | CF$_3$ | |
| 12-3 | OH | n-Pr | 0 | CF$_3$ | |
| 12-4 | OH | i-Pr | 0 | CF$_3$ | |
| 12-5 | OH | Me | 1 | CF$_3$ | |
| 12-6 | OH | Et | 1 | CF$_3$ | |
| 12-7 | OH | n-Pr | 1 | CF$_3$ | |
| 12-8 | OH | i-Pr | 1 | CF$_3$ | |
| 12-9 | OH | Me | 2 | CF$_3$ | |
| 12-10 | OH | Et | 2 | CF$_3$ | |
| 12-11 | OH | n-Pr | 2 | CF$_3$ | |
| 12-12 | OH | i-Pr | 2 | CF$_3$ | |
| 12-13 | OMe | Me | 0 | CF$_3$ | 7.76 (d, 1H), 7.58 (d, 1H), |

TABLE 12-continued

Compounds of the formula (II) according to the invention $$\text{HO-C(=O)-C}_6\text{H}_2(\text{X})(\text{SO}_n\text{R}^1)(\text{Y}) \quad (II)$$

| No. | X | R¹ | n | Y | Physical data: ¹H-NMR: δ [DMSO-d₆] |
|---|---|---|---|---|---|
| | | | | | 3.91 (s, 3H), 2.40 (s, 3H) |
| 12-14 | OMe | Et | 0 | CF₃ | 7.78 (d, 1H), 7.61 (d, 1H), 3.90 (s, 3H), 2.95 (q, 2H), 1.07 (t, 3H) |
| 12-15 | OMe | n-Pr | 0 | CF₃ | |
| 12-16 | OMe | i-Pr | 0 | CF₃ | |
| 12-17 | OMe | Me | 1 | CF₃ | |
| 12-18 | OMe | Et | 1 | CF₃ | |
| 12-19 | OMe | n-Pr | 1 | CF₃ | |
| 12-20 | OMe | i-Pr | 1 | CF₃ | |
| 12-21 | OMe | Me | 2 | CF₃ | |
| 12-22 | OMe | Et | 2 | CF₃ | |
| 12-23 | OMe | n-Pr | 2 | CF₃ | |
| 12-24 | OMe | i-Pr | 2 | CF₃ | |
| 12-25 | OEt | Me | 0 | CF₃ | 7.78 (d, 1H), 7.60 (d, 1H), 4.12 (q, 2H), 2.43 (s, 3H), 1.37 (t, 3H) |
| 12-26 | OEt | Et | 0 | CF₃ | 7.78 (d, 1H), 7.61 (d, 1H), 4.12 (q, 2H), 2.98 (q, 2H), 1.36 (t, 3H), 1.08 (t, 3H) |
| 12-27 | OEt | n-Pr | 0 | CF₃ | |
| 12-28 | OEt | i-Pr | 0 | CF₃ | |
| 12-29 | OEt | Me | 1 | CF₃ | |
| 12-30 | OEt | Et | 1 | CF₃ | |
| 12-31 | OEt | n-Pr | 1 | CF₃ | |
| 12-32 | OEt | i-Pr | 1 | CF₃ | |
| 12-33 | OEt | Me | 2 | CF₃ | |
| 12-34 | OEt | Et | 2 | CF₃ | |
| 12-35 | OEt | n-Pr | 2 | CF₃ | |
| 12-36 | OEt | i-Pr | 2 | CF₃ | |
| 12-37 | O—CH₂—c-Pr | Me | 0 | CF₃ | 7.77 (d, 1H), 7.60 (d, 1H), 3.92 (d, 2H), 2.46 (s, 3H), 1.27 (m, 1H), 0.57 (m, 2H), 0.33 (m, 2H) |
| 12-38 | O—CH₂—c-Pr | Et | 0 | CF₃ | |
| 12-39 | O—CH₂—c-Pr | n-Pr | 0 | CF₃ | |
| 12-40 | O—CH₂—c-Pr | i-Pr | 0 | CF₃ | |
| 12-41 | O—CH₂—c-Pr | Me | 1 | CF₃ | |
| 12-42 | O—CH₂—c-Pr | Et | 1 | CF₃ | |
| 12-43 | O—CH₂—c-Pr | n-Pr | 1 | CF₃ | |
| 12-44 | O—CH₂—c-Pr | i-Pr | 1 | CF₃ | |
| 12-45 | O—CH₂—c-Pr | Me | 2 | CF₃ | |
| 12-46 | O—CH₂—c-Pr | Et | 2 | CF₃ | |
| 12-47 | O—CH₂—c-Pr | n-Pr | 2 | CF₃ | |
| 12-48 | O—CH₂—c-Pr | i-Pr | 2 | CF₃ | |
| 12-49 | OCH₂CH₂OMe | Me | 0 | CF₃ | 7.77 (d, 1H), 7.60 (d, 1H), 4.22 (t, 2H), 3.71 (t, 2H), 2.44 (s, 3H) |
| 12-50 | OCH₂CH₂OMe | Et | 0 | CF₃ | |
| 12-51 | OCH₂CH₂OMe | n-Pr | 0 | CF₃ | |
| 12-52 | OCH₂CH₂OMe | i-Pr | 0 | CF₃ | |
| 12-53 | OCH₂CH₂OMe | Me | 1 | CF₃ | |
| 12-54 | OCH₂CH₂OMe | Et | 1 | CF₃ | |
| 12-55 | OCH₂CH₂OMe | n-Pr | 1 | CF₃ | |
| 12-56 | OCH₂CH₂OMe | i-Pr | 1 | CF₃ | |
| 12-57 | OCH₂CH₂OMe | Me | 2 | CF₃ | |
| 12-58 | OCH₂CH₂OMe | Et | 2 | CF₃ | |
| 12-59 | OCH₂CH₂OMe | n-Pr | 2 | CF₃ | |
| 12-60 | OCH₂CH₂OMe | i-Pr | 2 | CF₃ | |
| 12-61 | OCH₂CH₂SMe | Me | 0 | CF₃ | |
| 12-62 | OCH₂CH₂SMe | Et | 0 | CF₃ | |
| 12-63 | OCH₂CH₂SMe | n-Pr | 0 | CF₃ | |
| 12-64 | OCH₂CH₂SMe | i-Pr | 0 | CF₃ | |
| 12-65 | OCH₂CH₂SMe | Me | 1 | CF₃ | |
| 12-66 | OCH₂CH₂SMe | Et | 1 | CF₃ | |
| 12-67 | OCH₂CH₂SMe | n-Pr | 1 | CF₃ | |
| 12-68 | OCH₂CH₂SMe | i-Pr | 1 | CF₃ | |
| 12-69 | OCH₂CH₂SMe | Me | 2 | CF₃ | |
| 12-70 | OCH₂CH₂SMe | Et | 2 | CF₃ | |
| 12-71 | OCH₂CH₂SMe | n-Pr | 2 | CF₃ | |
| 12-72 | OCH₂CH₂SMe | i-Pr | 2 | CF₃ | |
| 12-73 | OCH₂CH₂SO₂Me | Me | 0 | CF₃ | |
| 12-74 | OCH₂CH₂SO₂Me | Et | 0 | CF₃ | |
| 12-75 | OCH₂CH₂SO₂Me | n-Pr | 0 | CF₃ | |
| 12-76 | OCH₂CH₂SO₂Me | i-Pr | 0 | CF₃ | |
| 12-77 | OCH₂CH₂SO₂Me | Me | 1 | CF₃ | |
| 12-78 | OCH₂CH₂SO₂Me | Et | 1 | CF₃ | |
| 12-79 | OCH₂CH₂SO₂Me | n-Pr | 1 | CF₃ | |
| 12-80 | OCH₂CH₂SO₂Me | i-Pr | 1 | CF₃ | |
| 12-81 | OCH₂CH₂SO₂Me | Me | 2 | CF₃ | |
| 12-82 | OCH₂CH₂SO₂Me | Et | 2 | CF₃ | |
| 12-83 | OCH₂CH₂SO₂Me | n-Pr | 2 | CF₃ | |
| 12-84 | OCH₂CH₂SO₂Me | i-Pr | 2 | CF₃ | |
| 12-85 | OCOMe | Me | 0 | CF₃ | |
| 12-86 | OCOMe | Et | 0 | CF₃ | |
| 12-87 | OCOMe | n-Pr | 0 | CF₃ | |
| 12-88 | OCOMe | i-Pr | 0 | CF₃ | |
| 12-89 | OCOMe | Me | 1 | CF₃ | |
| 12-90 | OCOMe | Et | 1 | CF₃ | |
| 12-91 | OCOMe | n-Pr | 1 | CF₃ | |
| 12-92 | OCOMe | i-Pr | 1 | CF₃ | |
| 12-93 | OCOMe | Me | 2 | CF₃ | |
| 12-94 | OCOMe | Et | 2 | CF₃ | |
| 12-95 | OCOMe | n-Pr | 2 | CF₃ | |
| 12-96 | OCOMe | i-Pr | 2 | CF₃ | |
| 12-97 | OSO₂Me | Me | 0 | CF₃ | |
| 12-98 | OSO₂Me | Et | 0 | CF₃ | |
| 12-99 | OSO₂Me | n-Pr | 0 | CF₃ | |
| 12-100 | OSO₂Me | i-Pr | 0 | CF₃ | |
| 12-101 | OSO₂Me | Me | 1 | CF₃ | |
| 12-102 | OSO₂Me | Et | 1 | CF₃ | |
| 12-103 | OSO₂Me | n-Pr | 1 | CF₃ | |
| 12-104 | OSO₂Me | i-Pr | 1 | CF₃ | |
| 12-105 | OSO₂Me | Me | 2 | CF₃ | |
| 12-106 | OSO₂Me | Et | 2 | CF₃ | |
| 12-107 | OSO₂Me | n-Pr | 2 | CF₃ | |
| 12-108 | OSO₂Me | i-Pr | 2 | CF₃ | |
| 12-109 | OMe | Me | 0 | C₂F₅ | |
| 12-110 | OMe | Et | 0 | C₂F₅ | |
| 12-111 | OMe | n-Pr | 0 | C₂F₅ | |
| 12-112 | OMe | i-Pr | 0 | C₂F₅ | |
| 12-113 | OMe | Me | 1 | C₂F₅ | |
| 12-114 | OMe | Et | 1 | C₂F₅ | |
| 12-115 | OMe | n-Pr | 1 | C₂F₅ | |
| 12-116 | OMe | i-Pr | 1 | C₂F₅ | |
| 12-117 | OMe | Me | 2 | C₂F₅ | |
| 12-118 | OMe | Et | 2 | C₂F₅ | |

TABLE 12-continued

Compounds of the formula (II) according to the invention (II)

| No. | X | R¹ | n | Y | Physical data: ¹H-NMR: δ [DMSO-d₆] |
|---|---|---|---|---|---|
| 12-119 | OMe | n-Pr | 2 | $C_2F_5$ | |
| 12-120 | OMe | i-Pr | 2 | $C_2F_5$ | |
| 12-121 | OEt | Me | 0 | $C_2F_5$ | |
| 12-122 | OEt | Et | 0 | $C_2F_5$ | |
| 12-123 | OEt | n-Pr | 0 | $C_2F_5$ | |
| 12-124 | OEt | i-Pr | 0 | $C_2F_5$ | |
| 12-125 | OEt | Me | 1 | $C_2F_5$ | |
| 12-126 | OEt | Et | 1 | $C_2F_5$ | |
| 12-127 | OEt | n-Pr | 1 | $C_2F_5$ | |
| 12-128 | OEt | i-Pr | 1 | $C_2F_5$ | |
| 12-129 | OEt | Me | 2 | $C_2F_5$ | |
| 12-130 | OEt | Et | 2 | $C_2F_5$ | |
| 12-131 | OEt | n-Pr | 2 | $C_2F_5$ | |
| 12-132 | OEt | i-Pr | 2 | $C_2F_5$ | |
| 12-133 | O—CH₂—c-Pr | Me | 0 | $C_2F_5$ | |
| 12-134 | O—CH₂—c-Pr | Et | 0 | $C_2F_5$ | |
| 12-135 | O—CH₂—c-Pr | n-Pr | 0 | $C_2F_5$ | |
| 12-136 | O—CH₂—c-Pr | i-Pr | 0 | $C_2F_5$ | |
| 12-137 | O—CH₂—c-Pr | Me | 1 | $C_2F_5$ | |
| 12-138 | O—CH₂—c-Pr | Et | 1 | $C_2F_5$ | |
| 12-139 | O—CH₂—c-Pr | n-Pr | 1 | $C_2F_5$ | |
| 12-140 | O—CH₂—c-Pr | i-Pr | 1 | $C_2F_5$ | |
| 12-141 | O—CH₂—c-Pr | Me | 2 | $C_2F_5$ | |
| 12-142 | O—CH₂—c-Pr | Et | 2 | $C_2F_5$ | |
| 12-143 | O—CH₂—c-Pr | n-Pr | 2 | $C_2F_5$ | |
| 12-144 | O—CH₂—c-Pr | i-Pr | 2 | $C_2F_5$ | |
| 12-145 | OCH₂CH₂OMe | Me | 0 | $C_2F_5$ | |
| 12-146 | OCH₂CH₂OMe | Et | 0 | $C_2F_5$ | |
| 12-147 | OCH₂CH₂OMe | n-Pr | 0 | $C_2F_5$ | |
| 12-148 | OCH₂CH₂OMe | i-Pr | 0 | $C_2F_5$ | |
| 12-149 | OCH₂CH₂OMe | Me | 1 | $C_2F_5$ | |
| 12-150 | OCH₂CH₂OMe | Et | 1 | $C_2F_5$ | |
| 12-151 | OCH₂CH₂OMe | n-Pr | 1 | $C_2F_5$ | |
| 12-152 | OCH₂CH₂OMe | i-Pr | 1 | $C_2F_5$ | |
| 12-153 | OCH₂CH₂OMe | Me | 2 | $C_2F_5$ | |
| 12-154 | OCH₂CH₂OMe | Et | 2 | $C_2F_5$ | |
| 12-155 | OCH₂CH₂OMe | n-Pr | 2 | $C_2F_5$ | |
| 12-156 | OCH₂CH₂OMe | i-Pr | 2 | $C_2F_5$ | |
| 12-157 | OCH₂CH₂SMe | Me | 0 | $C_2F_5$ | |
| 12-158 | OCH₂CH₂SMe | Et | 0 | $C_2F_5$ | |
| 12-159 | OCH₂CH₂SMe | n-Pr | 0 | $C_2F_5$ | |
| 12-160 | OCH₂CH₂SMe | i-Pr | 0 | $C_2F_5$ | |
| 12-161 | OCH₂CH₂SMe | Me | 1 | $C_2F_5$ | |
| 12-162 | OCH₂CH₂SMe | Et | 1 | $C_2F_5$ | |
| 12-163 | OCH₂CH₂SMe | n-Pr | 1 | $C_2F_5$ | |
| 12-164 | OCH₂CH₂SMe | i-Pr | 1 | $C_2F_5$ | |
| 12-165 | OCH₂CH₂SMe | Me | 2 | $C_2F_5$ | |
| 12-166 | OCH₂CH₂SMe | Et | 2 | $C_2F_5$ | |
| 12-167 | OCH₂CH₂SMe | n-Pr | 2 | $C_2F_5$ | |
| 12-168 | OCH₂CH₂SMe | i-Pr | 2 | $C_2F_5$ | |
| 12-169 | OCH₂CH₂SO₂Me | Me | 0 | $C_2F_5$ | |
| 12-170 | OCH₂CH₂SO₂Me | Et | 0 | $C_2F_5$ | |
| 12-171 | OCH₂CH₂SO₂Me | n-Pr | 0 | $C_2F_5$ | |
| 12-172 | OCH₂CH₂SO₂Me | i-Pr | 0 | $C_2F_5$ | |
| 12-173 | OCH₂CH₂SO₂Me | Me | 1 | $C_2F_5$ | |
| 12-174 | OCH₂CH₂SO₂Me | Et | 1 | $C_2F_5$ | |
| 12-175 | OCH₂CH₂SO₂Me | n-Pr | 1 | $C_2F_5$ | |
| 12-176 | OCH₂CH₂SO₂Me | i-Pr | 1 | $C_2F_5$ | |
| 12-177 | OCH₂CH₂SO₂Me | Me | 2 | $C_2F_5$ | |
| 12-178 | OCH₂CH₂SO₂Me | Et | 2 | $C_2F_5$ | |
| 12-179 | OCH₂CH₂SO₂Me | n-Pr | 2 | $C_2F_5$ | |
| 12-180 | OCH₂CH₂SO₂Me | i-Pr | 2 | $C_2F_5$ | |
| 12-181 | OMe | Me | 0 | $CCl_3$ | |
| 12-182 | OMe | Et | 0 | $CCl_3$ | |
| 12-183 | OMe | n-Pr | 0 | $CCl_3$ | |
| 12-184 | OMe | i-Pr | 0 | $CCl_3$ | |
| 12-185 | OMe | Me | 1 | $CCl_3$ | |
| 12-186 | OMe | Et | 1 | $CCl_3$ | |
| 12-187 | OMe | n-Pr | 1 | $CCl_3$ | |
| 12-188 | OMe | i-Pr | 1 | $CCl_3$ | |
| 12-189 | OMe | Me | 2 | $CCl_3$ | |
| 12-190 | OMe | Et | 2 | $CCl_3$ | |
| 12-191 | OMe | n-Pr | 2 | $CCl_3$ | |
| 12-192 | OMe | i-Pr | 2 | $CCl_3$ | |
| 12-193 | OEt | Me | 0 | $CCl_3$ | |
| 12-194 | OEt | Et | 0 | $CCl_3$ | |
| 12-195 | OEt | n-Pr | 0 | $CCl_3$ | |
| 12-196 | OEt | i-Pr | 0 | $CCl_3$ | |
| 12-197 | OEt | Me | 1 | $CCl_3$ | |
| 12-198 | OEt | Et | 1 | $CCl_3$ | |
| 12-199 | OEt | n-Pr | 1 | $CCl_3$ | |
| 12-200 | OEt | i-Pr | 1 | $CCl_3$ | |
| 12-201 | OEt | Me | 2 | $CCl_3$ | |
| 12-202 | OEt | Et | 2 | $CCl_3$ | |
| 12-203 | OEt | n-Pr | 2 | $CCl_3$ | |
| 12-204 | OEt | i-Pr | 2 | $CCl_3$ | |
| 12-205 | O—CH₂—c-Pr | Me | 0 | $CCl_3$ | |
| 12-206 | O—CH₂—c-Pr | Et | 0 | $CCl_3$ | |
| 12-207 | O—CH₂—c-Pr | n-Pr | 0 | $CCl_3$ | |
| 12-208 | O—CH₂—c-Pr | i-Pr | 0 | $CCl_3$ | |
| 12-209 | O—CH₂—c-Pr | Me | 1 | $CCl_3$ | |
| 12-210 | O—CH₂—c-Pr | Et | 1 | $CCl_3$ | |
| 12-211 | O—CH₂—c-Pr | n-Pr | 1 | $CCl_3$ | |
| 12-212 | O—CH₂—c-Pr | i-Pr | 1 | $CCl_3$ | |
| 12-213 | O—CH₂—c-Pr | Me | 2 | $CCl_3$ | |
| 12-214 | O—CH₂—c-Pr | Et | 2 | $CCl_3$ | |
| 12-215 | O—CH₂—c-Pr | n-Pr | 2 | $CCl_3$ | |
| 12-216 | O—CH₂—c-Pr | i-Pr | 2 | $CCl_3$ | |
| 12-217 | OCH₂CH₂OMe | Me | 0 | $CCl_3$ | |
| 12-218 | OCH₂CH₂OMe | Et | 0 | $CCl_3$ | |
| 12-219 | OCH₂CH₂OMe | n-Pr | 0 | $CCl_3$ | |
| 12-220 | OCH₂CH₂OMe | i-Pr | 0 | $CCl_3$ | |
| 12-221 | OCH₂CH₂OMe | Me | 1 | $CCl_3$ | |
| 12-222 | OCH₂CH₂OMe | Et | 1 | $CCl_3$ | |
| 12-223 | OCH₂CH₂OMe | n-Pr | 1 | $CCl_3$ | |
| 12-224 | OCH₂CH₂OMe | i-Pr | 1 | $CCl_3$ | |
| 12-225 | OCH₂CH₂OMe | Me | 2 | $CCl_3$ | |
| 12-226 | OCH₂CH₂OMe | Et | 2 | $CCl_3$ | |
| 12-227 | OCH₂CH₂OMe | n-Pr | 2 | $CCl_3$ | |
| 12-228 | OCH₂CH₂OMe | i-Pr | 2 | $CCl_3$ | |
| 12-229 | OCH₂CH₂SMe | Me | 0 | $CCl_3$ | |
| 12-230 | OCH₂CH₂SMe | Et | 0 | $CCl_3$ | |
| 12-231 | OCH₂CH₂SMe | n-Pr | 0 | $CCl_3$ | |
| 12-232 | OCH₂CH₂SMe | i-Pr | 0 | $CCl_3$ | |
| 12-233 | OCH₂CH₂SMe | Me | 1 | $CCl_3$ | |
| 12-234 | OCH₂CH₂SMe | Et | 1 | $CCl_3$ | |
| 12-235 | OCH₂CH₂SMe | n-Pr | 1 | $CCl_3$ | |
| 12-236 | OCH₂CH₂SMe | i-Pr | 1 | $CCl_3$ | |
| 12-237 | OCH₂CH₂SMe | Me | 2 | $CCl_3$ | |
| 12-238 | OCH₂CH₂SMe | Et | 2 | $CCl_3$ | |
| 12-239 | OCH₂CH₂SMe | n-Pr | 2 | $CCl_3$ | |
| 12-240 | OCH₂CH₂SMe | i-Pr | 2 | $CCl_3$ | |
| 12-241 | OCH₂CH₂SO₂Me | Me | 0 | $CCl_3$ | |
| 12-242 | OCH₂CH₂SO₂Me | Et | 0 | $CCl_3$ | |
| 12-243 | OCH₂CH₂SO₂Me | n-Pr | 0 | $CCl_3$ | |
| 12-244 | OCH₂CH₂SO₂Me | i-Pr | 0 | $CCl_3$ | |
| 12-245 | OCH₂CH₂SO₂Me | Me | 1 | $CCl_3$ | |
| 12-246 | OCH₂CH₂SO₂Me | Et | 1 | $CCl_3$ | |
| 12-247 | OCH₂CH₂SO₂Me | n-Pr | 1 | $CCl_3$ | |
| 12-248 | OCH₂CH₂SO₂Me | i-Pr | 1 | $CCl_3$ | |

TABLE 12-continued

Compounds of the formula (II) according to the invention

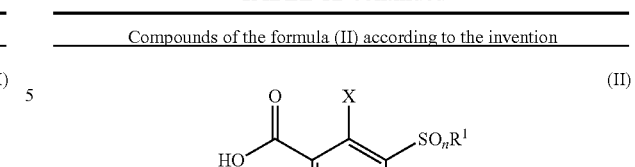

| No. | X | R¹ | n | Y |
|---|---|---|---|---|
| 12-249 | OCH$_2$CH$_2$SO$_2$Me | Me | 2 | CCl$_3$ |
| 12-250 | OCH$_2$CH$_2$SO$_2$Me | Et | 2 | CCl$_3$ |
| 12-251 | OCH$_2$CH$_2$SO$_2$Me | n-Pr | 2 | CCl$_3$ |
| 12-252 | OCH$_2$CH$_2$SO$_2$Me | i-Pr | 2 | CCl$_3$ |
| 12-253 | OMe | Me | 0 | CHF2 |
| 12-254 | OMe | Et | 0 | CHF2 |
| 12-255 | OMe | n-Pr | 0 | CHF2 |
| 12-256 | OMe | i-Pr | 0 | CHF2 |
| 12-257 | OMe | Me | 1 | CHF2 |
| 12-258 | OMe | Et | 1 | CHF2 |
| 12-259 | OMe | n-Pr | 1 | CHF2 |
| 12-260 | OMe | i-Pr | 1 | CHF2 |
| 12-261 | OMe | Me | 2 | CHF2 |
| 12-262 | OMe | Et | 2 | CHF2 |
| 12-263 | OMe | n-Pr | 2 | CHF2 |
| 12-264 | OMe | i-Pr | 2 | CHF2 |
| 12-265 | OEt | Me | 0 | CHF2 |
| 12-266 | OEt | Et | 0 | CHF2 |
| 12-267 | OEt | n-Pr | 0 | CHF2 |
| 12-268 | OEt | i-Pr | 0 | CHF2 |
| 12-269 | OEt | Me | 1 | CHF2 |
| 12-270 | OEt | Et | 1 | CHF2 |
| 12-271 | OEt | n-Pr | 1 | CHF2 |
| 12-272 | OEt | i-Pr | 1 | CHF2 |
| 12-273 | OEt | Me | 2 | CHF2 |
| 12-274 | OEt | Et | 2 | CHF2 |
| 12-275 | OEt | n-Pr | 2 | CHF2 |
| 12-276 | OEt | i-Pr | 2 | CHF2 |
| 12-277 | O—CH$_2$—c-Pr | Me | 0 | CHF2 |
| 12-278 | O—CH$_2$—c-Pr | Et | 0 | CHF2 |
| 12-279 | O—CH$_2$—c-Pr | n-Pr | 0 | CHF2 |
| 12-280 | O—CH$_2$—c-Pr | i-Pr | 0 | CHF2 |
| 12-281 | O—CH$_2$—c-Pr | Me | 1 | CHF2 |
| 12-282 | O—CH$_2$—c-Pr | Et | 1 | CHF2 |
| 12-283 | O—CH$_2$—c-Pr | n-Pr | 1 | CHF2 |
| 12-284 | O—CH$_2$—c-Pr | i-Pr | 1 | CHF2 |
| 12-285 | O—CH$_2$—c-Pr | Me | 2 | CHF2 |
| 12-286 | O—CH$_2$—c-Pr | Et | 2 | CHF2 |
| 12-287 | O—CH$_2$—c-Pr | n-Pr | 2 | CHF2 |
| 12-288 | O—CH$_2$—c-Pr | i-Pr | 2 | CHF2 |
| 12-289 | OCH$_2$CH$_2$OMe | Me | 0 | CHF2 |
| 12-290 | OCH$_2$CH$_2$OMe | Et | 0 | CHF2 |
| 12-291 | OCH$_2$CH$_2$OMe | n-Pr | 0 | CHF2 |
| 12-292 | OCH$_2$CH$_2$OMe | i-Pr | 0 | CHF2 |
| 12-293 | OCH$_2$CH$_2$OMe | Me | 1 | CHF2 |
| 12-294 | OCH$_2$CH$_2$OMe | Et | 1 | CHF2 |
| 12-295 | OCH$_2$CH$_2$OMe | n-Pr | 1 | CHF2 |
| 12-296 | OCH$_2$CH$_2$OMe | i-Pr | 1 | CHF2 |
| 12-297 | OCH$_2$CH$_2$OMe | Me | 2 | CHF2 |
| 12-298 | OCH$_2$CH$_2$OMe | Et | 2 | CHF2 |
| 12-299 | OCH$_2$CH$_2$OMe | n-Pr | 2 | CHF2 |
| 12-300 | OCH$_2$CH$_2$OMe | i-Pr | 2 | CHF2 |
| 12-301 | OCH$_2$CH$_2$SMe | Me | 0 | CHF2 |
| 12-302 | OCH$_2$CH$_2$SMe | Et | 0 | CHF2 |
| 12-303 | OCH$_2$CH$_2$SMe | n-Pr | 0 | CHF2 |
| 12-304 | OCH$_2$CH$_2$SMe | i-Pr | 0 | CHF2 |
| 12-305 | OCH$_2$CH$_2$SMe | Me | 1 | CHF2 |
| 12-306 | OCH$_2$CH$_2$SMe | Et | 1 | CHF2 |
| 12-307 | OCH$_2$CH$_2$SMe | n-Pr | 1 | CHF2 |
| 12-308 | OCH$_2$CH$_2$SMe | i-Pr | 1 | CHF2 |
| 12-309 | OCH$_2$CH$_2$SMe | Me | 2 | CHF2 |
| 12-310 | OCH$_2$CH$_2$SMe | Et | 2 | CHF2 |
| 12-311 | OCH$_2$CH$_2$SMe | n-Pr | 2 | CHF2 |
| 12-312 | OCH$_2$CH$_2$SMe | i-Pr | 2 | CHF2 |
| 12-313 | OCH$_2$CH$_2$SO$_2$Me | Me | 0 | CHF2 |
| 12-314 | OCH$_2$CH$_2$SO$_2$Me | Et | 0 | CHF2 |
| 12-315 | OCH$_2$CH$_2$SO$_2$Me | n-Pr | 0 | CHF2 |
| 12-316 | OCH$_2$CH$_2$SO$_2$Me | i-Pr | 0 | CHF2 |
| 12-317 | OCH$_2$CH$_2$SO$_2$Me | Me | 1 | CHF2 |
| 12-318 | OCH$_2$CH$_2$SO$_2$Me | Et | 1 | CHF2 |
| 12-319 | OCH$_2$CH$_2$SO$_2$Me | n-Pr | 1 | CHF2 |
| 12-320 | OCH$_2$CH$_2$SO$_2$Me | i-Pr | 1 | CHF2 |
| 12-321 | OCH$_2$CH$_2$SO$_2$Me | Me | 2 | CHF2 |
| 12-322 | OCH$_2$CH$_2$SO$_2$Me | Et | 2 | CHF2 |
| 12-323 | OCH$_2$CH$_2$SO$_2$Me | n-Pr | 2 | CHF2 |
| 12-324 | OCH$_2$CH$_2$SO$_2$Me | i-Pr | 2 | CHF2 |
| 12-325 | OMe | Me | 0 | CF(CF$_3$)$_2$ |
| 12-326 | OMe | Et | 0 | CF(CF$_3$)$_2$ |
| 12-327 | OMe | n-Pr | 0 | CF(CF$_3$)$_2$ |
| 12-328 | OMe | i-Pr | 0 | CF(CF$_3$)$_2$ |
| 12-329 | OMe | Me | 1 | CF(CF$_3$)$_2$ |
| 12-330 | OMe | Et | 1 | CF(CF$_3$)$_2$ |
| 12-331 | OMe | n-Pr | 1 | CF(CF$_3$)$_2$ |
| 12-332 | OMe | i-Pr | 1 | CF(CF$_3$)$_2$ |
| 12-333 | OMe | Me | 2 | CF(CF$_3$)$_2$ |
| 12-334 | OMe | Et | 2 | CF(CF$_3$)$_2$ |
| 12-335 | OMe | n-Pr | 2 | CF(CF$_3$)$_2$ |
| 12-336 | OMe | i-Pr | 2 | CF(CF$_3$)$_2$ |
| 12-337 | OEt | Me | 0 | CF(CF$_3$)$_2$ |
| 12-338 | OEt | Et | 0 | CF(CF$_3$)$_2$ |
| 12-339 | OEt | n-Pr | 0 | CF(CF$_3$)$_2$ |
| 12-340 | OEt | i-Pr | 0 | CF(CF$_3$)$_2$ |
| 12-341 | OEt | Me | 1 | CF(CF$_3$)$_2$ |
| 12-342 | OEt | Et | 1 | CF(CF$_3$)$_2$ |
| 12-343 | OEt | n-Pr | 1 | CF(CF$_3$)$_2$ |
| 12-344 | OEt | i-Pr | 1 | CF(CF$_3$)$_2$ |
| 12-345 | OEt | Me | 2 | CF(CF$_3$)$_2$ |
| 12-346 | OEt | Et | 2 | CF(CF$_3$)$_2$ |
| 12-347 | OEt | n-Pr | 2 | CF(CF$_3$)$_2$ |
| 12-348 | OEt | i-Pr | 2 | CF(CF$_3$)$_2$ |
| 12-349 | O—CH$_2$—c-Pr | Me | 0 | CF(CF$_3$)$_2$ |
| 12-350 | O—CH$_2$—c-Pr | Et | 0 | CF(CF$_3$)$_2$ |
| 12-351 | O—CH$_2$—c-Pr | n-Pr | 0 | CF(CF$_3$)$_2$ |
| 12-352 | O—CH$_2$—c-Pr | i-Pr | 0 | CF(CF$_3$)$_2$ |
| 12-353 | O—CH$_2$—c-Pr | Me | 1 | CF(CF$_3$)$_2$ |
| 12-354 | O—CH$_2$—c-Pr | Et | 1 | CF(CF$_3$)$_2$ |
| 12-355 | O—CH$_2$—c-Pr | n-Pr | 1 | CF(CF$_3$)$_2$ |
| 12-356 | O—CH$_2$—c-Pr | i-Pr | 1 | CF(CF$_3$)$_2$ |
| 12-357 | O—CH$_2$—c-Pr | Me | 2 | CF(CF$_3$)$_2$ |
| 12-358 | O—CH$_2$—c-Pr | Et | 2 | CF(CF$_3$)$_2$ |
| 12-359 | O—CH$_2$—c-Pr | n-Pr | 2 | CF(CF$_3$)$_2$ |
| 12-360 | O—CH$_2$—c-Pr | i-Pr | 2 | CF(CF$_3$)$_2$ |
| 12-361 | OCH$_2$CH$_2$OMe | Me | 0 | CF(CF$_3$)$_2$ |
| 12-362 | OCH$_2$CH$_2$OMe | Et | 0 | CF(CF$_3$)$_2$ |
| 12-363 | OCH$_2$CH$_2$OMe | n-Pr | 0 | CF(CF$_3$)$_2$ |
| 12-364 | OCH$_2$CH$_2$OMe | i-Pr | 0 | CF(CF$_3$)$_2$ |
| 12-365 | OCH$_2$CH$_2$OMe | Me | 1 | CF(CF$_3$)$_2$ |
| 12-366 | OCH$_2$CH$_2$OMe | Et | 1 | CF(CF$_3$)$_2$ |
| 12-367 | OCH$_2$CH$_2$OMe | n-Pr | 1 | CF(CF$_3$)$_2$ |
| 12-368 | OCH$_2$CH$_2$OMe | i-Pr | 1 | CF(CF$_3$)$_2$ |
| 12-369 | OCH$_2$CH$_2$OMe | Me | 2 | CF(CF$_3$)$_2$ |
| 12-370 | OCH$_2$CH$_2$OMe | Et | 2 | CF(CF$_3$)$_2$ |
| 12-371 | OCH$_2$CH$_2$OMe | n-Pr | 2 | CF(CF$_3$)$_2$ |
| 12-372 | OCH$_2$CH$_2$OMe | i-Pr | 2 | CF(CF$_3$)$_2$ |
| 12-373 | OCH$_2$CH$_2$SMe | Me | 0 | CF(CF$_3$)$_2$ |
| 12-374 | OCH$_2$CH$_2$SMe | Et | 0 | CF(CF$_3$)$_2$ |
| 12-375 | OCH$_2$CH$_2$SMe | n-Pr | 0 | CF(CF$_3$)$_2$ |
| 12-376 | OCH$_2$CH$_2$SMe | i-Pr | 0 | CF(CF$_3$)$_2$ |
| 12-377 | OCH$_2$CH$_2$SMe | Me | 1 | CF(CF$_3$)$_2$ |
| 12-378 | OCH$_2$CH$_2$SMe | Et | 1 | CF(CF$_3$)$_2$ |

TABLE 12-continued

Compounds of the formula (II) according to the invention $$\text{HO-C(=O)-C}_6\text{H}_2(\text{X})(\text{SO}_n\text{R}^1)(\text{Y}) \quad (II)$$

| No. | X | R¹ | n | Y | Physical data: ¹H-NMR: δ [DMSO-d₆] |
|---|---|---|---|---|---|
| 12-379 | OCH₂CH₂SMe | n-Pr | 1 | CF(CF₃)₂ | |
| 12-380 | OCH₂CH₂SMe | i-Pr | 1 | CF(CF₃)₂ | |
| 12-381 | OCH₂CH₂SMe | Me | 2 | CF(CF₃)₂ | |
| 12-382 | OCH₂CH₂SMe | Et | 2 | CF(CF₃)₂ | |
| 12-383 | OCH₂CH₂SMe | n-Pr | 2 | CF(CF₃)₂ | |
| 12-384 | OCH₂CH₂SMe | i-Pr | 2 | CF(CF₃)₂ | |
| 12-385 | OCH₂CH₂SO₂Me | Me | 0 | CF(CF₃)₂ | |
| 12-386 | OCH₂CH₂SO₂Me | Et | 0 | CF(CF₃)₂ | |
| 12-387 | OCH₂CH₂SO₂Me | n-Pr | 0 | CF(CF₃)₂ | |
| 12-388 | OCH₂CH₂SO₂Me | i-Pr | 0 | CF(CF₃)₂ | |
| 12-389 | OCH₂CH₂SO₂Me | Me | 1 | CF(CF₃)₂ | |
| 12-390 | OCH₂CH₂SO₂Me | Et | 1 | CF(CF₃)₂ | |
| 12-391 | OCH₂CH₂SO₂Me | n-Pr | 1 | CF(CF₃)₂ | |
| 12-392 | OCH₂CH₂SO₂Me | i-Pr | 1 | CF(CF₃)₂ | |
| 12-393 | OCH₂CH₂SO₂Me | Me | 2 | CF(CF₃)₂ | |
| 12-394 | OCH₂CH₂SO₂Me | Et | 2 | CF(CF₃)₂ | |
| 12-395 | OCH₂CH₂SO₂Me | n-Pr | 2 | CF(CF₃)₂ | |
| 12-396 | OCH₂CH₂SO₂Me | i-Pr | 2 | CF(CF₃)₂ | |

B. FORMULATION EXAMPLES a) A dust is obtained by mixing 10 parts by weight of a compound of the formula (I) and/or a salt thereof and 90 parts by weight of talc as inert substance and comminuting the mixture in a hammer mill.

b) A wettable powder which is readily dispersible in water is obtained by mixing 25 parts by weight of a compound of the formula (I) and/or a salt thereof, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A readily water-dispersible dispersion concentrate is obtained by mixing 20 parts by weight of a compound of the formula (I) and/or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or a salt thereof, 75 parts by weight of cyclohexanone as solvent and 10 parts by weight of oxethylated nonylphenol as emulsifier.

e) Water-dispersible granules are obtained by mixing
75 parts by weight of a compound of the formula (I) and/or a salt thereof,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spraying on water as granulating liquid.

f) Water-dispersible granules are also obtained by homogenizing and precomminuting, in a colloid mill,
25 parts by weight of a compound of the formula (I) and/or a salt thereof,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water
subsequently grinding the mixture in a bead mill and atomizing and drying the resulting suspension in a spray tower by means of a single-substance nozzle.

C. BIOLOGICAL EXAMPLES

1. Pre-Emergence Herbicidal Action Against Harmful Plants

Seeds of monocotyledonous or dicotyledonous weed plants or crop plants are planted in wood-fiber pots in sandy loam and covered with soil. The compounds according to the invention, formulated in the form of wettable powders (WP) or emulsion concentrates (EC), are then applied as aqueous suspension or emulsion at a water application rate of 600 to 800 l/ha (converted) with the addition of 0.2% of wetting agent to the surface of the covering soil. After the treatment, the pots are placed in a greenhouse and kept under good growth conditions for the test plants. The visual assessment of the damage to the test plants is carried out after a trial period of 3 weeks by comparison with untreated controls (herbicidal activity in percent (%): 100% activity=the plants have died, 0% activity=like control plants). Here, for example, the compounds Nos. 1-21, 5-17 and 5-21 each show, at an application rate of 80 g/ha, an activity of at least 90% against *Abutilon theophrasti* and *Veronica persica*. The compounds Nos. 2-21 and 2-17 each show, at an application rate of 80 g/ha, an activity of at least 90% against *Alopecurus myosuroides*, *Amaranthus retroflexus* and *Veronica persica*.

2. Post-Emergence Herbicidal Action Against Harmful Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP) or emulsion concentrates (EC), are then sprayed as aqueous suspension or emulsion at a water application rate of 600 to 800 l/ha (converted) with the addition of 0.2% of wetting agent onto the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants). Here, for example, the compounds Nos. 3-17, 5-21 and 2-17 each show, at an application rate of 80 g/ha, an activity of at least 90% against *Avena fatua*, *Matricaria inodora* and *Viola tricolor*. The compounds Nos. 1-13, 1-17, 1-21 and 2-21 each show, at an application rate of 80 g/ha, an activity of at least 90% against *Echinochloa crus galli*, *Pharbitis purpureum* and *Stellaria media*.

The invention claimed is:
1. A 2-(3-alkylthiobenzoyl)cyclohexanedione of formula (I) and/or a salt thereof

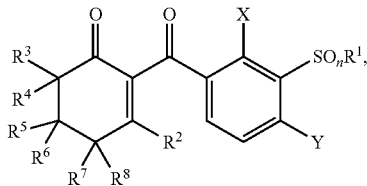

in which
$R^1$ is $(C_1-C_6)$-alkyl,
$R^2$ is hydroxyl, $SR^{13}$, or $NR^{14}R^{15}$,
$R^3$ and $R^8$ independently of one another are hydrogen or $(C_1-C_4)$-alkyl, or the radicals $R^3$ and $R^8$ together form the unit Z which represents an oxygen or sulfur atom or one to four methylene groups,
$R^4$ and $R^7$ independently of one another are hydrogen or $(C_1-C_4)$-alkyl,
$R^5$ and $R^6$ independently of one another are hydrogen or $(C_1-C_4)$-alkyl or together with the carbon atom to which they are attached form a carbonyl group,
X is $OR^9$, $OCOR^9$, or $OSO_2R^{10}$,
$R^9$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl-$(C_1-C_6)$-alkyl, where the six last-mentioned radicals are substituted by s radicals selected from the group consisting of halogen, $OR^{11}$ and $S(O)_m R^{12}$,
$R^{10}$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl-$(C_1-C_6)$-alkyl, where the six last-mentioned radicals are substituted by s radicals selected from the group consisting of halogen, $OR^{11}$ and $S(O)_m R^{12}$,
$R^{11}$ is hydrogen, $(C_1-C_6)$-alkyl, $(C_2-C_6)$-alkenyl or $(C_2-C_6)$-alkynyl,
$R^{12}$ is $(C_1-C_6)$-alkyl, $(C_2-C_6)$-alkenyl or $(C_2-C_6)$-alkynyl,
$R^{13}$ is $(C_1-C_4)$-alkyl, phenyl which is substituted by s radicals selected from the group consisting of nitro, cyano, $(C_1-C_4)$-alkyl, $(C_1-C_4)$-haloalkyl, $(C_1-C_4)$-alkoxy or $(C_1-C_4)$-haloalkoxy or is partially or fully halogenated phenyl,
$R^{14}$ is hydrogen, $(C_1-C_4)$-alkyl or $(C_1-C_4)$-alkoxy,
$R^{15}$ is hydrogen or $(C_1-C_4)$-alkyl,
or
$R^{14}$ and $R^{15}$ together with the nitrogen atom to which they are attached form a 5- or 6-membered saturated, partially saturated or unsaturated ring,
which contains zero, one or two heteroatoms selected from the group consisting of oxygen, sulfur and nitrogen, which is substituted by s radicals from the group consisting of cyano, halogen, $(C_1-C_4)$-alkyl, $(C_1-C_4)$-haloalkyl, $(C_1-C_4)$-alkoxy and $(C_1-C_4)$-haloalkoxy,
Y is $(C_1-C_6)$-haloalkyl,
m is 0, 1 or 2,
n is 0, 1 or 2,
s is 0, 1, 2 or 3.
2. The 2-(3-alkylthiobenzoyl)cyclohexanedione and/or salt as claimed in claim 1 in which
$R^1$ is methyl, ethyl, n-propyl or isopropyl,
$R^2$ is hydroxyl,
$R^3$ and $R^8$ independently of one another are hydrogen or $(C_1-C_4)$-alkyl, or the radicals $R^3$ and $R^8$ together form a methylene or ethylene group,
$R^4$ and $R^7$ independently of one another are hydrogen, methyl or ethyl,
$R^5$ and $R^6$ independently of one another are hydrogen, methyl or ethyl,
X is $OR^9$, $OCOR^9$, or $OSO_2R^{10}$,
$R^9$ is cyclopropylmethyl or $(C_1-C_6)$-alkyl substituted by s methoxy or ethoxy groups,
$R^{10}$ is $(C_1-C_6)$-alkyl substituted by s methoxy or ethoxy groups,
Y is $(C_1-C_3)$-haloalkyl,
n is 0, 1 or 2,
s is 0, 1, 2 or 3.
3. The 2-(3-alkylthiobenzoyl)cyclohexanedione and/or salt as claimed in claim 1 in which
$R^1$ is methyl, ethyl, n-propyl or isopropyl,
$R^2$ is hydroxyl,
$R^3$ and $R^8$ independently of one another are hydrogen, methyl or ethyl,
or the radicals $R^3$ and $R^8$ together form a methylene or ethylene group,
$R^4$ and $R^7$ independently of one another are hydrogen, methyl or ethyl,
$R^5$ and $R^6$ independently of one another are hydrogen, methyl or ethyl,
X is $OR^9$,
$R^9$ is cyclopropylmethyl or ethyl or methyl substituted by s methoxy or ethoxy groups,
Y is trichloromethyl, difluoromethyl, trifluoromethyl, pentafluoroethyl or heptafluoroisopropyl,
n is 0, 1 or 2,
s is 0, 1, 2 or 3.
4. A herbicidal composition which comprises a herbicidally effective amount of at least one compound as claimed in claim 1.
5. The herbicidal composition as claimed in claim 4 comprising a mixture with at least one formulation auxiliary.
6. A method for controlling unwanted plants which comprises applying an effective amount of at least one compound as claimed in claim 1 to plants and/or to a site of unwanted vegetation.
7. A herbicidal composition as claimed in claim 4 for controlling unwanted plants.
8. A composition as claimed in claim 7 wherein the compound of formula (I) and/or salt thereof is capable of controlling unwanted plants in crops of useful plants.
9. A composition as claimed in claim 8 wherein the useful plants are transgenic useful plants.

* * * * *